United States Patent
Shelton, IV et al.

(10) Patent No.: US 12,051,495 B2
(45) Date of Patent: Jul. 30, 2024

(54) PATIENT MONITORING USING DRUG ADMINISTRATION DEVICES

(71) Applicant: Janssen Pharmaceuticals, Inc., Titusville, NJ (US)

(72) Inventors: Frederick E. Shelton, IV, Hillsboro, OH (US); Monica A. Kapil, San Jose, CA (US); Emma L. Hubert, San Jose, CA (US); Jason L. Harris, Lebanon, OH (US)

(73) Assignee: Janssen Pharmaceuticals, Inc., Titusville, NJ (US)

( * ) Notice: Subject to any disclaimer, the term of this patent is extended or adjusted under 35 U.S.C. 154(b) by 961 days.

(21) Appl. No.: 17/068,863

(22) Filed: Oct. 13, 2020

(65) Prior Publication Data
US 2021/0350896 A1 Nov. 11, 2021

Related U.S. Application Data

(60) Provisional application No. 63/020,931, filed on May 6, 2020, provisional application No. 63/020,928, filed on May 6, 2020.

(51) Int. Cl.
*G16H 20/17* (2018.01)
*A61M 5/315* (2006.01)

(52) U.S. Cl.
CPC ........ *G16H 20/17* (2018.01); *A61M 5/31565* (2013.01); *A61M 2205/3327* (2013.01); *A61M 2205/502* (2013.01); *A61M 2205/52* (2013.01)

(58) Field of Classification Search
None
See application file for complete search history.

(56) References Cited

U.S. PATENT DOCUMENTS

| | | |
|---|---|---|
| 4,946,069 A | 8/1990 | Fuchs |
| 6,321,942 B1 | 11/2001 | Krampen et al. |
| 7,299,949 B2 | 11/2007 | Greiner-Perth |
| 8,585,659 B2 | 11/2013 | Shay |
| 8,696,616 B2 | 4/2014 | Baynham et al. |
| 8,812,100 B2 | 8/2014 | Voegele et al. |
| 9,129,054 B2 | 9/2015 | Nawana et al. |
| 9,168,000 B2 | 10/2015 | Dunki-Jacobs et al. |
| 9,314,808 B2 | 4/2016 | Allsop |
| 9,381,219 B2 | 7/2016 | Kaplan et al. |
| 9,427,580 B2 | 8/2016 | Bork et al. |
| 9,555,950 B2 | 1/2017 | Le Maner et al. |
| 9,610,429 B2 | 4/2017 | Harris et al. |
| 10,456,534 B2 | 10/2019 | Reisacher et al. |
| 10,569,071 B2 | 2/2020 | Harris et al. |
| 2002/0014951 A1 | 2/2002 | Kramer et al. |
| 2002/0042596 A1 | 4/2002 | Hartlaub et al. |
| 2002/0091454 A1 | 7/2002 | Vasko |
| 2007/0061393 A1* | 3/2007 | Moore .................... H04L 67/02 709/201 |

(Continued)

OTHER PUBLICATIONS

"Diet Coke and Mentos Explained," Weebly, dated no later than Mar. 16, 2020, 2 pages (available at <https://dietcoke-and-mentos.weebly.com/>).

(Continued)

*Primary Examiner* — Manuel A Mendez
(74) *Attorney, Agent, or Firm* — Mintz Levin Cohn Ferris Glovsky and Popeo, P.C.

(57) ABSTRACT

In general, systems and methods for patient monitoring using drug administration devices are provided.

20 Claims, 23 Drawing Sheets

(56) References Cited

U.S. PATENT DOCUMENTS

| | | | | |
|---|---|---|---|---|
| 2007/0106754 | A1* | 5/2007 | Moore | G16H 40/20 |
| | | | | 707/E17.116 |
| 2007/0251835 | A1 | 11/2007 | Mehta et al. | |
| 2008/0040151 | A1* | 2/2008 | Moore | G16H 40/67 |
| | | | | 705/2 |
| 2008/0139907 | A1 | 6/2008 | Rao et al. | |
| 2009/0069787 | A1 | 3/2009 | Estes et al. | |
| 2011/0295337 | A1 | 12/2011 | Albrecht et al. | |
| 2012/0095318 | A1 | 4/2012 | Galley et al. | |
| 2012/0330684 | A1 | 12/2012 | Jacobs et al. | |
| 2014/0257047 | A1* | 9/2014 | Sillay | H04L 63/10 |
| | | | | 600/595 |
| 2015/0274344 | A1 | 10/2015 | Sullivan et al. | |
| 2015/0297845 | A1 | 10/2015 | Shahaf et al. | |
| 2015/0359966 | A1 | 12/2015 | Day et al. | |
| 2017/0172462 | A1 | 6/2017 | Alghazi | |
| 2018/0060527 | A1 | 3/2018 | Kalyanpur et al. | |
| 2018/0361085 | A1 | 12/2018 | Malhotra et al. | |
| 2019/0200844 | A1 | 7/2019 | Shelton, IV et al. | |
| 2019/0200981 | A1 | 7/2019 | Harris et al. | |
| 2019/0201046 | A1 | 7/2019 | Shelton, IV et al. | |
| 2019/0201114 | A1 | 7/2019 | Shelton, IV et al. | |
| 2019/0201140 | A1 | 7/2019 | Yates et al. | |
| 2019/0206004 | A1 | 7/2019 | Shelton, IV et al. | |
| 2019/0206555 | A1 | 7/2019 | Morgan et al. | |
| 2019/0207857 | A1 | 7/2019 | Shelton, IV et al. | |

OTHER PUBLICATIONS

"Dual Component Epoxy Cartridges K-Series Syringe," Adhesive Dispensing Ltd., dated no later than Mar. 21, 2020, 2 pages (available at <https://www.adhesivedispensing.net/Dual_Component_K_Series_Dispensing_s/236.htm>).

"Molecular Sieve vs Silica Gel: What's the Difference?", Multisorb Fixation Group, dated no later than Mar. 24, 2020, 2 pages (available at <https://www.multisorb.com/blog/pharmaceuticals/molecular-sieve-vs-silica-gel-whats-the-difference/>).

"Orbeez® Toys—Add Water to Make Them Grow!", Maya Toys, dated no later than Mar. 24, 2020, 2 pages (available at <https://mayatoys.net/pages/orbeez>).

"Philips Medication Dispenser," Philips Lifeline, dated no later than Mar. 17, 2020, 6 pages (available at <https://www.lifeline.philips.com/pill-dispenser/health-mdp.html>).

"Study Shows High Altitude and Medication May Not Mix," healthNEWS, University of Cincinnati Academic Health Center, Jan. 14, 1999, 1 page (available at <http://healthnews.uc.edu/news/?/153/>).

"The Companion Dual Chamber Reconstitution Syringe," Credence MedSystems, Inc, dated no later than Mar. 18, 2020, 3 pages <available at <https://www.credencemed.com/dual-chamber/>).

"VapourSoft® Technology," Bespak Europe Ltd., dated no later than Mar. 16, 2020, 2 pages (available at <https://bespak.com/products/injection-devices/vapoursoft-technology/>).

Jae Hung Park et al., "Biodegradable Polymers for Microencapsulation of Drugs," Molecules 2005, 10, p. 146-161.

Lam YY and Ravussin, E., "Analysis of energy metabolism in humans: A review of methodologies," Mol Metab. Nov. 2016; 5(11): 1057-1071 (available at <https://www.ncbi.nlm.nih.gov/pmc/articles/PMC5081410/>).

Man Chiu Fung, "Experimental and numerical study of spray characteristics of nasal spray devices," School of Aerospace, Mechanical and Manufacturing Engineering Science, Engineering and Technology Portfolio, RMIT University, Aug. 2013 (179 pages).

Rafi, "14 List of Chemicals That Glow Under Black Light—Application," Jan. 24, 2018, 3 pages (available at <https://azchemistry.com/list-of-chemicals-that-glow-under-black-light>).

* cited by examiner

PATIENT MONITORING USING DRUG ADMINISTRATION DEVICES

CROSS REFERENCE TO RELATED APPLICATIONS

The present application claims priority to U.S. Prov. App. No. 63/020,928 entitled "Interconnection Of Drug Administration Systems" filed May 6, 2020, and U.S. Prov. App. No. 63/020,931 entitled "Drug Delivery Adjustment" filed May 6, 2020, which are hereby incorporated by reference in their entireties.

FIELD

The present disclosure relates generally to patient monitoring using drug administration devices.

BACKGROUND

Pharmaceutical products (including large and small molecule pharmaceuticals, hereinafter "drugs") are administered to patients in a variety of different ways for the treatment of specific medical indications. Regardless of the manner of the administration, care must be taken when administering drugs to avoid adverse effects on the patient. For example, care must be taken not to administer more than a safe amount of the drug to the patient. This requires consideration of the amount of dose given and the time frame over which the dose is delivered, sometimes in relation to previous doses, or doses of other drugs. Moreover, care must be taken not to inadvertently administer an incorrect drug to the patient, or drugs that have degraded due to their age or storage conditions. All of these considerations can be conveyed in guidance associated with the specific drugs or drug combinations. However, this guidance is not always followed correctly, for example due to mistakes, such as human error. This can lead to adverse effects on the patient or result in inappropriate drug administration, for example insufficient or excessive volume of drug being administered for the specific medical indication.

Patients rarely share the same medical characteristics. For example, patients generally have different ages, weights, general states of health, and medical histories. Therefore the same illness tends to affect patients differently. Thus, while guidance supplied with specific drugs may aid a medical practitioner or patient in determining a suitable dosage amount, dosage frequency, and dosage time (dosage regimen) it will not necessarily inform the medical practitioner or patient of the optimum dosage for a particular patient. In order to determine the optimum dosage, the medical practitioner or patient would have to measure some or all possible factors affecting a patient and consider how the different factors interact. This is often impossible, and so medical practitioners or patients have to make a best guess as to the optimum dosage based on information that they have observed about the patient. These best guesses will rarely result in timely administration of an optimum dosage. Moreover, because the best guess is based on data observed by the medical practitioner or patient, there is an undesirable element of subjectivity and possibility of user error when determining or attempting to administer the best guess dosage.

In relation to how a drug is administered to the patient, there are various dosage forms that can be used. For example, these dosage forms may include parenteral, inhalational, oral, ophthalmic, topical, and suppository forms of one or more drugs.

The dosage forms can be administered directly to the patient via a drug administration device. There are a number of different types of drug administration devices commonly available for delivery of the various dosage forms including: syringes, injection devices (e.g., autoinjectors, jet injectors, and infusion pumps), and inhalers.

SUMMARY

In general, systems and methods for patient monitoring using drug administration devices are provided.

In one aspect, a surgical system is provided that in one embodiment includes a drug administration device configured to deliver a drug to a patient during performance of a surgical procedure on the patient. The drug administration device includes a first sensor configured to gather data, during the performance of the surgical procedure, regarding a first characteristic. The drug administration device includes a first communications interface. The surgical system also includes a memory configured to store therein an algorithm including at least one variable parameter. The surgical system also includes a processor configured to control delivery of a dose of the drug from the drug administration device to the patient, during the performance of the surgical procedure, by executing the algorithm. The first communications interface is configured to communicate, during the performance of the surgical procedure, the gathered data and data indicating that the algorithm was executed to a server external to and separate from the drug administration device.

The surgical system can vary in any number of ways. For example, the surgical system can also include a user interface configured to provide, during the performance of the surgical procedure, information to a user indicative of the data gathered by the first sensor. In at least some embodiments, the drug administration device includes the user interface. In at least some embodiments, the server includes a surgical hub, and the surgical hub can include the user interface.

For another example, the drug administration device can include the memory and the processor.

For yet another example, a value of the at least one variable parameter can be based on the data gathered by the first sensor. In at least some embodiments, the processor can also be configured to change, during the performance of the surgical procedure, the at least one variable parameter of the algorithm stored in the memory based on the data gathered by the first sensor, and, after changing the at least one variable parameter, control delivery of another dose of the drug from the drug administration device to the patient, during the performance of the surgical procedure, by executing the algorithm. In at least some embodiments, the at least one variable parameter can include at least one of a rate of delivery of the drug from the drug administration device to the patient, and a time interval between dose deliveries.

For still another example, the surgical system can also include a second sensor external to and separate from the drug administration device, the second sensor can be configured to gather second data, during the performance of the surgical procedure, regarding a second characteristic, and the first communications interface can be configured to receive the second data from the server. In at least some embodiments, a value of the at least one variable parameter can be based on the second data, and the processor can be also configured to change, during the performance of the surgical procedure, the at least one variable parameter of the algorithm stored in the memory based on the second data, and, after changing the at least one variable parameter, control delivery of another dose of the drug from the drug administration device to the patient, during the performance of the surgical procedure, by executing the algorithm. In at least some embodiments, the first sensor can be configured to gather data at a rate stored in the memory, and the processor can also be configured to modify the rate based on the second data.

For another example, the drug administration device can be one of a syringe and an injection device.

In another aspect, a surgical method is provided that in one embodiment includes gathering data using a first sensor during performance of a surgical procedure on a patient. The surgical method also includes controlling, using a processor, delivery of a dose of a drug from a drug administration device to the patient, during the performance of the surgical procedure, by executing an algorithm stored in a memory, the algorithm including at least one variable parameter. The surgical method also includes communicating, using a first communications interface and during the performance of the surgical procedure, the gathered data and data indicating that the algorithm was executed to a server external to and separate from the drug administration device.

The surgical method can have any number of variations. For example, the surgical method can also include providing, using a user interface and during the performance of the surgical procedure, information to a user indicative of the data gathered by the first sensor. In at least some embodiments, at least one of the server and the drug administration device can include the user interface.

For another example, the surgical method can also include, using the processor changing, during the performance of the surgical procedure, the at least one variable parameter of the algorithm stored in the memory based on the data gathered by the first sensor, and, after changing the at least one variable parameter, controlling delivery of another dose of the drug from the drug administration device to the patient, during the performance of the surgical procedure, by executing the algorithm.

For yet another example, the surgical method can also include gathering, using a second sensor external to and separate from the drug administration device, second data, during the performance of the surgical procedure, regarding a second characteristic, and receiving, at the first communications interface the second data from the server. In at least some embodiments, the surgical method can also include, using the processor changing, during the performance of the surgical procedure, the at least one variable parameter of the algorithm stored in the memory based on the second data, and, after changing the at least one variable parameter, controlling delivery of another dose of the drug from the drug administration device to the patient, during the performance of the surgical procedure, by executing the algorithm. In at least some embodiments, the first sensor can be configured to gather data at a rate stored in the memory, and the surgical method can also include, using the processor, modifying the rate based on the second data.

For still another example, the drug administration device can be one of a syringe and an injection device.

BRIEF DESCRIPTION OF DRAWINGS

The present invention is described by way of reference to the accompanying figures which are as follows.

DETAILED DESCRIPTION

Certain exemplary embodiments will now be described to provide an overall understanding of the principles of the structure, function, manufacture, and use of the devices, systems, and methods disclosed herein. One or more examples of these embodiments are illustrated in the accompanying drawings. A person skilled in the art will understand that the devices, systems, and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. A person skilled in the art will appreciate that a dimension may not be a precise value but nevertheless be considered to be at about that value due to any number of factors such as manufacturing tolerances and sensitivity of measurement equipment. Sizes and shapes of the systems and devices, and the components thereof, can depend at least on the size and shape of components with which the systems and devices will be used.

Examples of various types of drug administration devices, namely: an autoinjector 100, an infusion pump 200, and an inhaler 300, are described below.

Autoinjectors

Figure 1:
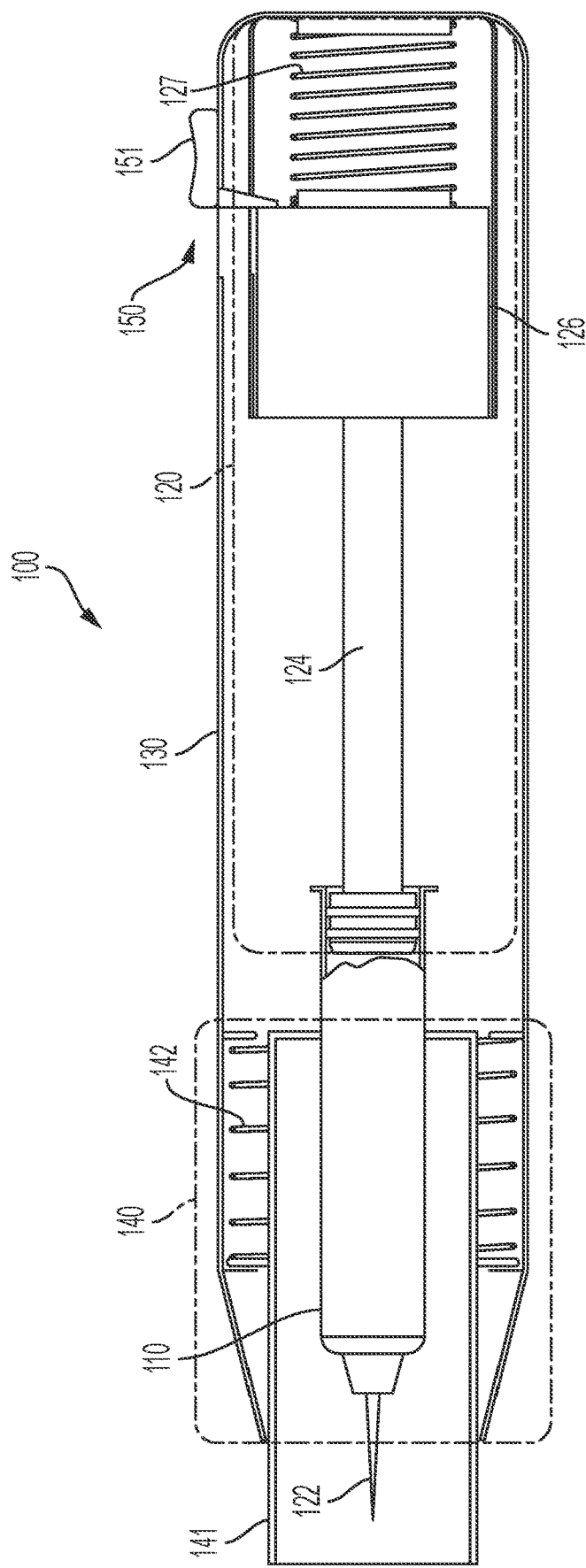
FIG. 1 is a schematic view of one embodiment of a first type of drug administration device, namely an autoinjector.

FIG. 1 is a schematic exemplary view of a first type of drug delivery device (also referred to herein as a "drug administration device"), namely an injection device, in this example an autoinjector 100, useable with embodiments described herein. The autoinjector 100 includes a drug holder 110, which retains a drug to be dispensed, and a dispensing mechanism 120, which is configured to dispense a drug from the drug holder 110 so that it can be administered to a patient. The drug holder 110 is typically in the form of a container which contains the drug, for example it may be provided in the form of a syringe or a vial, or be any other suitable container which can hold the drug. The autoinjector 100 includes a discharge nozzle 122, for example a needle of a syringe, which is provided at a distal end of the drug holder 110. The dispensing mechanism 120 includes a drive element 124, which itself may also include a piston and/or a piston rod, and drive mechanism 126. The dispensing mechanism 120 is located proximal to the end of the drug holder 110 and towards the proximal end of the autoinjector 100.

The autoinjector 100 includes a housing 130 which contains the drug holder 110, the drive element 124, and the drive mechanism 126 within the body of the housing 130, as well as containing the discharge nozzle 122, which, prior to injection, would typically be contained fully within the housing 130, but which would extend out of the housing 130 during an injection sequence to deliver the drug. The dispensing mechanism 120 is arranged so that the drive element 124 is advanced through the drug holder 110 in order to dispense the drug through the discharge nozzle 122, thereby allowing the autoinjector 100 to administer a drug retained in drug holder 110 to a patient. In some instances, a user may advance the drive element 124 through the drug holder 110 manually. In other instances, the drive element 124 may be advanced through the drug holder 110 under control of a robotic surgical system. In other instances, the drive mechanism 126 may include a stored energy source 127 which advances the drive element 124 without user assistance. The stored energy source 127 may include a resilient biasing member such as a spring, or a pressurized gas, or electronically powered motor and/or gearbox.

The autoinjector 100 includes a dispensing mechanism protection mechanism 140. The dispensing mechanism protection mechanism 140 typically has two functions. Firstly, the dispensing mechanism protection mechanism 140 can function to prevent access to the discharge nozzle 122 prior to and after injection. Secondly, the autoinjector 100 can function, such that when put into an activated state, e.g., the dispensing mechanism protection mechanism 140 is moved to an unlocked position, the dispensing mechanism 120 can be activated.

The protection mechanism 140 covers at least a part of the discharge nozzle 122 when the drug holder 110 is in its retracted position proximally within the housing 130. This is to impede contact between the discharge nozzle 122 and a user. Alternatively, or in addition, the protection mechanism 140 is itself configured to retract proximally to expose the discharge nozzle 122 so that it can be brought into contact with a patient. The protection mechanism 140 includes a shield member 141 and return spring 142. The return spring 142 acts to extend the shield member 141 from the housing 130, thereby covering the discharge nozzle 122 when no force is applied to the distal end of the protection mechanism 140. If a user applies a force to the shield member 141 against the action of the return spring 142 to overcome the bias of the return spring 142 (or a robotic surgical system causes such a force to be provided to the shield member 141), the shield member 141 retracts within the housing 130, thereby exposing the discharge nozzle 122. The protection mechanism 140 may alternatively, or in addition, include an extension mechanism (not shown) for extending the discharge nozzle 122 beyond the housing 130, and may further include a retracting mechanism (not shown) for retracting the discharge nozzle 122 within the housing 130. The protection mechanism 140 may alternatively, or in addition, include a housing cap and/or discharge nozzle boot, which can be attached to the autoinjector 100. Removal of the housing cap would typically also remove the discharge nozzle boot from the discharge nozzle 122.

The autoinjector 100 also includes a trigger 150. The trigger 150 includes a trigger button 151 which is located on an external surface of the housing 130 so that it is accessible by a user of the autoinjector 100 and/or by a robotic surgical system configured to control actuation of the trigger 150. When the trigger 150 is pressed by a user (or a robotic surgical system causes the trigger 150 to be pressed), it acts to release the drive mechanism 126 so that, via the drive element 124, the drug is then driven out of the drug holder 110 via the discharge nozzle 122.

The trigger 150 can also cooperate with the shield member 141 in such a way that the trigger 150 is prevented from being activated until the shield member 141 has been retracted proximally sufficiently into the housing 130 into an unlocked position, for example by pushing a distal end of the shield member 141 against the skin of a patient. When this has been done, the trigger 150 becomes unlocked, and the autoinjector 100 is activated such that the trigger 150 can be depressed and the injection and/or drug delivery sequence is then initiated. Alternatively, retraction of the shield member 141 alone in a proximal direction into the housing 130 can act to activate the drive mechanism 126 and initiate the injection and/or drug delivery sequence. In this way, the autoinjector 100 has device operation prevention mechanism which prevents dispensing of the drug by, for example, preventing accidental release of the dispensing mechanism 120 and/or accidental actuation of the trigger 150.

While the foregoing description relates to one example of an autoinjector, this example is presented purely for illustration, the present invention is not limited solely to such an autoinjector. A person skilled in the art understands that various modifications to the described autoinjector can be implemented within the scope of the present disclosure.

Autoinjectors of the present disclosure can be used to administer any of a variety of drugs, such as any of epinephrine, Rebif, Enbrel, Aranesp, atropine, pralidoxime chloride, and diazepam.

Infusion Pumps

Patients can require precise, continuous delivery of medication or medication delivery on a regular or frequent basis at set periodic intervals. Infusion pumps can provide such controlled drug infusion by facilitating the administering of the drug at a precise rate that keeps the drug concentration within a therapeutic margin, without requiring frequent attention by a healthcare professional or the patient.

Figure 2:
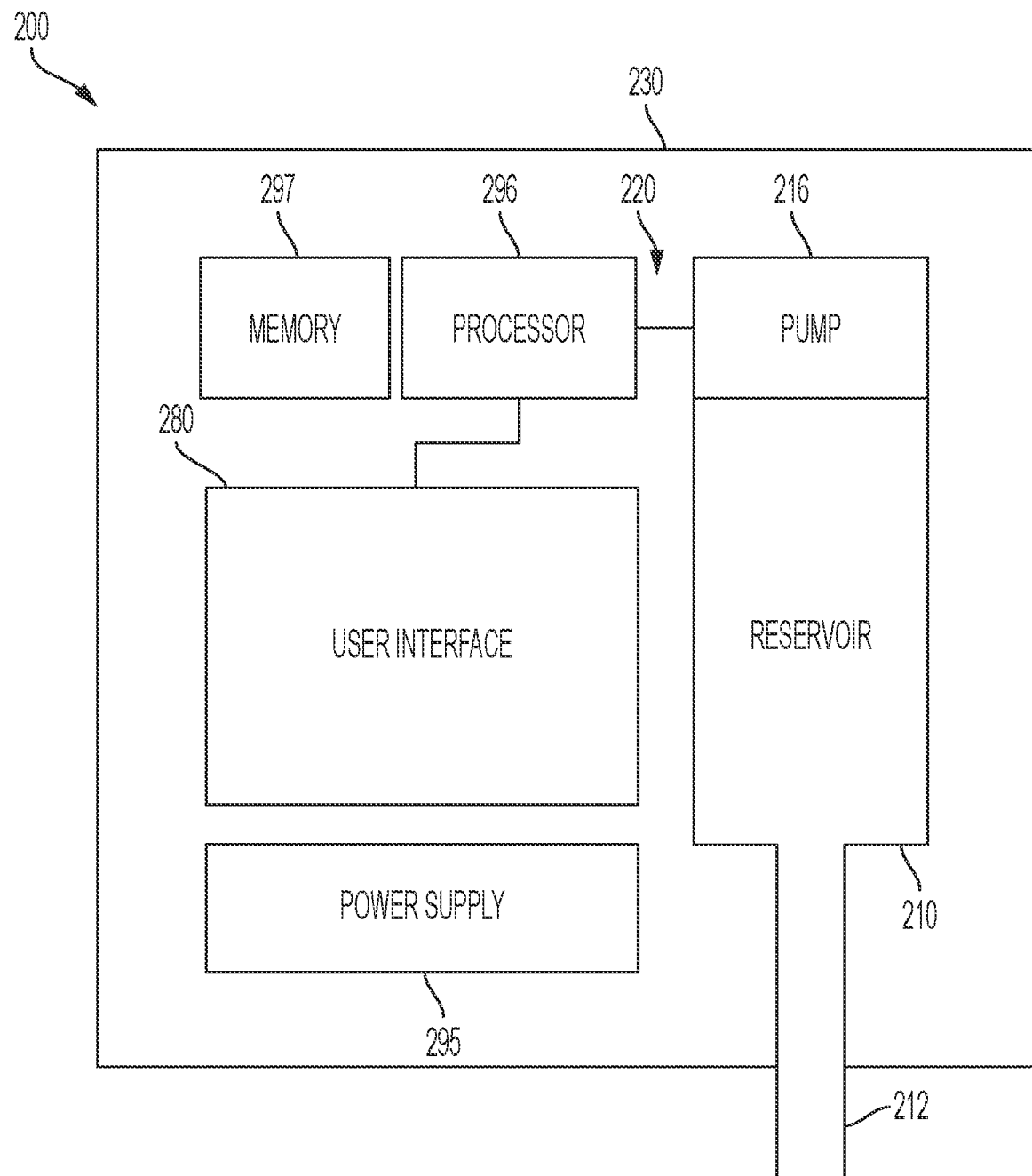
FIG. 2 is a schematic view of one embodiment of a second type of drug administration device, namely an infusion pump.

FIG. 2 is a schematic exemplary view of a second type of drug delivery device, namely an infusion pump 200, useable with the embodiments described herein. The infusion pump 200 includes a drug holder 210 (also referred to herein as a "reservoir") in the form of a reservoir for containing a drug to be delivered, and a dispensing mechanism 220 including a pump 216 configured to dispense a drug contained in the reservoir, so that the drug can be delivered to a patient. These components of the infusion pump 200 are located within a housing 230. The dispensing mechanism 220 further includes an infusion line 212. The drug is delivered from the reservoir 210 upon actuation of the pump 216 via the infusion line 212, which can take the form of a cannula. The pump 216 can take the form of an elastomeric pump, a peristaltic pump, an osmotic pump, or a motor-controlled piston in a syringe. Typically, the drug is delivered intravenously, although subcutaneous, arterial and epidural infusions can also be used.

Infusion pumps of the present disclosure can be used to administer any of a variety of drugs, such as any of insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, and zoledronic acid.

The infusion pump 200 further includes control circuitry, for example a processor 296 in addition to a memory 297 and a user interface 280, which together provide a triggering mechanism and/or dosage selector for the pump 200. The user interface 280 can be implemented by a display screen located on the housing 230 of the infusion pump 200. The control circuitry and user interface 280 can be located within the housing 230 or external thereto and can communicate via a wired or wireless interface with the pump 216 to control its operation.

Actuation of the pump 216 is controlled by the processor 296, which is in communication with the pump 216 for controlling the pump's operation. The processor 296 can be programmed by a user (e.g., patient or healthcare professional) via a user interface 280 and/or can be programmed electronically using a computer system (e.g., using a robotic surgical system configured to control operation of the pump 216). This enables the infusion pump 200 to deliver the drug to a patient in a controlled manner. The user (or computer system) can enter parameters, such as infusion duration and delivery rate. The delivery rate can be set to a constant infusion rate or as set intervals for periodic delivery, typically within pre-programmed limits. The programmed parameters for controlling the pump 216 are stored in and retrieved from the memory 297 which is in communication with the processor 296. The user interface 280 can take the form of a touch screen or a keypad.

A power supply 295 provides power to the pump 216 and can take the form of an energy source which is integral to the pump 216 and/or a mechanism for connecting the pump 216 to an external source of power.

The infusion pump 200 can take on a variety of different physical forms depending on its designated use. It can be a stationary, non-portable device, e.g., for use at a patient's bedside, in an operating room, etc., or it can be an ambulatory infusion pump which is designed to be portable or wearable. An integral power supply 295 is particularly beneficial for ambulatory infusion pumps.

While the foregoing description relates to one example of an infusion pump, this example is provided purely for illustration. The present disclosure is not limited to such an infusion pump. A person skilled in the art understands that various modifications to the described infusion pump can be implemented within the scope of the present disclosure. For example, the processor may be pre-programmed, such that it is not necessary for the infusion pump to include a user interface.

Inhalers

Figure 3:
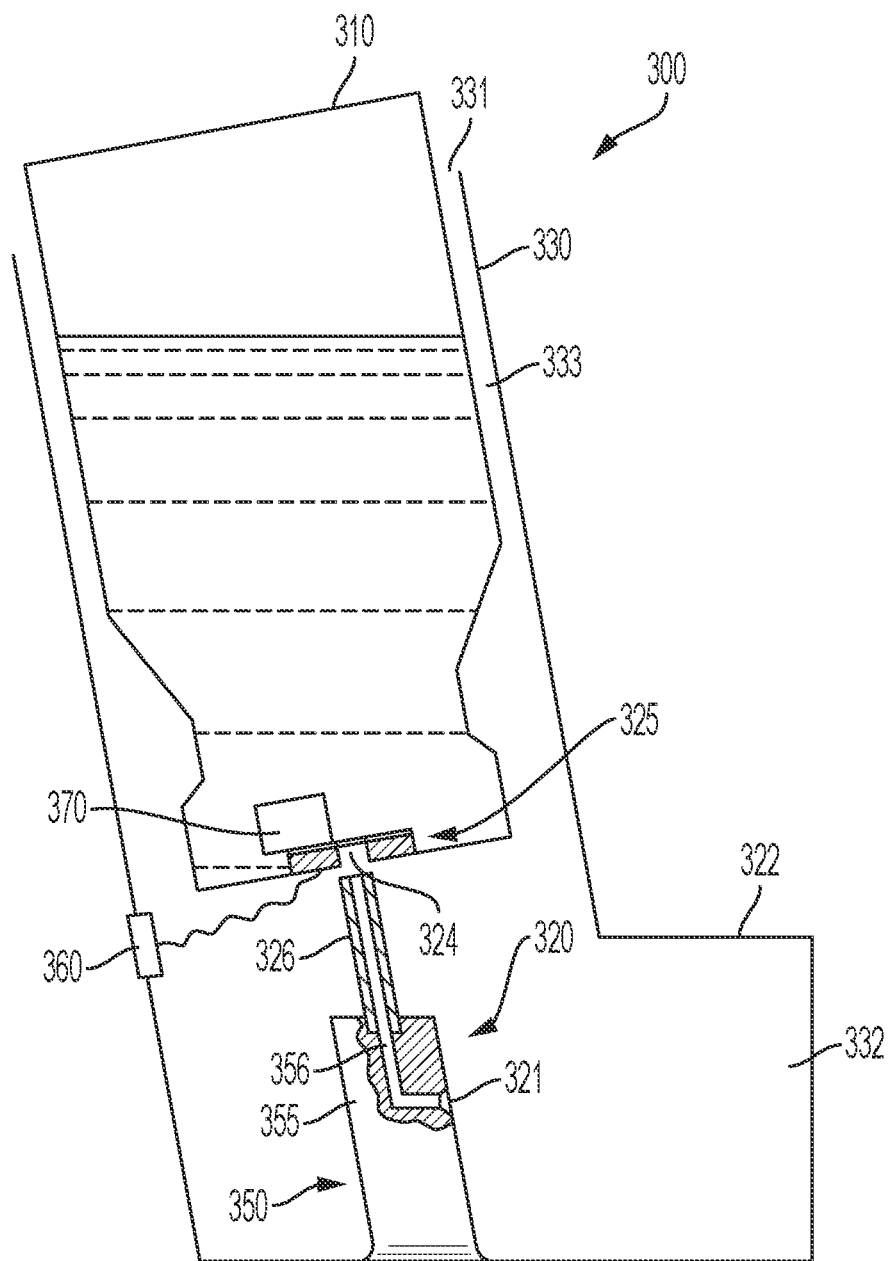
FIG. 3 is a schematic view of one embodiment of a third type of drug administration device, namely an inhaler.
Figure 4:
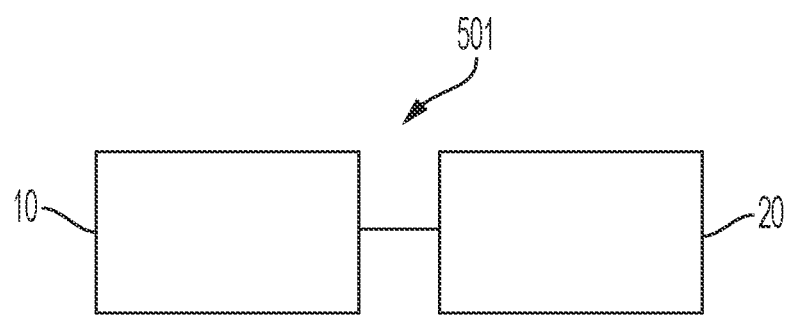
FIG. 4 is a schematic view of a general drug administration device.

FIG. 3 is a schematic view of a third type of drug administration device, namely an inhaler 300. Inhaler 300 includes a drug holder 310 in the form of a canister. The drug holder 310 contains a drug that would typically be in solution or suspension with a suitable carrier liquid. The inhaler 300 further includes a dispensing mechanism 320, which includes a pressurized gas for pressurizing the drug holder 310, a valve 325 and nozzle 321. The valve 325 forms an outlet of the drug holder 310. The valve 325 includes a narrow opening 324 formed in the drug holder 310 and a movable element 326 that controls the opening 324. When the movable element 326 is in a resting position, the valve 325 is in a closed or unactuated state in which the opening 324 is closed and the drug holder 310 is sealed. When the movable element 326 is actuated from the resting position to an actuated position, the valve 325 is actuated into an open state in which the opening 324 is open. Actuation of the movable element 326 from the resting position to the actuated position comprises moving the movable element 326 into the drug holder 310. The movable element 326 is resiliently biased into the resting position. In the open state of the valve 325, the pressurized gas propels the drug in solution or suspension with the suitable liquid out of the drug holder 310 through the opening 324 at high speed. The high speed passage of the liquid through the narrow opening 324 causes the liquid to be atomized, that is, to transform from a bulk liquid into a mist of fine droplets of liquid and/or into a gas cloud. A patient may inhale the mist of fine droplets and/or the gas cloud into a respiratory passage. Hence, the inhaler 300 is capable of delivering a drug retained within the drug holder 310 into a respiratory passage of a patient.

The drug holder 310 is removably held within a housing 330 of the inhaler 300. A passage 333 formed in the housing 330 connects a first opening 331 in the housing 330 and a second opening 332 in the housing 330. The drug holder 310 is received within the passage 333. The drug holder 310 is slidably insertable through the first opening 331 of the housing 330 into the passage 333. The second opening 332 of the housing 330 forms a mouthpiece 322 configured to be placed in a patient's mouth or a nosepiece configured to be placed in a patient's nostril, or a mask configured to be placed over the patient's mouth and nose. The drug holder 310, the first opening 331 and the passage 333 are sized such that air can flow through the passage 333, around the drug holder 310, between the first opening 331 and the second opening 332. The inhaler 300 can be provided with a dispensing mechanism protection mechanism 140 in the form of a cap (not shown) which can be fitted to the mouthpiece 322.

Inhaler 300 further includes a trigger 350 including a valve actuation feature 355 configured to actuate the valve 325 when the trigger 350 is activated. The valve actuation feature 355 is a projection of the housing 330 into the passage 333. The drug holder 310 is slidably movable within the passage 333 from a first position into a second position. In the first position, an end of the movable element 326 in the resting position abuts the valve actuation feature 355. In the second position, the drug holder 310 can be displaced towards the valve actuation feature 355 such that the valve actuation feature 355 moves the movable element 326 into the drug holder 310 to actuate the valve 325 into the open state. The user's hand (or other element handheld by a user or controlled by a robotic surgical system) provides the necessary force to move the drug holder 310 from the first position to the second position against the resiliently biased movable element 326. The valve actuation feature 355 includes an inlet 356, which is connected to the nozzle 321. The inlet 356 of the valve actuation feature 355 is sized and positioned to couple to the opening 324 of the valve 325 such that the ejected mist of droplets and/or gas cloud can enter the inlet 356 and exit from the nozzle 321 into the passage 333. The nozzle 321 assists in the atomization of the bulk liquid into the mist of droplets and/or gas cloud.

The valve 325 provides a metering mechanism 370. The metering mechanism 370 is configured to close the valve after a measured amount of liquid, and therefore, drug, has passed through the opening 324. This allows a controlled dose to be administered to the patient. Typically, the measured amount of liquid is pre-set, however, the inhaler 300 can be equipped with a dosage selector 360 that is operable by a user and/or electronically by a computer system to change the defined amount of liquid.

While the foregoing description relates to one particular example of an inhaler, this example is purely illustrative. The description should not be seen as limited only to such an inhaler. A person skilled in the art understands that numerous other types of inhalers and nebulizers may be used with the present disclosure. For example, the drug can be in a powdered form, the drug can be in liquid form, or the drug can be atomized by other forms of dispensing mechanism 320 including ultrasonic vibration, compressed gas, a vibrating mesh, or a heat source.

The inhalers of the present disclosure can be used to administer any of a variety of drugs, such as any of mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

Drug Administration Devices

As will be appreciated from the foregoing, various components of drug delivery devices are common to all such devices. These components form the essential components of a universal drug administration device. A drug administration device delivers a drug to a patient, where the drug is provided in a defined dosage form within the drug administration device.

FIG. 4 is a generalized schematic view of such a universal drug administration device 501, and FIG. 5 is an exemplary embodiment of such a universal drug administration device 500. Examples of the universal drug administration device 500 include injection devices (e.g., autoinjectors, jet injectors, and infusion pumps), nasal spray devices, and inhalers.

As shown in FIG. 4, the drug administration device 501 includes in general form the features of a drug holder 10 and a dispensing mechanism 20. The drug holder 10 holds a drug in a dosage form to be administered. The dispensing mechanism 20 is configured to release the dosage form from the drug holder 10 so that the drug can be administered to a patient.

FIG. 5 shows a further universal drug administration device 500 which includes a number of additional features. A person skilled in the art understands that these additional features are optional for different embodiments and can be utilized in a variety of different combinations such that the additional features may be present or may be omitted from a given embodiment of a particular drug administration device, depending upon requirements, such as the type of drug, dosage form of the drug, medical indication being treated with the drug, safety requirements, whether the device is powered, whether the device is portable, whether the device is used for self-administration, and many other requirements which will be appreciated by a person skilled in the art. Similar to the universal device of FIG. 4, the drug administration device 500 of FIG. 5 includes a housing 30 which accommodates the drug holder 10 and dispensing mechanism 20.

The device 500 is provided with a triggering mechanism 50 for initiating the release of the drug from the drug holder 10 by the dispensing mechanism 20. The device 500 includes the feature of a metering/dosing mechanism 70 which measures out a set dose to be released from the drug holder 10 via the dispensing mechanism 20. In this manner, the drug administration device 500 can provide a known dose of determined size. The device 500 includes a dosage selector 60 which enables a user to set the dose volume of drug to be measured out by the metering mechanism 50. The dose volume can be set to one specific value of a plurality of predefined discrete dose volumes, or any value of predefined dose volume within a range of dose volumes.

The device 500 includes a device operation prevention mechanism 40 or 25 which when in a locked state will prevent and/or stop the dispensing mechanism 20 from releasing the drug out of the drug holder 10, and when in an unlocked state will permit the dispensing mechanism 20 to release the drug dosage from out of the drug holder 10. This can prevent accidental administration of the drug, for example to prevent dosing at an incorrect time, or for preventing inadvertent actuation. The device 500 also includes a dispensing mechanism protection mechanism 42 which prevents access to at least a part of the dispensing mechanism 20, for example for safety reasons. The device operation prevention mechanism 40 and the dispensing mechanism protection mechanism 42 can be the same component.

The device 500 includes a device indicator 85 which is configured to present information about the status of the drug administration device and/or the drug contained therein. The device indicator 85 can be a visual indicator, such as a display screen, or an audio indicator. The device 500 includes a user interface 80 which can be configured to present a user of the device 500 with information about the device 500 and/or to enable the user to control the device 500. The device 500 includes a device sensor 92 which is configured to sense information relating to the drug administration device and/or the drug contained therein, for example dosage form and device parameters. As an example, in embodiments which include a metering mechanism 70 and a dosage selector 60, the embodiment can further include one or more device sensors 92 configured to sense one or more of: the dose selected by a user using dosage selector 60, the dose metered by the metering mechanism 70 and the dose dispensed by the dispensing mechanism 20. Similarly, an environment sensor 94 is provided which is configured to sense information relating to the environment in which the device 500 is present, such as the temperature of the environment, the humidity of the environment, location, and time. There can be a dedicated location sensor 98 which is configured to determine the geographical location of the device 500, e.g., via satellite position determination, such as GPS. The device 500 also includes a communications interface 99 which can communicate externally data which has been acquired from the various sensors about the device and/or drug.

If required, the device 500 includes a power supply 95 for delivering electrical power to one or more electrical components of the device 500. The power supply 95 can be a source of power which is integral to device 500 and/or a mechanism for connecting device 500 to an external source of power. The drug administration device 500 also includes a computer system 90 including a processor 96 and a memory 97 powered by the power supply 95 and in communication with each other, and optionally with other electrical and control components of the device 500, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to indicator 85 and/or to communications interface 99.

In some embodiments, the drug administration device 500 is enclosed in packaging 35. The packaging 35 can further include a combination of a processor 96, a memory 97, a user interface 80, a device indicator 85, a device sensor 92, a location sensor 98, and/or environment sensors 94 as described herein, and these can be located externally on the housing of the device 500.

A person skilled in the art will appreciate that the universal drug administration device 500 including the drug holder 10 and the dispensing mechanism 20 can be provided with a variety of the optional features described above, in a number of different combinations. Moreover, the drug administration device 500 can include more than one drug holder 10, optionally with more than one dispensing mechanism 20, such that each drug holder 10 has its own associated dispensing mechanism 20.

Drug Dosage Forms

Conventionally, drug administration devices utilize a liquid dosage form. It will be appreciated by a person skilled in the art, however, that other dosage forms are available.

One such common dosage form is a tablet. The tablet may be formed from a combination of the drug and an excipient that are compressed together. Other dosage forms are pastes, creams, powders, ear drops, and eye drops.

Further examples of drug dosage forms include dermal patches, drug eluting stents and intrauterine devices. In these examples, the body of the device includes the drug and can be configured to allow the release of the drug under certain circumstances. For example, a dermal patch may include a polymeric composition containing the drug. The polymeric composition allows the drug to diffuse out of the polymeric composition and into skin of a patient. Drug eluting stents and intrauterine devices can operate in an analogous manner. In this way, the patches, stents, and intrauterine devices can themselves be considered drug holders with an associated dispensing mechanism.

Any of these dosage forms can be configured to have the drug release initiated by certain conditions. This can allow the drug to be released at a desired time or location after the dosage form has been introduced into the patient. In particular, the drug release can be initiated by an external stimulus. Moreover, these dosage forms can be contained prior to administration in a housing, which can be in the form of packaging. This housing can contain some of the optional features described above which are utilized with the universal drug administration device 500.

The drug administered by the drug administration devices of the present disclosure can be any substance that causes a change in an organism's physiology or psychology when consumed. Examples of drugs that the drug administration devices of the present disclosure can administer include 5-alpha-reductase inhibitors, 5-aminosalicylates, 5HT3 receptor antagonists, ACE inhibitors with calcium channel blocking agents, ACE inhibitors with thiazides, adamantane antivirals, adrenal cortical steroids, adrenal corticosteroid inhibitors, adrenergic bronchodilators, agents for hypertensive emergencies, agents for pulmonary hypertension, aldosterone receptor antagonists, alkylating agents, allergenics, alpha-glucosidase inhibitors, alternative medicines, amebicides, aminoglycosides, aminopenicillins, aminosalicylates, AMPA receptor antagonists, amylin analogs, analgesic combinations, analgesics, androgens and anabolic steroids, Angiotensin Converting Enzyme Inhibitors, angiotensin II inhibitors with calcium channel blockers, angiotensin II inhibitors with thiazides, angiotensin receptor blockers, angiotensin receptor blockers and neprilysin inhibitors, anorectal preparations, anorexiants, antacids, anthelmintics, anti-angiogenic ophthalmic agents, anti-CTLA-4 monoclonal antibodies, anti-infectives, anti-PD-1 monoclonal antibodies, antiadrenergic agents (central) with thiazides, antiadrenergic agents (peripheral) with thiazides, antiadrenergic agents, centrally acting, antiadrenergic agents, peripherally acting, antiandrogens, antianginal agents, antiarrhythmic agents, antiasthmatic combinations, antibiotics/antineoplastics, anticholinergic antiemetics, anticholinergic antiparkinson agents, anticholinergic bronchodilators, anticholinergic chronotropic agents, anticholinergics/antispasmodics, anticoagulant reversal agents, anticoagulants, anticonvulsants, antidepressants, antidiabetic agents, antidiabetic combinations, antidiarrheals, antidiuretic hormones, antidotes, antiemetic/antivertigo agents, antifungals, antigonadotropic agents, antigout agents, antihistamines, antihyperlipidemic agents, antihyperlipidemic combinations, antihypertensive combinations, antihyperuricemic agents, antimalarial agents, antimalarial combinations, antimalarial quinolones, antimanic agents, antimetabolites, antimigraine agents, antineoplastic combinations, antineoplastic detoxifying agents, antineoplastic interferons, antineoplastics, antiparkinson agents, antiplatelet agents, antipseudomonal penicillins, antipsoriatics, antipsychotics, antirheumatics, antiseptic and germicides, antithyroid agents, antitoxins and antivenins, antituberculosis agents, antituberculosis combinations, antitussives, antiviral agents, antiviral boosters, antiviral combinations, antiviral interferons, anxiolytics, sedatives, and hypnotics, aromatase inhibitors, atypical antipsychotics, azole antifungals, bacterial vaccines, barbiturate anticonvulsants, barbiturates, BCR-ABL tyrosine kinase inhibitors, benzodiazepine anticonvulsants, benzodiazepines, beta blockers with calcium channel blockers, beta blockers with thiazides, beta-adrenergic blocking agents, beta-lactamase inhibitors, bile acid sequestrants, biologicals, bisphosphonates, bone morphogenetic proteins, bone resorption inhibitors, bronchodilator combinations, bronchodilators, calcimimetics, calcineurin inhibitors, calcitonin, calcium channel blocking agents, carbamate anticonvulsants, carbapenems, carbapenems/beta-lactamase inhibitors, carbonic anhydrase inhibitor anticonvulsants, carbonic anhydrase inhibitors, cardiac stressing agents, cardioselective beta blockers, cardiovascular agents, catecholamines, cation exchange resins, CD20 monoclonal antibodies, CD30 monoclonal antibodies, CD33 monoclonal antibodies, CD38 monoclonal antibodies, CD52 monoclonal antibodies, CDK 4/6 inhibitors, central nervous system agents, cephalosporins, cephalosporins/beta-lactamase inhibitors, cerumenolytics, CFTR combinations, CFTR potentiators, CGRP inhibitors, chelating agents, chemokine receptor antagonist, chloride channel activators, cholesterol absorption inhibitors, cholinergic agonists, cholinergic muscle stimulants, cholinesterase inhibitors, CNS stimulants, coagulation modifiers, colony stimulating factors, contraceptives, corticotropin, coumarins and indandiones, cox-2 inhibitors, decongestants, dermatological agents, diagnostic radiopharmaceuticals, diarylquinolines, dibenzazepine anticonvulsants, digestive enzymes, dipeptidyl peptidase 4 inhibitors, diuretics, dopaminergic antiparkinsonism agents, drugs used in alcohol dependence, echinocandins, EGFR inhibitors, estrogen receptor antagonists, estrogens, expectorants, factor Xa inhibitors, fatty acid derivative anticonvulsants, fibric acid derivatives, first generation cephalosporins, fourth generation cephalosporins, functional bowel disorder agents, gallstone solubilizing agents, gamma-aminobutyric acid analogs, gamma-aminobutyric acid reuptake inhibitors, gastrointestinal agents, general anesthetics, genitourinary tract agents, GI stimulants, glucocorticoids, glucose elevating agents, glycopeptide antibiotics, glycoprotein platelet inhibitors, glycylcyclines, gonadotropin releasing hormones, gonadotropin-releasing hormone antagonists, gonadotropins, group I antiarrhythmics, group II antiarrhythmics, group III antiarrhythmics, group IV antiarrhythmics, group V antiarrhythmics, growth hormone receptor blockers, growth hormones, guanylate cyclase-C agonists, *H. pylori* eradication agents, H2 antagonists, hedgehog pathway inhibitors, hematopoietic stem cell mobilizer, heparin antagonists, heparins, HER2 inhibitors, herbal products, histone deacetylase inhibitors, hormones, hormones/antineoplastics, hydantoin anticonvulsants, hydrazide derivatives, illicit (street) drugs, immune globulins, immunologic agents, immunostimulants, immunosuppressive agents, impotence agents, in vivo diagnostic biologicals, incretin mimetics, inhaled anti-infectives, inhaled corticosteroids, inotropic agents, insulin, insulin-like growth factors, integrase strand transfer inhibitor, interferons, interleukin inhibitors, interleukins, intravenous nutritional products, iodinated contrast media, ionic iodinated contrast media, iron products, ketolides, laxatives, leprostatics, leukotriene modifiers, lincomycin derivatives, local injectable anesthetics, local injectable anesthetics with corticosteroids, loop diuretics, lung surfactants, lymphatic staining agents, lysosomal enzymes, macrolide derivatives, macrolides, magnetic resonance imaging contrast media, mast cell stabilizers, medical gas, meglitinides, metabolic agents, methylxanthines, mineralocorticoids, minerals and electrolytes, miscellaneous agents, miscellaneous analgesics, miscellaneous antibiotics, miscellaneous anticonvulsants, miscellaneous antidepressants, miscellaneous antidiabetic agents, miscellaneous antiemetics, miscellaneous antifungals, miscellaneous antihyperlipidemic agents, miscellaneous antihypertensive combinations, miscellaneous antimalarials, miscellaneous antineoplastics, miscellaneous antiparkinson agents, miscellaneous antipsychotic agents, miscellaneous antituberculosis agents, miscellaneous antivirals, miscellaneous anxiolytics, sedatives and hypnotics, miscellaneous bone resorption inhibitors, miscellaneous cardiovascular agents, miscellaneous central nervous system agents, miscellaneous coagulation modifiers, miscellaneous diagnostic dyes, miscellaneous diuretics, miscellaneous genitourinary tract agents, miscellaneous GI agents, miscellaneous hormones, miscellaneous metabolic agents, miscellaneous ophthalmic agents, miscellaneous otic agents, miscellaneous respiratory agents, miscellaneous sex hormones, miscellaneous topical agents, miscellaneous uncategorized agents, miscellaneous vaginal agents, mitotic inhibitors, monoamine oxidase inhibitors, mouth and throat products, mTOR inhibitors, mucolytics, multikinase inhibitors, muscle relaxants, mydriatics, narcotic analgesic combinations, narcotic analgesics, nasal anti-infectives, nasal antihistamines and decongestants, nasal lubricants and irrigations, nasal preparations, nasal steroids, natural penicillins, neprilysin inhibitors, neuraminidase inhibitors, neuromuscular blocking agents, neuronal potassium channel openers, next generation cephalosporins, nicotinic acid derivatives, NK1 receptor antagonists, NNRTIs, non-cardioselective beta blockers, non-iodinated contrast media, non-ionic iodinated contrast media, non-sulfonylureas, Nonsteroidal anti-inflammatory drugs, NS5A inhibitors, nucleoside reverse transcriptase inhibitors (NRTIs), nutraceutical products, nutritional products, ophthalmic anesthetics, ophthalmic anti-infectives, ophthalmic anti-inflammatory agents, ophthalmic antihistamines and decongestants, ophthalmic diagnostic agents, ophthalmic glaucoma agents, ophthalmic lubricants and irrigations, ophthalmic preparations, ophthalmic steroids, ophthalmic steroids with anti-infectives, ophthalmic surgical agents, oral nutritional supplements, other immunostimulants, other immunosuppressants, otic anesthetics, otic anti-infectives, otic preparations, otic steroids, otic steroids with anti-infectives, oxazolidinedione anticonvulsants, oxazolidinone antibiotics, parathyroid hormone and analogs, PARP inhibitors, PCS K9 inhibitors, penicillinase resistant penicillins, penicillins, peripheral opioid receptor antagonists, peripheral opioid receptor mixed agonists/antagonists, peripheral vasodilators, peripherally acting antiobesity agents, phenothiazine antiemetics, phenothiazine antipsychotics, phenylpiperazine antidepressants, phosphate binders, PI3K inhibitors, plasma expanders, platelet aggregation inhibitors, platelet-stimulating agents, polyenes, potassium sparing diuretics with thiazides, potassium-sparing diuretics, probiotics, progesterone receptor modulators, progestins, prolactin inhibitors, prostaglandin D2 antagonists, protease inhibitors, protease-activated receptor-1 antagonists, proteasome inhibitors, proton pump inhibitors, psoralens, psychotherapeutic agents, psychotherapeutic combinations, purine nucleosides, pyrrolidine anticonvulsants, quinolones, radiocontrast agents, radiologic adjuncts, radiologic agents, radiologic conjugating agents, radiopharmaceuticals, recombinant human erythropoietins, renin inhibitors, respiratory agents, respiratory inhalant products, rifamycin derivatives, salicylates, sclerosing agents, second generation cephalosporins, selective estrogen receptor modulators, selective immunosuppressants, selective phosphodiesterase-4 inhibitors, selective serotonin reuptake inhibitors, serotonin-norepinephrine reuptake inhibitors, serotoninergic neuroenteric modulators, sex hormone combinations, sex hormones, SGLT-2 inhibitors, skeletal muscle relaxant combinations, skeletal muscle relaxants, smoking cessation agents, somatostatin and somatostatin analogs, spermicides, statins, sterile irrigating solutions, streptogramins, *streptomyces* derivatives, succinimide anticonvulsants, sulfonamides, sulfonylureas, synthetic ovulation stimulants, tetracyclic antidepressants, tetracyclines, therapeutic radiopharmaceuticals, therapeutic vaccines, thiazide diuretics, thiazolidinediones, thioxanthenes, third generation cephalosporins, thrombin inhibitors, thrombolytics, thyroid drugs, TNF alfa inhibitors, tocolytic agents, topical acne agents, topical agents, topical allergy diagnostic agents, topical anesthetics, topical anti-infectives, topical anti-rosacea agents, topical antibiotics, topical antifungals, topical antihistamines, topical antineoplastics, topical antipsoriatics, topical antivirals, topical astringents, topical debriding agents, topical depigmenting agents, topical emollients, topical keratolytics, topical non-steroidal anti-inflammatories, topical photochemotherapeutics, topical rubefacient, topical steroids, topical steroids with anti-infectives, transthyretin stabilizers, triazine anticonvulsants, tricyclic antidepressants, trifunctional monoclonal antibodies, ultrasound contrast media, upper respiratory combinations, urea anticonvulsants, urea cycle disorder agents, urinary anti-infectives, urinary antispasmodics, urinary pH modifiers, uterotonic agents, vaccine combinations, vaginal anti-infectives, vaginal preparations, vasodilators, vasopressin antagonists, vasopressors, VEGF/VEGFR inhibitors, viral vaccines, viscosupplementation agents, vitamin and mineral combinations, vitamins, or VMAT2 inhibitors. The drug administration devices of the present disclosure may administer a drug selected from epinephrine, Rebif, Enbrel, Aranesp, atropine, pralidoxime chloride, diazepam, insulin, antropine sulfate, avibactam sodium, bendamustine hydrochloride, carboplatin, daptomycin, epinephrine, levetiracetam, oxaliplatin, paclitaxel, pantoprazole sodium, treprostinil, vasopressin, voriconazole, zoledronic acid, mometasone, fluticasone, ciclesonide, budesonide, beclomethasone, vilanterol, salmeterol, formoterol, umeclidinium, glycopyrrolate, tiotropium, aclidinium, indacaterol, salmeterol, and olodaterol.

As mentioned above, any of a variety of drugs can be delivered using a drug administration device.

Drug Housings

As described above, a dosage form can be provided in a holder that is appropriate for the particular dosage form being utilized. For example, a drug in a liquid dosage form can be held prior to administration within a holder in the form of a vial with a stopper, or a syringe with a plunger. A drug in solid or powder dosage form, e.g., as tablets, can be contained in a housing which is arranged to hold the tablets securely prior to administration.

The housing can include one or a plurality of drug holders, where each holder contains a dosage form, e.g., the drug can be in a tablet dosage form and the housing can be in the form of a blister pack, where a tablet is held within each of a plurality of holders. The holders being in the form of recesses in the blister pack.

Figure 6:
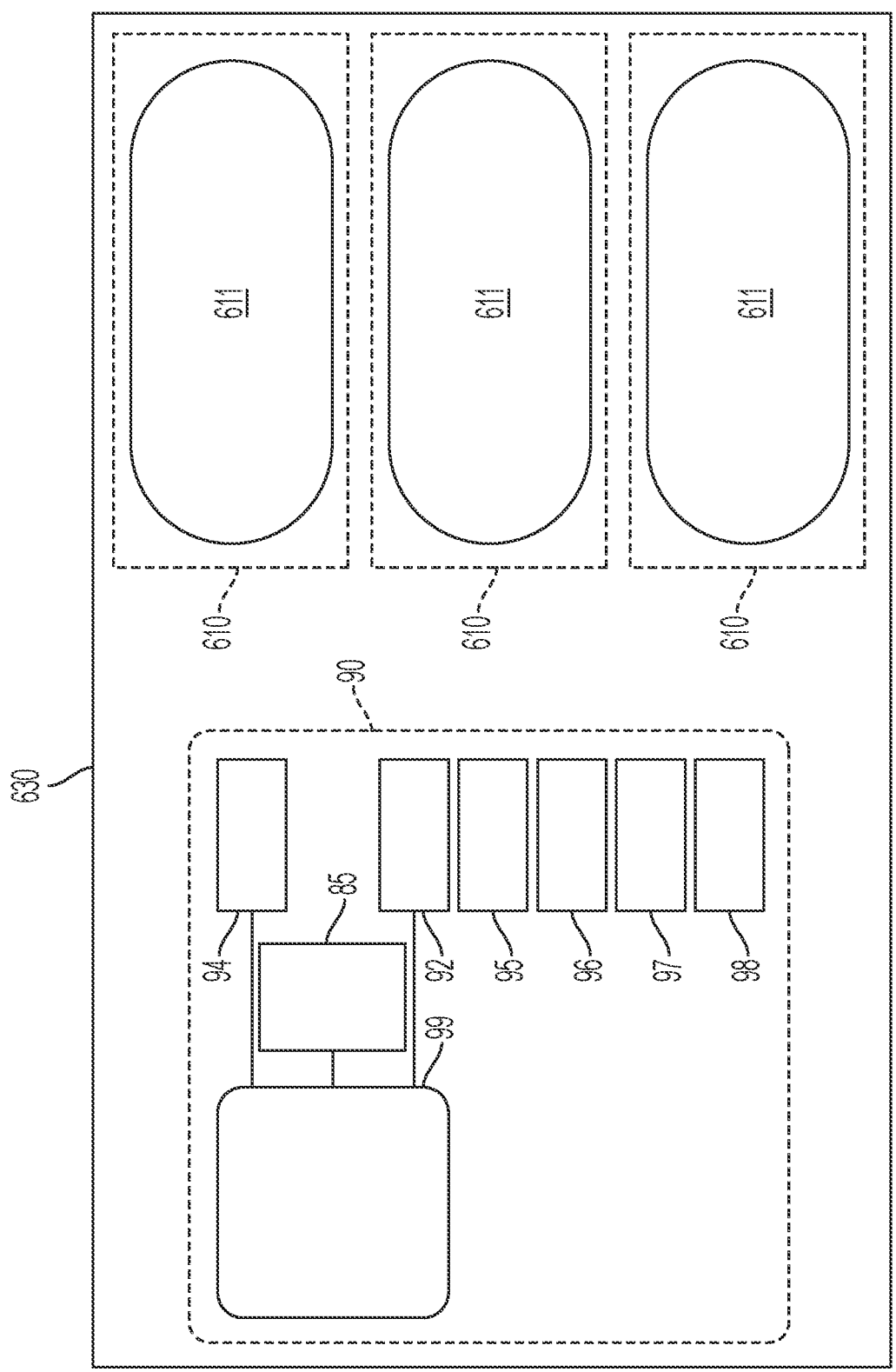
FIG. 6 is a schematic view of one embodiment of a housing for a dosage form.

FIG. 6 depicts a housing 630 that includes a plurality of drug holders 610 that each contain a dosage form 611. The housing 630 can have at least one environment sensor 94, which is configured to sense information relating to the environment in which the housing 630 is present, such as the temperature of the environment, time or location. The housing 630 can include at least one device sensor 92, which is configured to sense information relating to the drug of the dosage form 611 contained within the holder 610. There can be a dedicated location sensor 98 which is configured to determine the geographical location of the housing 630, e.g., via satellite position determination, such as GPS.

The housing 630 can include an indicator 85 which is configured to present information about the status of the drug of the dosage form 611 contained within the holder 610 to a user of the drug housing. The housing 630 can also include a communications interface 99 which can communicate information externally via a wired or wireless transfer of data pertaining to the drug housing 630, environment, time, or location and/or the drug itself.

If required, the housing 630 can include a power supply 95 for delivering electrical power to one or more electrical components of the housing 630. The power supply 95 can be a source of power which is integral to housing 630 and/or a mechanism for connecting the housing 630 to an external source of power. The housing 630 can also include a computer system 90 including a processor 96 and a memory 97 powered by the power supply 95 and in communication with each other, and optionally with other electrical and control components of the housing 630, such as the environment sensor 94, the location sensor 98, the device sensor 92, the communications interface 99, and/or the indicator 85. The processor 96 is configured to obtain data acquired from the environment sensor 94, the device sensor 92, the communications interface 99, the location sensor 98, and/or the user interface 80 and process it to provide data output, for example to the indicator 85 and/or to the communications interface 99.

The housing 630 can be in the form of packaging. Alternatively, additional packaging can be present to contain and surround the housing 630.

The holder 610 or the additional packaging the themselves include one or more of the device sensor 92, the environment sensor 94, the indicator 85, the communications interface 99, the power supply 95, location sensor 98, and the computer system including the processor 96 and the memory 85, as described above.

Electronic Communication

Figure 7:
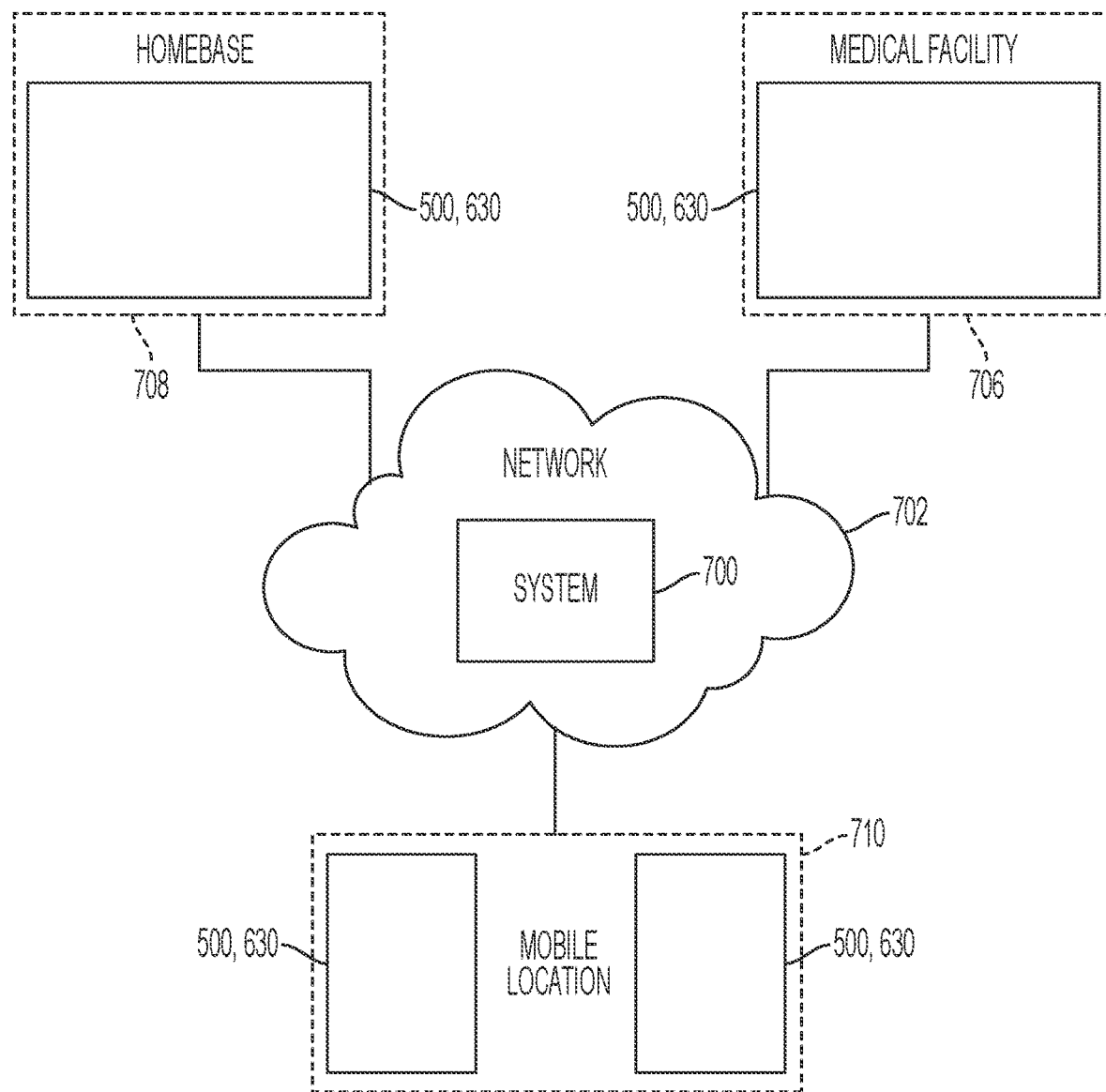
FIG. 7 is a schematic view of one embodiment of a communication network system with which the drug administration devices and housing can operate.

As mentioned above, the communications interface 99 can be associated with the drug administration device 500 or the drug housing 630, by being included within or on the housing 30, 630, or alternatively within or on the packaging 35. Such a communications interface 99 can be configured to communicate with a remote computer system, such as central computer system 700 shown in FIG. 7. As shown in FIG. 7, the communications interface 99 associated with the drug administration device 500 or the housing 630 is configured to communicate with a central computer system 700 through a communications network 702 from any number of locations such as a medical facility 706 (e.g., a hospital or other medical care center), a home base 708 (e.g., a patient's home or office or a care taker's home or office), or a mobile location 710. The communications interface 99 can be configured to access the system 700 through a wired and/or wireless connection to the network 702. In an exemplary embodiment, the communications interface 99 of FIG. 6 is configured to access the system 700 wirelessly, e.g., through Wi-Fi connection(s), which can facilitate accessibility of the system 700 from almost any location in the world.

A person skilled in the art will appreciate that the system 700 can include security features such that the aspects of the system 700 available to any particular user can be determined based on, e.g., the identity of the user and/or the location from which the user is accessing the system. To that end, each user can have a unique username, password, biometric data, and/or other security credentials to facilitate access to the system 700. The received security parameter information can be checked against a database of authorized users to determine whether the user is authorized and to what extent the user is permitted to interact with the system, view information stored in the system, and so forth.

Computer Systems

As discussed herein, one or more aspects or features of the subject matter described herein, for example components of the central computer system 700, the processor 96, the power supply 95, the memory 97, the communications interface 99, the user interface 80, the device indicators 85, the device sensors 92, the environment sensors 94, and the location sensors 98, can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computer system can include clients and servers. A client and server are generally remote from each other and typically interact through a communications network, e.g., the Internet, a wireless wide area network, a local area network, a wide area network, or a wired network. The relationship of client and server arises by virtue of computer programs running on the respective computers and having a client-server relationship to each other.

The computer programs, which can also be referred to as programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" as used herein refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein, for example the user interface 80 (which can be integrated or separate to the administration device 500 or the housing 630), can be implemented on a computer having a display screen, such as for example a cathode ray tube (CRT) or a liquid crystal display (LCD) or a light emitting diode (LED) monitor for displaying information to the user. The display screen can allow input thereto directly (e.g., as a touch screen) or indirectly (e.g., via an input device such as a keypad or voice recognition hardware and software). Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. As described above, this feedback may be provided via one or more device indicators 85 in addition to the user interface 80. The device indicators 85 can interact with one or more of the device sensor(s) 92, the environment sensor(s) 94, and/or the location sensor(s) 98 in order to provide this feedback, or to receive input from the user.

Figure 8:
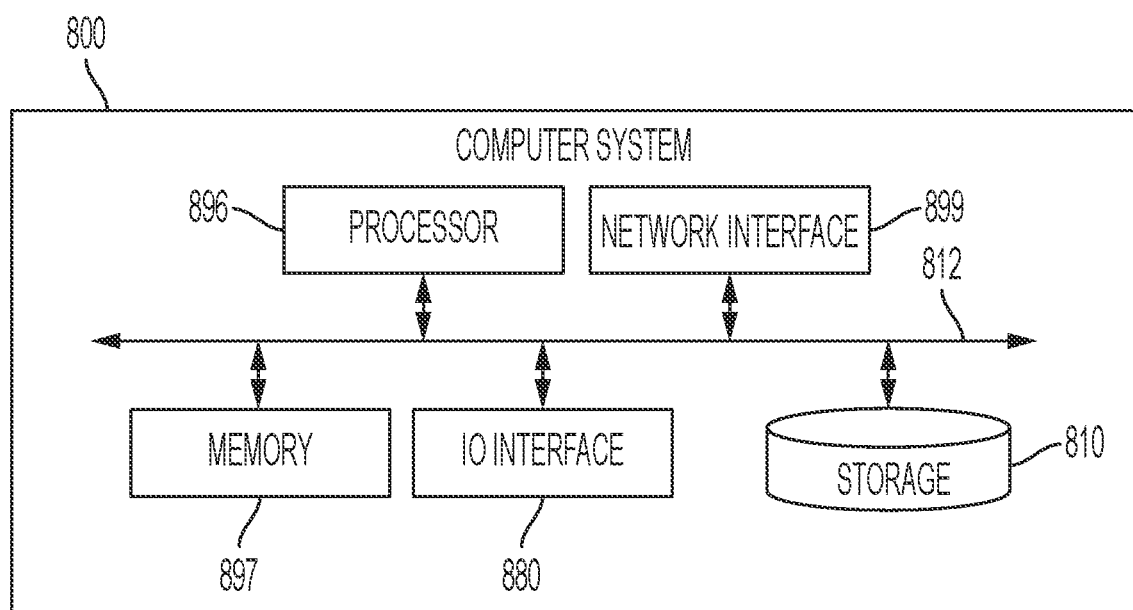
FIG. 8 is a schematic view of one embodiment of a computer system with which the drug administration devices and housing can operate.

FIG. 8 illustrates one exemplary embodiment of the computer system 700, depicted as computer system 800. The computer system includes one or more processors 896 configured to control the operation of the computer system 800. The processor(s) 896 can include any type of microprocessor or central processing unit (CPU), including programmable general-purpose or special-purpose microprocessors and/or any one of a variety of proprietary or commercially available single or multi-processor systems. The computer system 800 also includes one or more memories 897 configured to provide temporary storage for code to be executed by the processor(s) 896 or for data acquired from one or more users, storage devices, and/or databases. The memory 897 can include read-only memory (ROM), flash memory, one or more varieties of random access memory (RAM) (e.g., static RAM (SRAM), dynamic RAM (DRAM), or synchronous DRAM (SDRAM)), and/or a combination of memory technologies.

The various elements of the computer system are coupled to a bus system 812. The illustrated bus system 812 is an abstraction that represents any one or more separate physical busses, communication lines/interfaces, and/or multi-drop or point-to-point connections, connected by appropriate bridges, adapters, and/or controllers. The computer system 800 also includes one or more network interface(s) 899 (also referred to herein as a communications interface), one or more input/output (IO) interface(s) 880, and one or more storage device(s) 810.

The communications interface(s) 899 are configured to enable the computer system to communicate with remote devices, e.g., other computer systems and/or devices 500 or housings 630, over a network, and can be, for example, remote desktop connection interfaces, Ethernet adapters, and/or other local area network (LAN) adapters. The IO interface(s) 880 include one or more interface components to connect the computer system 800 with other electronic equipment. For example, the IO interface(s) 880 can include high speed data ports, such as universal serial bus (USB) ports, 1394 ports, Wi-Fi, Bluetooth, etc. Additionally, the computer system 800 can be accessible to a human user, and thus the IO interface(s) 880 can include displays, speakers, keyboards, pointing devices, and/or various other video, audio, or alphanumeric interfaces. The storage device(s) 810 include any conventional medium for storing data in a non-volatile and/or non-transient manner. The storage device(s) 810 are thus configured to hold data and/or instructions in a persistent state in which the value(s) are retained despite interruption of power to the computer system. The storage device(s) 810 can include one or more hard disk drives, flash drives, USB drives, optical drives, various media cards, diskettes, compact discs, and/or any combination thereof and can be directly connected to the computer system or remotely connected thereto, such as over a network. In an exemplary embodiment, the storage device(s) 810 include a tangible or non-transitory computer readable medium configured to store data, e.g., a hard disk drive, a flash drive, a USB drive, an optical drive, a media card, a diskette, or a compact disc.

The elements illustrated in FIG. 8 can be some or all of the elements of a single physical machine. In addition, not all of the illustrated elements need to be located on or in the same physical machine.

The computer system 800 can include a web browser for retrieving web pages or other markup language streams, presenting those pages and/or streams (visually, aurally, or otherwise), executing scripts, controls and other code on those pages/streams, accepting user input with respect to those pages/streams (e.g., for purposes of completing input fields), issuing HyperText Transfer Protocol (HTTP) requests with respect to those pages/streams or otherwise (e.g., for submitting to a server information from the completed input fields), and so forth. The web pages or other markup language can be in HyperText Markup Language (HTML) or other conventional forms, including embedded Extensible Markup Language (XML), scripts, controls, and so forth. The computer system 800 can also include a web server for generating and/or delivering the web pages to client computer systems.

As shown in FIG. 7, the computer system 800 of FIG. 8 as described above may form the components of the central computer system 700 which is in communication with one or more of the device computer systems 90 of the one or more individual drug administration devices 500 or housings 630 and/or in communication with one or more other elements, such as one or more surgical instruments. Data, such as operational data of the devices 500 or housings 630, medical data acquired of patients by such devices 500 or housings 630, operational data of the surgical instruments, medical data acquired of patients by such surgical instruments, can be exchanged between the central and device computer systems 700, 90.

As mentioned the computer system 800 as described above can also form the components of a device computer system 90 which is integrated into or in close proximity to the drug administration device 500 or housing 630. In this regard, the one or more processors 896 correspond to the processor 96, the network interface 799 corresponds to the communications interface 99, the IO interface 880 corresponds to the user interface 80, and the memory 897 corresponds to the memory 97. Moreover, the additional storage 810 can also be present in device computer system 90.

In an exemplary embodiment, the computer system 800 can form the device computer system 90 as a single unit, e.g., contained within a single drug administration device housing 30, contained within a single package 35 for one or more drug administration devices 500, or a housing 630 that includes a plurality of drug holders 610. The computer system 800 can form the central computer system 700 as a single unit, as a single server, or as a single tower.

The single unit can be modular such that various aspects thereof can be swapped in and out as needed for, e.g., upgrade, replacement, maintenance, etc., without interrupting functionality of any other aspects of the system. The single unit can thus also be scalable with the ability to be added to as additional modules and/or additional functionality of existing modules are desired and/or improved upon.

The computer system can also include any of a variety of other software and/or hardware components, including by way of example, operating systems and database management systems. Although an exemplary computer system is depicted and described herein, it will be appreciated by a person skilled in the art that this is for sake of generality and convenience. In other embodiments, the computer system may differ in architecture and operation from that shown and described here. For example, the memory 897 and the storage device 810 can be integrated together, or the communications interface 899 can be omitted if communication with another computer system is not necessary.

Surgical Hubs

In an exemplary embodiment, the computer system to which data regarding drug administration devices and/or surgical instruments is communicated includes a surgical hub. Exemplary examples of surgical hubs configured to receive, analyze, and output data, and methods of using such surgical hubs, are further described in U.S. Pat. Pub. No. 2019/0200844 entitled "Method Of Hub Communication, Processing, Storage And Display" filed Dec. 4, 2018 and U.S. Pat. Pub. No. 2019/0201114 entitled "Adaptive Control Program Updates For Surgical Hubs" filed Mar. 29, 2018, which are hereby incorporated by reference in their entireties.

In general, a surgical hub can be a component of a comprehensive digital medical system capable of spanning multiple medical facilities and configured to provide integrated and comprehensive improved medical care to a vast number of patients. The comprehensive digital medical system includes a cloud-based medical analytics system that is configured to interconnect to multiple surgical hubs located across many different medical facilities. The surgical hubs are configured to interconnect with one or more elements, such as one or more surgical instruments that are used to conduct medical procedures on patients and/or one or more drug administration device that are used to administer one or more drugs to patients during performance of medical procedures. The surgical hubs provide a wide array of functionality to improve the outcomes of medical procedures. The data generated by the various surgical devices, drug administration devices, and surgical hubs about the patient and the medical procedure may be transmitted to the cloud-based medical analytics system. This data may then be aggregated with similar data gathered from many other surgical hubs, drug administration devices, and surgical instruments located at other medical facilities. Various patterns and correlations may be found through the cloud-based analytics system analyzing the collected data. Improvements in the techniques used to generate the data may be generated as a result, and these improvements may then be disseminated to the various surgical hubs, drug administration devices, and surgical instruments. Due to the interconnectedness of all of the aforementioned components, improvements in medical procedures and practices may be found that otherwise may not be found if the many components were not so interconnected. Various examples of structures and functions of these various components are described in more detail in previously mentioned U.S. Pat. Pub. No. 2019/0200844 entitled "Method Of Hub Communication, Processing, Storage And Display" filed Dec. 4, 2018 and U.S. Pat. Pub. No. 2019/0201114 entitled "Adaptive Control Program Updates For Surgical Hubs" filed Mar. 29, 2018.

Figure 9:
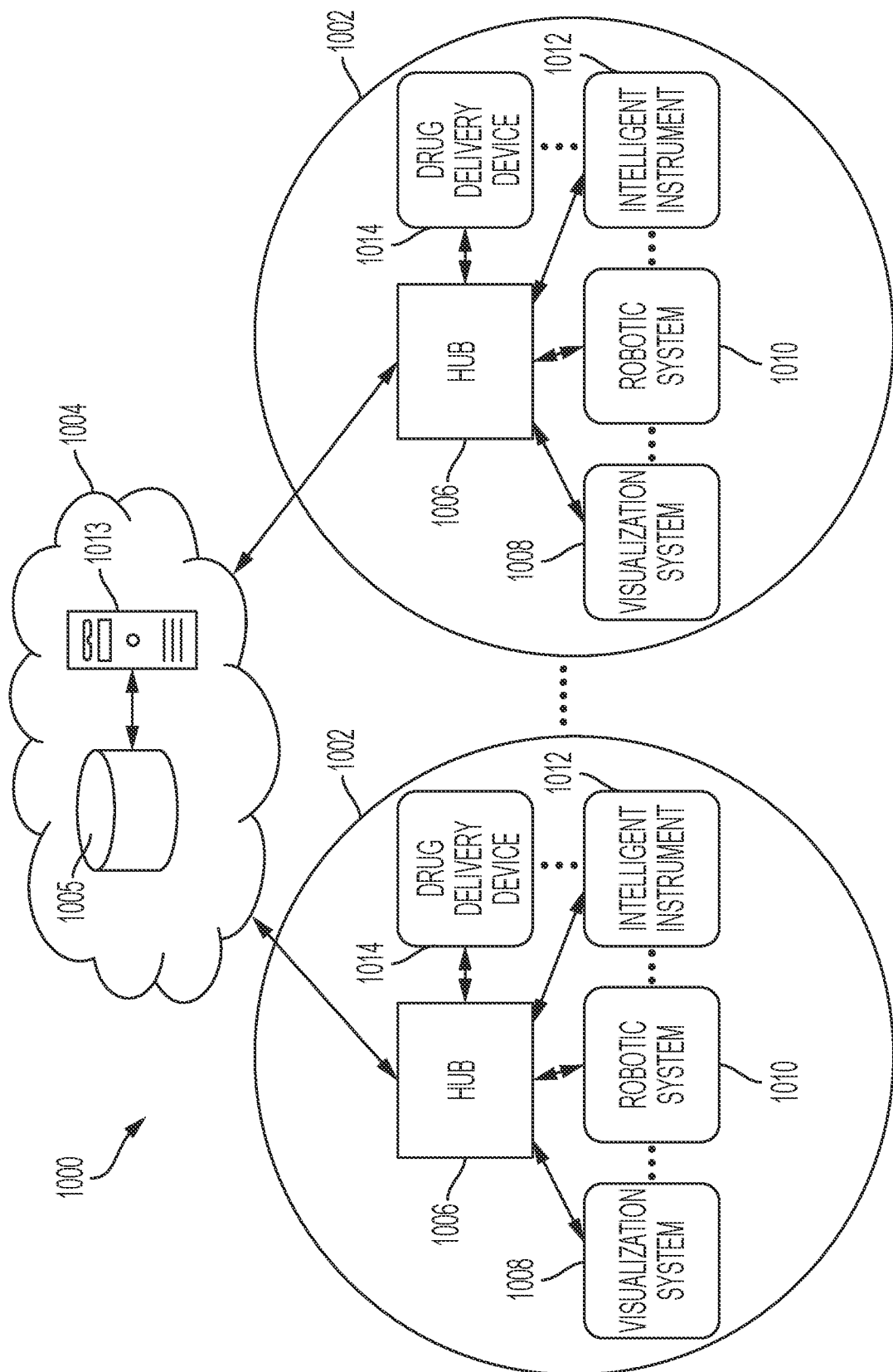
FIG. 9 is a schematic view of one embodiment of a computer-implemented interactive surgical system.

FIG. 9 illustrates an embodiment of a computer-implemented interactive surgical system 1000 that includes one or more surgical systems 1002 and a cloud-based system (e.g., a cloud 1004 that can include a remote server 1013 coupled to a storage device 1005). Each surgical system 1002 includes at least one surgical hub 1006 in communication with the cloud 1004. In one example, as illustrated in FIG. 9, the surgical system 1002 includes a visualization system 1008, a robotic system 1010, a handheld intelligent surgical instrument 1012, and a drug delivery device 1014, which are configured to communicate with one another and/or the hub 1006. The surgical system 1002 can include an M number of hubs 1006, an N number of visualization systems 1008, an O number of robotic systems 1010, a P number of handheld intelligent surgical instruments 1012, and a Q number of drug delivery devices 1014, where M, N, O, P, and Q are integers greater than or equal to one that may or may not be equal to any one or more of each other. Various exemplary drug delivery devices are described above. Various exemplary examples of suitable robotic systems, visualization systems, cloud-based analytics, and surgical instruments that can be used in a computer-implemented interactive surgical system are further described in previously mentioned U.S. Pat. Pub. No. 2019/0200844 entitled "Method Of Hub Communication, Processing, Storage And Display" filed Dec. 4, 2018 and U.S. Pat. Pub. No. 2019/0201114 entitled "Adaptive Control Program Updates For Surgical Hubs" filed Mar. 29, 2018.

Figure 10:
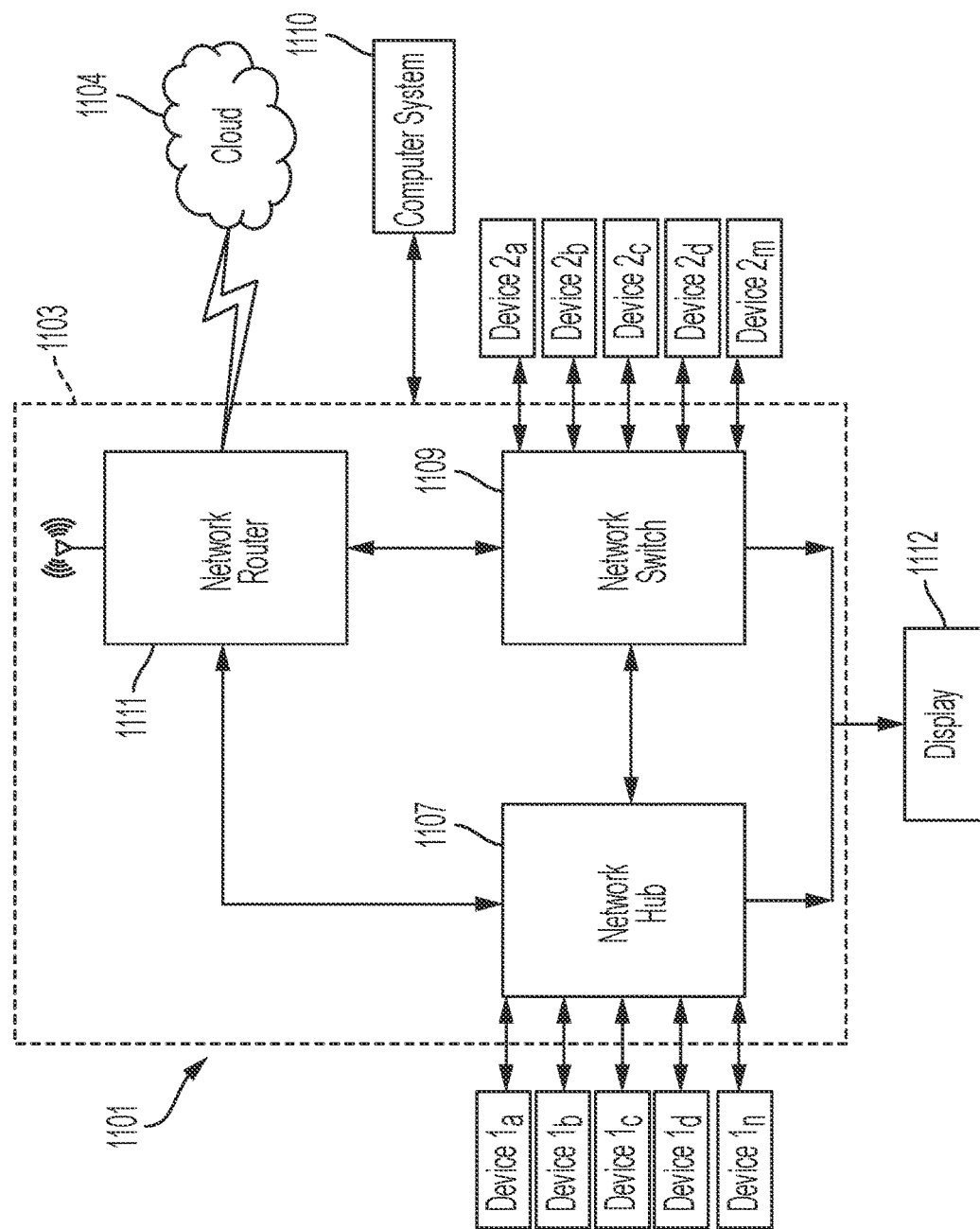
FIG. 10 is a schematic view of one embodiment of a surgical data network.

FIG. 10 illustrates one example of a surgical data network 1101 including a modular communication hub 1103, e.g., the hub 1006, configured to connect modular devices located in one or more operating theaters of a healthcare facility, or any room in a healthcare facility specially equipped for surgical operations, to a cloud-based system including the cloud 1104 that includes a remote server 1113 coupled to a storage device 1105, e.g., the cloud 1004 that includes the remote server 113 coupled to the storage device 1005. The modular communication hub 1103 includes a network hub 1107 and/or a network switch 1109 in communication with a network router 1111. The network hub 1107, the network switch 1109, and the network router 1111 define the communication hub's communications interface. The modular communication hub 1103 also can be coupled to a local computer system 1110 to provide local computer processing and data manipulation. The surgical data network 1101 can be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 1107 or network switch 1109. An "intelligent surgical data network" may be referred to as a "manageable hub" or "manageable switch." A switching hub reads the destination address of each packet and then forwards the packet to the correct port.

Modular devices $1_a$-$1_n$, e.g., any number of surgical instruments such as instruments 1012 and/or any number of drug delivery devices such as devices 1014, located in the operating theater can be coupled to the modular communication hub 1103. The network hub 1107 and/or the network switch 1109 can be coupled to a network router 1111 to connect the devices $1_a$-$1_n$ to the cloud 1104 or the local computer system 1110. Data associated with the devices $1_a$-$1_n$ can be transferred to cloud-based computers via the router for remote data processing and manipulation. Data associated with the devices $1_a$-$1_n$ can also be transferred to the local computer system 1110 for local data processing and manipulation. Modular devices $2_a$-$2_m$ located in the same operating theater also can be coupled to a network switch 1109. The network switch 1109 can be coupled to the network hub 1107 and/or the network router 1111 to connect to the devices $2_a$-$2_m$ to the cloud 1104. Data associated with the devices $2_a$-$2_n$ can be transferred to the cloud 1104 via the network router 1111 for data processing and manipulation. Data associated with the devices $2_a$-$2_m$ can also be transferred to the local computer system 1110 for local data processing and manipulation. The numbers n, m of the devices $1_a$-$1_n$/$2_a$-$2_m$ can be the same as or different from one another.

A person skilled in the art will appreciate that the surgical data network 1101 can be expanded by interconnecting multiple network hubs 1107 and/or multiple network switches 1109 with multiple network routers 1111. The modular communication hub 1103 can be contained in a modular control tower configured to receive multiple devices $1_a$-$1_n$/$2_a$-$2_m$. The local computer system 1110 also can be contained in a modular control tower. The modular communication hub 1103 is connected to a display 1112 to display images obtained by at least some of the devices $1_a$-$1_n$/$2_a$-$2_m$, for example during surgical procedures.

The surgical data network 1101 can include a combination of network hub(s), network switch(es), and network router (s) connecting the devices $1_a$-$1_n$/$2_a$-$2_m$ to the cloud 1104. Any one of or all of the devices $1_a$-$1_n$/$2_a$-$2_m$ coupled to the network hub 1107 or network switch 1109 can collect data in real time and transfer the data to cloud computers for data processing and manipulation. Alternatively or in addition, any one or all of the devices $1_a$-$1_n$/$2_a$-$2_m$ coupled to the network hub 1107 or network switch 1109 can transfer previously collected data, such as sensor data, to cloud computers for data processing and manipulation, e.g., once the one or all of the devices $1_a$-$1_n$/$2_a$-$2_m$ is operatively connected to the cloud 1104 via the communication hub 1103. A person skilled in the art will appreciate that cloud computing relies on sharing computing resources rather than having local servers or personal devices to handle software applications. The term "cloud" can be used as a metaphor for "the Internet," although the term is not limited as such. Accordingly, the term "cloud computing" may be used herein to refer to "a type of Internet-based computing," where different services, such as servers, storage, and applications, are delivered to the modular communication hub 1103 and/or the computer system 1110 located in the surgical theater (e.g., a fixed, mobile, temporary, or field operating room or space) and to devices connected to the modular communication hub 1103 and/or the computer system 1110 through the Internet. The cloud infrastructure can be maintained by a cloud service provider. In this context, the cloud service provider can be the entity that coordinates the usage and control of the devices $1_a$-$1_n$/$2_a$-$2_m$ located in one or more operating theaters. The cloud computing services can perform a large number of calculations based on the data gathered by smart surgical instruments, smart drug delivery devices, robots, and other computerized devices located in the operating theater. The hub hardware enables multiple devices or connections to be connected to a computer that communicates with the cloud computing resources and storage.

Applying cloud computer data processing techniques on the data collected by the devices $1_a$-$1_n$/$2_a$-$2_m$, the surgical data network may provide improved surgical outcomes, reduced costs, and/or improved patient satisfaction. At least some of the devices $1_a$-$1_n$/$2_a$-$2_m$, e.g., one or more of the surgical instruments 1012, can be employed to view tissue states to assess leaks or perfusion of sealed tissue after a tissue sealing and cutting procedure. At least some of the devices $1_a$-$1_n$/$2_a$-$2_m$, e.g., one or more of the surgical instruments 1012, can be employed to identify pathology, such as the effects of diseases, using the cloud-based computing to examine data including images of samples of body tissue for diagnostic purposes. This includes localization and margin confirmation of tissue and phenotypes. At least some of the devices $1_a$-$1_n$/$2_a$-$2_m$, e.g., one or more of the surgical instruments 1012, can be employed to identify anatomical structures of the body using a variety of sensors integrated with imaging devices and techniques such as overlaying images captured by multiple imaging devices. At least some of the devices $1_a$-$1_n$/$2_a$-$2_m$, e.g., one or more of the drug delivery devices 1014, can be employed to identify dimensions of a patient's bariatric sleeve in bariatric surgical intervention using, e.g., an insulin pump, to facilitate visualization of the sleeve. The data gathered by the devices $1_a$-$1_n$/$2_a$-$2_m$, including image data, can be transferred to the cloud 1104 or the local computer system 1110 or both for data processing and manipulation including image processing and manipulation. The data can be analyzed to improve surgical procedure outcomes by determining if further treatment, such as the application of endoscopic intervention, emerging technologies, a targeted radiation, targeted intervention, precise robotics to tissue-specific sites and conditions, and drug administration may be pursued. Such data analysis can further employ outcome analytics processing, and using standardized approaches may provide beneficial feedback to either confirm surgical treatments and the behavior of the surgeon or suggest modifications to surgical treatments, surgeon behavior, drug delivery devices, and/or drugs.

The operating theater devices $1_a$-$1_n$ can be connected to the modular communication hub 1103 over a wired channel or a wireless channel depending on the configuration of the devices $1_a$-$1_n$, to a network hub. The network hub 1107 can be implemented as a local network broadcast device that works on the physical layer of the Open System Interconnection (OSI) model. The network hub provides connectivity to the devices $1_a$-$1_n$ located in the same operating theater network. The network hub 1107 collects data in the form of packets and sends them to the router 1111 in half duplex mode. The network hub 1107 does not store any media access control/Internet Protocol (MAC/IP) to transfer the device data. Only one of the devices can send data at a time through the network hub 1107. The network hub 1107 has no routing tables or intelligence regarding where to send information and broadcasts all network data across each connection and to a remote server over the cloud 1104. The network hub 1107 can detect basic network errors such as collisions, but having all information broadcast to multiple ports can be a security risk and cause bottlenecks.

The operating theater devices $2_a$-$2_m$ can be connected to a network switch 1109 over a wired channel or a wireless channel. The network switch 1109 works in the data link layer of the OSI model. The network switch 1109 is a multicast device for connecting the devices $2_a$-$2_m$ located in the same operating theater to the network. The network switch 1109 sends data in the form of frames to the network router 1111 and works in full duplex mode. Multiple devices $2_a$-$2_m$ can send data at the same time through the network switch 1109. The network switch 1109 stores and uses MAC addresses of the devices $2_a$-$2_m$ to transfer data.

The network hub 1107 and/or the network switch 1109 are coupled to the network router 1111 for connection to the cloud 1104. The network router 1111 works in the network layer of the OSI model. The network router 1111 creates a route for transmitting data packets received from the network hub 1107 and/or the network switch 1111 to cloud-based computer resources for further processing and manipulation of the data collected by any one of or all the devices $1_a$-$1_n$/$2_a$-$2_m$. The network router 1111 can be employed to connect two or more different networks located in different locations, such as, for example, different operating theaters of the same healthcare facility or different networks located in different operating theaters of different healthcare facilities. The network router 1111 sends data in the form of packets to the cloud 1104 and works in full duplex mode. Multiple devices can send data at the same time. The network router 1111 uses IP addresses to transfer data.

In one example, the network hub 1107 can be implemented as a USB hub, which allows multiple USB devices to be connected to a host computer. The USB hub can expand a single USB port into several tiers so that there are more ports available to connect devices to the host system computer. The network hub 1107 can include wired or wireless capabilities to receive information over a wired channel or a wireless channel. A wireless USB short-range, high-bandwidth wireless radio communication protocol cab be employed for communication between the devices $1_a$-$1_n$ and devices $2_a$-$2_m$ located in the operating theater.

In other examples, the operating theater devices $1_a$-$1_n$/$2_a$-$2_m$ can communicate to the modular communication hub 1103 via Bluetooth wireless technology standard for exchanging data over short distances (using short-wavelength UHF radio waves in the ISM band from 2.4 to 2.485 GHz) from fixed and mobile devices and building personal area networks (PANS). In other aspects, the operating theater devices $1_a$-$1_n$/$2_a$-$2_m$ can communicate to the modular communication hub 1103 via a number of wireless or wired communication standards or protocols, including but not limited to Wi-Fi (IEEE 802.11 family), WiMAX (IEEE 802.16 family), IEEE 802.20, long-term evolution (LIE), and Ev-DO, HSPA+, HSDPA+, HSUPA+, EDGE, GSM, GPRS, CDMA, TDMA, DECT, and Ethernet derivatives thereof, as well as any other wireless and wired protocols that are designated as 3G, 4G, 5G, and beyond. The computing module can include a plurality of communication modules. For example, a first communication module may be dedicated to shorter-range wireless communications such as Wi-Fi and Bluetooth, and a second communication module can be dedicated to longer-range wireless communications such as GPS, EDGE, GPRS, CDMA, WiMAX, LTE, Ev-DO, and others.

The modular communication hub 1103 can serve as a central connection for one or all of the operating theater devices $1_a$-$1_n$/$2_a$-$2_m$ and handle a data type known as frames. Frames carry the data generated by the devices $1_a$-$1_n$/$2_a$-$2_m$. When a frame is received by the modular communication hub 1103, it is amplified and transmitted to the network router 1111, which transfers the data to the cloud computing resources by using a number of wireless or wired communication standards or protocols, as described herein.

The modular communication hub 1103 can be used as a standalone device or be connected to compatible network hubs and network switches to form a larger network. The modular communication hub 1103 is generally easy to install, configure, and maintain, making it a good option for networking the operating theater devices $1_a$-$1_n$/$2_a$-$2_m$.

Data received by a surgical hub regarding drug administration devices and regarding patients can be used in any of a variety of ways. In an exemplary embodiment, the surgical hub can receive data from drug administration devices and/or one or more sensors in use with a patient in a surgical setting, e.g., in use in an operating room during performance of a surgical procedure. The surgical hub can use the received data in any of one or more ways, as discussed further below.

The surgical hub can be configured to analyze the received data in real time with use of the drug administration devices and adjust control one or more of the drug administration devices and/or one or more surgical instruments in use with the patient based on the analysis of the received data. Such adjustment can include, for example, causing more of a drug previously delivered to the patient in the surgical setting to be delivered to the patient by one or more of the drug delivery devices, causing a drug not previously delivered to the patient in the surgical setting to be delivered to the patient by one or more of the drug delivery devices, adjusting one or operational control parameters of at the one or more surgical instruments, causing one or more sensors of one or more of the drug administration devices and/or of one or more surgical instruments to take a measurement to help gain an understanding of the patient's current physiological condition, current operational status of a drug administration device, and/or current operational status of a surgical instrument, and other adjustments. Controlling and adjusting operation of drug administration devices is discussed further below. Examples of the operational control parameters include motor speed, cutting element speed, time, duration, and level of energy application. Controlling and adjusting operation of surgical instruments is described further in previously mentioned U.S. Pat. Pub. No. 2019/0200844 entitled "Method Of Hub Communication, Processing, Storage And Display" filed Dec. 4, 2018 and U.S. Pat. Pub. No. 2019/0201114 entitled "Adaptive Control Program Updates For Surgical Hubs" filed Mar. 29, 2018, and in U.S. Pat. Pub. No. 2019/0207857 entitled "Surgical Network Determination Of Prioritization Of Communication, Interaction, Or Processing Based On System Or Device Needs" filed Nov. 6, 2018 and U.S. Pat. Pub. No. 2019/0206555 entitled "Cloud-based Medical Analytics For Customization And Recommendations To A User" filed Mar. 29, 2018, which are hereby incorporated by reference in their entireties.

The surgical hub can be configured to cause visualization of the received data to be provided in the surgical setting on a display so that medical professionals in the surgical setting can view the data and thereby receive an understanding of the operation of the drug administration device(s) in use in the surgical setting. Such information provided via visualization can include text and/or images indicating when any of the drug administration device(s) administered a drug to the patient, identifying which drug(s) have been administered to the patient by any of the drug administration device(s), indicating whether any of the drug administration device(s) encountered an error in attempting to deliver a drug to the patient, and other types of information.

Operating Drug Administration Devices

When delivering drugs using any of the drug delivery devices discussed above or any other drug delivery device, a variety of factors can influence drug administration, absorption, and effect on a patient beyond simply the initial drug dose itself. For example, individual patient physiologies or statuses, physiological effects on a patient of drug administration, surrounding external conditions to the patient, etc. can all influence results of drug administration on a patient. It can thus be beneficial to a patient to allow drug delivery to be adjusted based on a variety of different factors that arise during use of drug administration devices, providing more personalized treatment while also helping a patient receive and/or a doctor deliver specialized care for the specific patient being treated. Additionally, being able to automate as much of the drug delivery adjustment can help ease the process of delivery for both the patient and the doctor, while improving patient outcomes. In a surgical setting in which the drug administration device is being used during performance of a surgical procedure, being able to automate as much of the drug delivery adjustment can help ease the process of delivery for the surgeon and/or other medical personnel and free time for the surgeon and/or other medical personnel to focus on surgical tasks other than drug delivery adjustment, while improving patient outcomes.

In at least some implementations, drug delivery can be altered based on one or more characteristics associated with the patient that are determined based on situational awareness of the patient. In an exemplary embodiment, at least one sensor is configured to gather data regarding a characteristic associated with the patient. In embodiments including multiple sensors, each of the sensors can be configured to gather data regarding a different characteristic associated with the patient. In some embodiments, a drug administration device includes at least one sensor configured to gather data regarding a characteristic associated with a patient. In some embodiments, at least one sensor external to and separate from a drug administration device is configured to gather data regarding a characteristic associated with a patient. The at least one external, separate sensor can be, for example, a sensor of a surgical instrument or other device in use in a same surgical procedure as the drug administration device. In some embodiments, a drug administration device includes at least one sensor configured to gather data regarding a characteristic associated with a patient, and at least one sensor external to and separate from the drug administration device is configured to gather data regarding a characteristic associated with a patient that can be the same as the characteristic associated with the at least one sensor of the drug administration device or can be a different characteristic than the characteristics associated with the at least one sensor of the drug administration device.

An algorithm stored on the drug administration device, e.g., in a memory thereof, is executable on board the drug administration device, e.g., by a processor thereof, to administer a dose of a drug to a patient. In some embodiments, instead of or in addition to being stored on the drug administration device, the algorithm can be stored on a surgical hub, e.g., in a memory thereof, that is configured to communicate with the drug administration device.

The algorithm is stored in the form of one or more sets of pluralities of data points defining and/or representing instructions, notifications, signals, etc. to control functions of the device and administration of the drug. Data gathered by at least one sensor is used, e.g., by the drug administration device's processor, to change at least one variable parameter of the algorithm. As discussed above, a surgical hub can be in communication with a drug administration device, so data gathered by the drug administration device and by at least one external, separate sensor in communication with the surgical hub can be communicated to the surgical hub and communicated from the surgical hub to the drug administration device. Alternatively, or in addition, the data gathered by at least one sensor can be used by the surgical hub, e.g., by the drug administration device's processor, to change at least one variable parameter of the algorithm, and the surgical hub can communicate the changed at least one variable, alone or as part of the algorithm, to the drug administration device and/or the surgical hub can communicate an instruction to the drug administration device to change the at least one variable as determined by the surgical hub using the gathered by the at least one sensor.

The at least one variable parameter is among the algorithm's data points, e.g., are included in instructions for drug delivery, and are thus each able to be changed by changing one or more of the stored pluralities of data points of the algorithm. After the at least one variable parameter has been changed, subsequent execution of the algorithm administers another dose of the drug according to the changed algorithm. As such, drug delivery over time can be managed for a patient to increase the beneficial results of the drug by taking into consideration actual situations of the patient and actual results of the patient receiving doses of the drug. Changing the at least one variable parameter and/or administration of the one or more doses themselves is automated to improve patient outcomes. Thus, the drug administration device can be configured to provide personalized medicine based on the patient and the patient's surrounding conditions to provide a smart system for drug delivery. In a surgical setting in which the drug administration device is being used during performance of a surgical procedure, automated changing of the at least one variable parameter and/or administration of the one or more doses may allow for drug administration to be controlled based on data gathered during the performance of the surgical procedure, which may help the patient receive a drug quickly in response to a sensed or determined condition and/or may help ensure that a drug is delivered to the patient on schedule per the patient's pre-operative plan.

Figure 5:
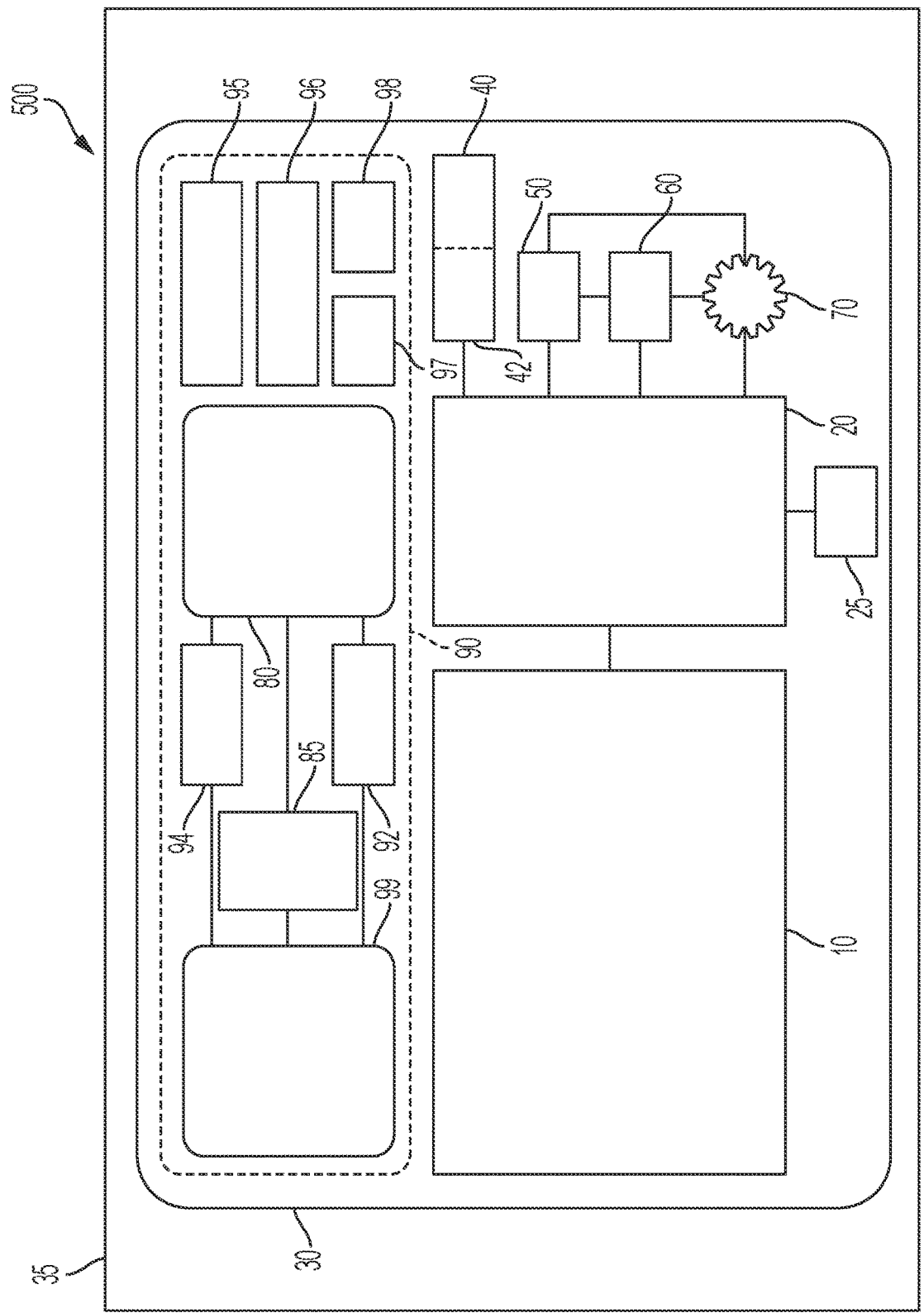
FIG. 5 is a schematic view of a universal drug administration device.

Using the universal drug administration device 500 of FIG. 5 by way of example, the memory 97 can have stored therein the algorithm, and the processor 96 can be configured to execute the algorithm to control delivery of a dose of the drug dispensed by the dispensing mechanism 20. The processor 96 can also be configured to use data gathered by at least two of the one or more device sensors 92, environment sensor 94, and location sensor 98 (in addition to or instead of at least one external, separate sensor) to change at least one variable parameter of the algorithm such that a dose delivered subsequent to the changing of the at least one variable parameter will be controlled by execution of the changed algorithm. As mentioned above, a person skilled in the art will appreciate that the universal drug administration device 500 can be provided with a variety of the optional features described above, in a number of different combinations, e.g., not include any of the sensors 92, 94, 98 not being used by the processor 96 to change variable parameter(s) of the algorithm (and instead include sensor(s) to gather the needed situational awareness data), not include packaging 35, not include user interface 80, etc.

Figure 11:
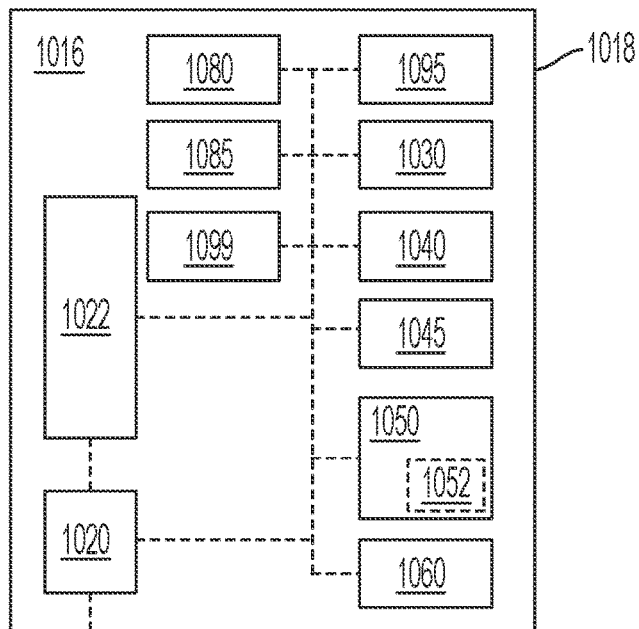
FIG. 11 is a schematic view of another embodiment of a drug administration device.

FIG. 11 illustrates one embodiment of a universal drug administration device 1016 configured to alter drug delivery to a patient based on one or more various characteristics associated with the patient that are determined based on situational awareness of the patient, such as during performance of a surgical procedure. The drug administration device 1016 in this illustrated embodiment includes a housing 1018, a drug holder 1022, a dispensing mechanism 1020, sensors 1030, 1040, 1045, a memory 1050 storing an algorithm 1052 therein that includes at least one variable parameter, a processor 1060, a user interface 1080, an indicator 1085, a power supply 1095, and a communications interface 1099. The sensors 1030, 1040, 1045 can each be configured to measure a different parameter, as discussed herein. Additionally, similar to that mentioned above regarding the universal drug administration device 500 of FIG. 5, a person skilled in the art will appreciate that the universal drug administration device 1016 of FIG. 11 including the drug holder 1022, the dispensing mechanism 1020, the processor 1060, the memory 1050, and the sensors 1030, 1040, 1045 can be provided with a variety of the features described above, in a number of different combinations. For example, the device 1016 may include at least one sensor but not all of the sensors 1030, 1040, 1045, may include at least two sensors but not all of the sensors 1030, 1040, 1045, may not include any of the sensors 1030, 1040, 1045 with any sensor functionality being provided by at least one external, separate sensor, may not have a user interface 1080, etc.

The first, second, and third sensors 1030, 1040, 1045 are each housed either within the housing 1018 or on an exterior surface of the housing 1018, and each sensor 1030, 1040, 1045 is configured to gather data regarding a characteristic associated with the patient. The sensors 1030, 1040, 1045 can each include a device sensor (similar to device sensor 92 discussed above), an environment sensor (similar to environment sensor 94 discussed above), or a location sensor (similar to location sensor 98 discussed above). Each of the sensors 1030, 1040, 1045 is configured to gathers data for a different characteristic. The characteristics can be physiological characteristics and/or situational characteristics of the patient. Various different physiological characteristics can be monitored, such as blood sugar level (e.g., using a glucose monitor, etc.), blood pressure (e.g., using a blood pressure monitor, etc.), perspiration level (e.g., using a fluid sensor, etc.), heart rate (e.g., using a heart rate monitor, etc.), etc. Furthermore, a number of different situational characteristics can be monitored, such as core temperature, (e.g., using a temperature sensor), tremor detection (using an accelerometer, etc.), time of day (e.g., using a timer, etc.), date (e.g., using a timer, etc.), patient activity level (e.g., using a motion sensor, etc.), blood pressure (e.g., using a blood pressure monitor, etc.), metabolic rate (e.g., using heart rate as discussed herein, etc.), altitude (e.g., using an altimeter, etc.), temperature of the drug (e.g., using a temperature sensor), viscosity of the drug (e.g., using a viscometer, etc.), GPS information (e.g., using a location sensor, etc.), weather information (e.g., using a temperature sensor, humidity sensor, etc.), room or external temperature (e.g., using a temperature sensor), angular rate (e.g., using an inertial measurement unit (IMU) or MARG (magnetic, angular rate, and gravity) sensor), body orientation (e.g., using an IMU, etc.), current of a motor used in delivering the drug (e.g., using a current sensor), blood oxygenation level (e.g., using a blood oxygen sensor), sun exposure (e.g., using a UV sensor, etc.), osmolality (e.g., using a blood monitor, etc.), and air quality (e.g., using a UV sensor, etc.), inflammatory response, one or more images and/or videos of the patient and/or an environment in which the patient is located (for example, to analyze food intake; to determine whether solid food or liquid is being consumed; to determine a location or activity of the patient; to determine a condition of the patient such as skin reaction, breathing, eye dilation, voice characteristics such as tone and pitch; etc.), user-input data such as general well-being, pain score, or a cycle time between flare ups of a particular ailment, etc. In an exemplary embodiment, one sensor 1030, 1040, 1045 is configured to monitor either a physiological or a situational characteristic and the others of the sensors 1030, 1040, 1045 are configured to monitor the other of physiological or situational characteristics. In another exemplary embodiment, each of the sensors 1030, 1040, 1045 is configured to monitor a different physiological characteristic. In another exemplary embodiment, each of the sensors 1030, 1040, 1045 is configured to monitor a different situational characteristic.

While three sensors are illustrated in FIG. 11, the device 1016 can include only one sensor, can include only two sensors, or can include more than three sensors. Any additional sensors can be configured similarly to sensors 1030, 1040, 1045 and be configured to monitor different characteristics than the sensors 1030, 1040, 1045 and from each other. In embodiments additionally or alternatively including at least one external, separate sensor, the at least one external, separate sensor can be configured similar to that discussed above regarding the sensors 1030, 1040, 1045.

The memory 1050 of the drug administration device 1016 is located in the housing 1018. In this illustrated embodiment, the memory 1050 is configured to store data from the sensors 1030, 1040, 1045, however in other embodiments this data can be stored elsewhere, such as in another memory on board the drug administration device 1016 and/or in a remote memory, e.g., a surgical hub's memory, a cloud server's memory, or other memory, accessible to the drug administration device 1016 via the communications interface 1099. The algorithm 1052 stored in the memory 1050 represents instructions for the drug administration device 1016 regarding how to administer the drug in the drug holder 1022 and is configured to be executed by the processor 1060. The algorithm 1052 is stored in the form of a plurality of data points defining and/or representing instructions, notifications, signals, etc. to control drug administration, with the at least one variable parameter being among the data points such that changing the at least one variable parameter of the algorithm 1052 results in at least one change in how the drug is administered. The at least one variable parameter can be any of a variety of different delivery and/or drug parameters. Examples of variable parameters include a rate of delivery of the drug from the drug holder 1022 to the patient, a time interval between dose deliveries such that doses delivered after the at least one variable parameter is changed are at a different time interval than doses delivered before the change, a dosage amount, a dosage concentration, whether or not any addition doses are delivered such as stopping a second or any subsequent dose or starting to dose again after dosing was previously stopped, etc.

The processor 1060 is configured to receive and analyze data from the one or more sensors 1030, 1040, 1045 and to execute the algorithm 1052 to control administration of one or more doses of the drug to the patient. In an exemplary embodiment, the processor 1060 executes the algorithm 1052 to control delivery of at least a first dose of the drug to the patient, changes the at least one variable parameter of the algorithm 1052 based on data gathered by the sensors 1030, 1040, 1045, and executes the algorithm 1052 after changing the at least one variable parameter to control delivery of at least one subsequent dose of the drug. To execute the algorithm 1052, the processor 1060 is configured to run a program stored in the memory 1050 to access the plurality of data points of the algorithm 1052 in the memory 1050. To change the at least one variable parameter of the algorithm 1052, the processor 1060 is configured to modify or update the data point(s) of the at least one variable parameter in the memory 1050. The processor 1060 can also be configured to execute instructions stored in the memory 1050 to control the device 1016 generally, including other electrical components thereof such as the communications interface 1099, the indicator 1085, and the user interface 1080. The processor 1060 can be configured to change the at least one variable parameter of the algorithm 1052 during the delivery of a dose such that the algorithm 1052 is changed in real time with the delivery of the dose (e.g., in real time with execution of the algorithm) and/or in real time with use of the drug administration device 1016 during performance of a surgical procedure, which may accommodate real time sensed conditions. The processor 1060 can be configured to change the at least one variable parameter of the algorithm 1052 before a start of the delivery of the dose, which may consume less memory and use fewer processing resources during algorithm 1052 execution than real time changing of the algorithm 1052 during algorithm execution. As discussed above, instead of or in addition to using data from the one or more sensors 1030, 1040, 1045, data from at least one external, separate sensor can be used.

In other embodiments, as discussed further below, instead of the processor 1060 of the drug administration device 1016, a processor of a surgical hub configured to be in communication with the drug administration device 1016 during performance of a surgical procedure is configured to receive and analyze data from the one or more sensors 1030, 1040, 1045 (and/or at least one external, separate sensor). The surgical hub can be configured to communicate an instruction to the drug administration device 1016, e.g., a communications interface of the surgical hub transmitting an instruction to the communications interface 1099 of the drug administration device 1016, to update the algorithm 1052 by changing at least one variable parameter of the algorithm 1052 similar to that discussed herein regarding to the drug administration device 1016 itself changing at least one variable parameter of the algorithm 1052. The drug administration device 1016 may thus require less processing power and/or less memory space than if the drug administration device 1016 handles analysis of sensor data and decisions to change the algorithm 1052 based on such analysis.

The processor 1060 can be configured to automatically control delivery of doses of the drug based on one or more predetermined schedules or intervals of dosing for the patient, which can be predetermined prior to an initial dose or can be determined during use of the drug administration device 1016 after delivery of the first dose and set such that future doses can be based on the predetermined schedule(s). The predetermined schedule(s) can also be determined by a surgeon or other doctor, or other care provider, created automatically based on the algorithm 1052 and/or the sensors 1030, 1040, 1045 (and/or at least one external, separate sensor) being used, or some combination thereof.

The processor 1060 can be configured to cause a notification to be provided to the patient and/or the doctor or other care provider based on gathered data from one or more of the sensors 1030, 1040, 1045 (and/or at least one external, separate sensor), for example via the device indicator 1085, user interface 1080, and/or communications interface 1099. Additionally or alternatively, a surgical hub in communication with the drug administration device 1016 can be configured to cause a notification to be provided to the surgeon and/or other surgical personnel based on gathered data from one or more of the sensors 1030, 1040, 1045 (and/or at least one external, separate sensor), for example via a display of the surgical hub.

Because the processor 1060 (or a processor of a surgical hub configured to be in communication with the drug administration device 1016 during performance of a surgical procedure) is configured to alter the at least one variable parameter based on data gathered by one or more of the sensors 1030, 1040, 1045 (and/or by at least one external, separate sensor), whether or not the drug administration device's processor or a surgical hub's processor performs sensor analysis, an automated reaction response based on the situational awareness of the patient is possible. In at least some embodiments, the at least one variable parameter is altered to provide adaptive dose adjustment based on various readings and/or data from one or more of the sensors 1030, 1040, 1045 (and/or at least one external, separate sensor) and/or user inputs. For example, a user can record a cycle time between flare ups of a disease or ailment, at which point the drug dosing schedule as reflected in the algorithm 1052 can be adjusted by the processor 1060 and/or remotely by a doctor or other care provider to take this into account for better disease control. As another example, changes in altitude of a patient can potentially alter the effectiveness of medications and even lead to toxicity in some cases. As such, the duration at which a patient is at a different altitude can be read by one or more of the sensors 1030, 1040, 1045 and be used by the processor 1060 and/or a doctor or other care provider to adjust subsequent drug dosages by the processor 1060 changing the at least one variable parameter. In another example, a treatment can be discontinued entirely based on one or more sensor readings. The treatment can be discontinued, in some instances, during performance of a surgical procedure of a patient. A patient, a surgeon or other doctor, and/or other(s) can be informed of treatment discontinuation, e.g., through the device indicator 1085, through the user interface 1080, via a display of a surgical hub, via a speaker of a surgical hub, etc. One or more possible complications can be anticipated based on best practices and/or on analysis performed by a surgical hub and/or a cloud server, and the processor 1060 and the memory 1050 can operate together to provide various digital ready reactions to common complications (identified through situational awareness) to alert the patient, attempt to change a behavior of the patient, notify the doctor, etc. In various embodiments, at least one of the sensors 1030, 1040, 1045 (and/or at least one external, separate sensor) includes a camera, and the processor 1060 is configured to analyze image(s) and/or video(s) captured by the camera, such as to analyze any food intake and/or patient skin reaction to the drug.

The device indicator 1085 and/or the user interface 1080 can be configured to operate independently of each other or configured to operate together to provide various notifications to the patient and/or a doctor or other care provider of any outputs of situational awareness based on sensor readings and any complications those readings could indicate. As such, a patient and/or medical personnel may be able to react quickly to any negative results of administration of the drug and/or complications as a result of treatment. In at least some embodiments the drug administration device 1016 can be configured to provide activities the patient can pursue to best manage their condition, such as by providing suggested activities via the user interface 1080. Furthermore, information of situational awareness based on sensor readings and any complications those readings could indicate can be relayed to the patient's doctor or other care provider, who can then communicate with the patient as needed.

Basic operations on the drug administration device 1016 itself can inform the patient and/or medical personnel of any detected deviation from the so-called "five rights" of drug administration in at least some embodiments. During drug administration, best practices require ensuring that the "five rights" of medication use are followed: the right patient, the right drug, the right time, the right dose, and the right route. Tracking situational awareness of the patient through use of the sensors 1030, 1040, 1045 (and/or at least one external, separate sensor) can thus detect if any of the "five rights" are violated, at which point the patient and/or a doctor or other care provider can be informed. Furthermore, in some embodiments, confirmation of the "five rights" can be required, either by a doctor or off-site medical personnel or by the patient themselves, to help eliminate medication errors. In severe cases, a notification can be provided to the patient and/or the doctor or other care provider that immediate medical attention is needed.

The communications interface 1099 can be configured to allow one-way communication, such as providing data to a remote server (e.g., a cloud server or other server) and/or to a local, surgical hub server, and/or receiving instructions or commands from a remote server and/or a local, surgical hub server, or two-way communication, such as providing information, messages, data, etc. regarding the drug administration device 1016 and/or data stored thereon and receiving instructions, such as from a doctor, a remote server regarding updates to software, a local, surgical hub server regarding updates to software, etc. As such, doctor/care provider interaction is possible to provide additional adjustments to care. For example, doctors or other care providers can receive relevant information and data from the drug administration device 1016 via the communications interface 1099, via a surgical hub in communication with the drug administration device 1016, and/or from the patient directly and can, based on the received information, provide remote or local feedback and/or any adjustment(s) to the drug administration device 1016 (for example, requesting that the processor 1060 change the at least one variable parameters to change subsequent dosing) and/or to the patient (for example, providing recommended next steps based on current sensor readings and feedback from the patient). In at least some embodiments any recording or data of an incident and the data leading up to and resulting from the incident can be provided to the doctor and/or remote-care individuals, a local, surgical hub server, and/or a remote server for storage, and the receiving party can analyze and summarize the data to determine a recommendation regarding overcoming or effectively addressing any current complication. In at least some embodiments, the processor 1060 is configured to change the variable parameter only after communicating with a remote server and/or a local, surgical hub server and receiving any instructions therefrom.

While the sensors 1030, 1040, 1045 are all included with the drug administration device 1016 in this illustrated embodiment, as mentioned above one or more of the sensors 1030, 1040, 1045 can be separate from the drug administration device 1016 by, e.g., being worn on the patient, being placed in a shared geographical space with the patient, being attached to other equipment or instruments, being part of a mobile phone app used by the patient, etc.

Changing the at least one variable parameter can result in an adjusted injection or flow rate speed of each provided dose, e.g., the at least one variable parameter can include injection or flow rate speed. Instead or in addition, a temperature of a drug can be varied to create constant flow, as discussed, for example, in U.S. Pat. Pub. No. 2002/0042596 entitled "Method And Apparatus To Sense Temperature In An Implantable Pump" published Apr. 11, 2002, which is hereby incorporated by reference in its entirety.

Injection site pain can be minimized in at least some embodiments by the drug administration device 1016 and/or a surgical hub in communication with the drug administration device 1016 monitoring patient usage, patient preferences, patient physical attributes, the one or more sensed characteristics associated with the patient, various parameters of the drug, etc. For example, patient factors such as weight, BMI, age, etc.; type of delivery mechanism of the drug, such as bolus injection delivery, continuous delivery, inhalation, etc.; a total number and history of injections at the desired location for injectable drugs; a volume of the drug; measured parameters about a status and state of the drug itself like viscosity, temperature, pH level; can all be used to anticipate the pain involved in administering the next drug administration, such as the next injection. Various delivery parameters of the drug, such as the speed, wait period, pressure, location recommendations, etc. can then be updated through the at least one variable parameter to minimize patient pain and discomfort.

In at least some embodiments, allowing the drug administration device 1016 and/or a surgical hub in communication with the drug administration device 1016 to have more situational awareness of the patient may facilitate compliance. The drug administration device 1016 can be used to increase compliance by a patient or medical personnel and/or increase familiarity with how the drug administration device 1016 operates in any number of different ways. For example, the drug administration device 1016 and/or a surgical hub in communication with the drug administration device 1016 can be configured to provide reminders, updates, adaptive training, etc. to the patient and/or medical personnel based on compliance data and/or compliance data that is stored on or pushed out to the drug administration device 1016 and/or a surgical hub in communication with the drug administration device 1016 to reinforce healthy behaviors, teach steps of use for the device, and other details. Increasing compliance and familiarity with the drug administration device 1016 can help reduce patient risk when being administered the drug, the importance of which is discussed, for example, in U.S. Pat. Pub. No. 2015/0359966 entitled "System For Monitoring And Delivering Medication To A Patient And Method Of Using The Same To Minimize The Risks Associated With Automated Therapy" published Dec. 17, 2015, which is hereby incorporated by reference in its entirety.

Figure 12:
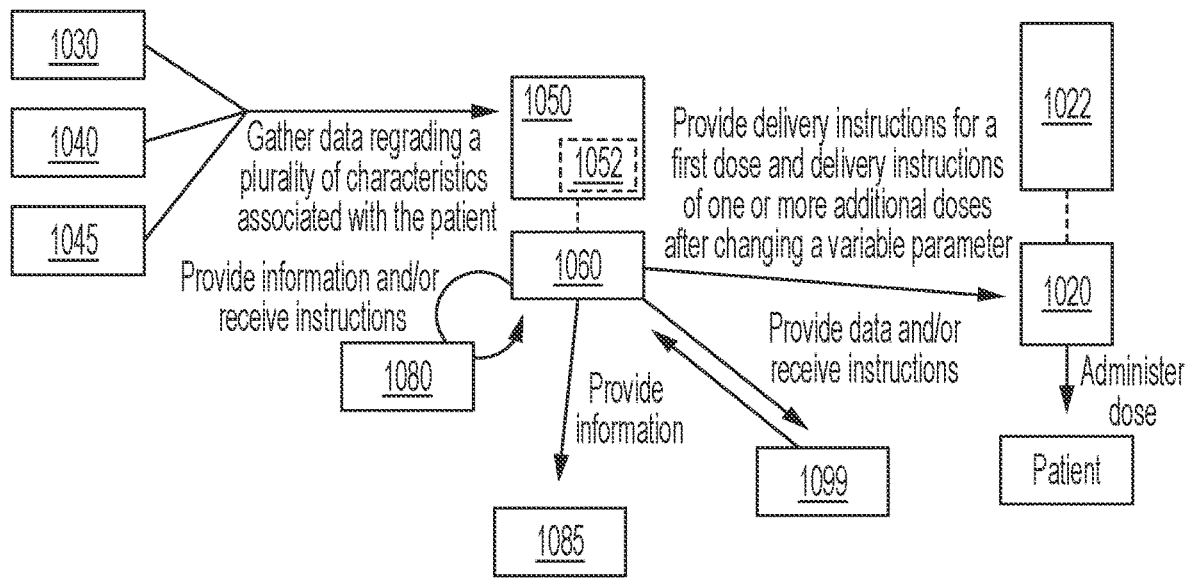
FIG. 12 is a flow diagram of the drug administration device of FIG. 11 in use.

FIG. 12 illustrates an embodiment of use of the drug administration device 1016. Prior to a first delivery of a dose of the drug, the drug administration device 1016 gathers data regarding the first characteristic associated with the patient using the first sensor 1030, gathers data regarding the second characteristic using the second sensor 1040, and gathers data regarding the third characteristic using the third sensor 1045. Alternatively or in addition, a surgical hub in communication with the drug administration device 1016 gathers data regarding the first characteristic using at least one external, separate sensor and/or receives data gathered by the sensors 1030, 1040, 1045. The first delivery of the dose can be the initial dose delivered from the drug administration device 1016 to the patient, or it can be the first dose delivered from the drug administration device 1016 to the patient after at least one dose has already been provided to the patient and after a sufficient amount of data has been gathered via the sensors 1030, 1040, 1045 and/or at least one external, separate sensor. Further data can optionally be gathered regarding additional characteristics associated with the patient by using additional secondary sensors. The data gathered represents pluralities of data points defining each characteristic and are stored in the memory 1050 and/or in the surgical hub's memory. The processor 1060 subsequently controls delivery of the first dose of the drug from the drug administration device 1016 to the patient by executing the algorithm 1052 stored in the memory 1050. The sensors 1030, 1040, 1045 and/or the at least one external, separate sensor continue gathering data. Based on any of this subsequently gathered data, the processor 1060 changes the at least one variable parameter of the algorithm 1052 as discussed above. After changing the at least one variable parameter, the processor 1060 controls delivery of at least the second dose from the drug administration device 1016 to the patient by executing the algorithm 1052. The processor 1060 executing the algorithm 1052 to deliver a dose can be automatic, manual, or some combination of the two, and it can be according to a predetermined schedule of dosing, as discussed above.

During any part of the dosage process of FIG. 12, the drug administration device 1016 can communicate with one or more computer systems, e.g., a local surgical hub, a remote server such as a cloud server, etc., using the communications interface 1099 to provide data thereto and/or receive instructions therefrom and/or can communicate with the user via the device indicator 1085 and/or the user interface 1080 to provide information thereto and/or receive instructions therefrom. In some embodiments, administering a first dose, a second dose, and/or any subsequent doses can be dependent on receiving instructions from a surgical hub and/or one or more remote computer systems. Furthermore, the second or any subsequent doses can also be prevented entirely based on changes to the variable parameter, thus resulting effectively in the second or subsequent dose being equivalent to zero dose being administered.

In at least some embodiments, the processor 1060 and/or a surgical hub (e.g., a processor thereof) is configured to use a hierarchy in terms of how data from the sensors 1030, 1040, 1045 and/or at least one external, separate sensor is used compared to each other and/or to any additional sensors. The hierarchy prioritizes one of the sensors over the other(s) such that one acts as a primary sensor, such as sensor 1030, and the other(s) act as secondary or ancillary sensor(s), such as sensors 1040, 1045. In such embodiments, the characteristic measured by the primary sensor can be considered to be the primary or defining characteristic, and characteristics measured by the secondary sensors can be secondary or influencing characteristics on the primary characteristic. This prioritization or hierarchy of characteristics (and thus data) can be helpful when the drug administration device 1016 is used for a treatment that includes one controlling characteristic and one or more secondary characteristics that may influence or assist in monitoring the controlling characteristic, for example when measuring blood pressure when administering blood pressure medication or when measuring blood sugar level when administering insulin. While secondary characteristics can help in monitoring high blood pressure or low blood sugar, the characteristics of primary concern in each example is blood pressure itself or blood sugar level itself. The prioritization of data and inputs from one or more secondary sensors based on the hierarchical relationship can be customizable based on desired patient outcomes, various expected or anticipated side-effects, the drug being administered, time of day, location, activity level, caloric intake, physical activity, etc. The drug administration device 1016 can thus have a predefined hierarchy of levels or severity of effect on dosage based on the sensed characteristics from the sensor(s). A medical professional or unlearned algorithm within the drug administration device 1016 itself and/or a surgical hub in communication with the drug administration device 1016 can optionally adjust the priority of the levels or reorder the importance of the various sensed data and inputs as a result of dosing amounts and/or dosing timelines, as discussed below. Because so much data can be generated by using a plurality of sensors and because data from one sensor may contradict data from another sensor in some instances, effectively using situational awareness to personalize drug administration to each patient may benefit from prioritization and relative weighing of multiple sources of information to arrive at a most correct conclusion or recommendation to best help the patient. This hierarchy of prioritization can be customized for a specific patient based on how the patient presents in any one moment or over time, therefore providing an adaptive device with re-orderable hierarchal relationships.

As mentioned above, the hierarchical arrangement can be used in a variety of ways, for example to verify a physiological result such that data from one or more sensors is considered to adjust the at least one variable parameter to proactively manage any anticipated negative effect on the primary characteristic being measured. The hierarchy between various sensors can be predefined; can be adaptable based on user input, such as providing input through the user interface 1085; can be adaptable based on a processor, an algorithm, any analyzed data, etc.; and/or can be adaptable through contact with remote computer systems, doctors, remote-care providers, etc.

In general, a primary characteristic for a drug administration device can be a control measure, and secondary characteristic(s) or measures can be data taken from sources surrounding the primary characteristic and/or sources that can influence and/or be influenced by the primary source. For example, blood sugar level is a primary characteristic for insulin delivery, but blood pressure is a primary characteristic for various blood pressure medications. Additionally, sources surrounding the primary source can take a variety of different forms, such as glucose level (for example, as measured by a micro needle application and/or sweat analysis); blood pressure (for example, as measured by various wearable cuffs); hydration (for example, as measured by perspiration level); heart rate and/or activity level (for example, as measured by various metabolic consumption rates, sitting or sedentary motion determined by elevation changes, various gyroscopes); EKG cycle; heart rate variability; various acute effects or activities to trigger measurement (such as sleep or sleep quality detection and/or meal detection, for example by analyzing one or more images of the patient, receiving input from the patient, etc.); discernment between eating and drinking; various long term effects to monitor any changes that might inform a new diagnoses or provide alerts to seek evaluation for any possible new conditions; core temperature; tremor detection; patient held/worn camera image analysis; time of day; digital calendar information; GPS outputs; device activity; any user interaction with the device; etc.

Additionally, numerous means for being aware of any surrounding situation during administration of the drug are possible, providing a variety of types of situational awareness that one or more drug administration devices can use. As further examples, forms of cognitive analysis can be performed on the patient by combining small interactions with the patient and various automated sensors on or around the patient to determine cognitive effects of any drug dosage on the patient. Various measured reactions to drug dosages can also be analyzed, such as timing to a first effect, effect duration, magnitude of effect, etc. Ending continued application of a drug can be one result, however there are many other examples where such an action can be taken. For example, if a biologic or drug is being delivered on an ongoing basis, the plurality of sensors can allow detection of an onset of a complex biologic response to the biologic or drug, and a drug administration device can have the ability to affect, retard, or end the continued application of the biologic or drug. Thus, drug administration devices and/or surgical hubs described herein can be configured to provide detection of and an automated response to collateral physiologic reactions to any continuous biologic introduction. For example, injection reactions can be an issue for some biologics, especially when delivered through an IV given delivery times and the continuous administration. Thus, drug administration devices and/or surgical hubs described herein can be configured to detect various onsets of injection reactions, such as through sensor(s), and consequently stop or slow down delivery of the drug. In at least some embodiments, drug administration devices described herein can be configured to deliver other medication(s) to stop, lessen, or counteract the drug injection reaction. As another example, cytokine release syndrome is a form of systemic inflammatory response syndrome that can arise from an adverse effect of some monoclonal antibody drugs, as well as adoptive T-cell therapies. Once a drug administration device, or other system in communication with the drug administration device, detects pro- and anti-inflammatory components above a predetermined threshold in a patient, the drug administration device can be configured to reduce or stop the introduction of the treatment. In such an example, the drug administration device and/or a surgical hub can also be configured to notify medical personnel or introduce a canceling agent to accelerate the reduction of the response. If the injection response is great enough as defined by predefined criteria, the drug administration device can be configured to automatically escalate its response, or a surgical hub can be configured to cause the drug administration device to escalate its response, from a passive indication or reduction of dosage to a more active warning notification or introductions of other active countermeasures. Even when medical intervention is required, such as requiring a patient to go into a hospital for emergency treatment or altering a pre-operative plan during surgery, the drug administration devices and surgical hubs described herein can be configured to use biometric data to detect changes in the patient's body, such as body temperature or heart rate, that typically proceed a serious effect. The drug administration device and/or the surgical hub can be configured to notify the patient and/or medical personnel of the imminent effect to allow the patient and/or medical personnel to take preemptive action, such as taking medication at home before then going into the hospital before one or more major side effects take place, preparing another drug for delivery, etc. This early warning can improve patient outcomes by reducing any negative consequences.

In at least some implementations, drug delivery from a drug administration device is altered based on interaction between a drug administration device and an accessory, representing a cooperative or closed-loop relationship between the drug administration device and the accessory. The accessory can either be retained in or on the drug administration device or can be external to and separate therefrom. A surgical hub is one example of an accessory that is external to and separate from a drug administration device. The accessory includes a processor configured to receive data from at least one sensor of the drug administration device that is indicative of a patient's physiological characteristic and to control delivery of the drug from the drug administration device to the patient based on the received data. As such, dosages can be varied over time based on the sensor data and interaction with the accessory to allow for more personalized drug administration during each dose and over time, thus increasing the beneficial results of the drug by taking into consideration actual, present conditions of the patient. This functionality is similar to that discussed above with respect to FIGS. 11 and 12 except that the accessory, not the drug administration device, manages an algorithm controlling drug delivery from the drug administration device. The drug administration device may thus be less "smart" than the drug administration device 1016 of FIG. 11 and, consequently, be smaller and/or less expensive. Also, it is typically less expensive and/or easier for the patient to upgrade accessories, such as wearable accessories, and/or acquire new accessories than for the patient to upgrade the drug administration device or acquire a new drug administration device, so offloading processing and algorithm control to the accessory may extend the useful life of the drug administration device.

Figure 13:
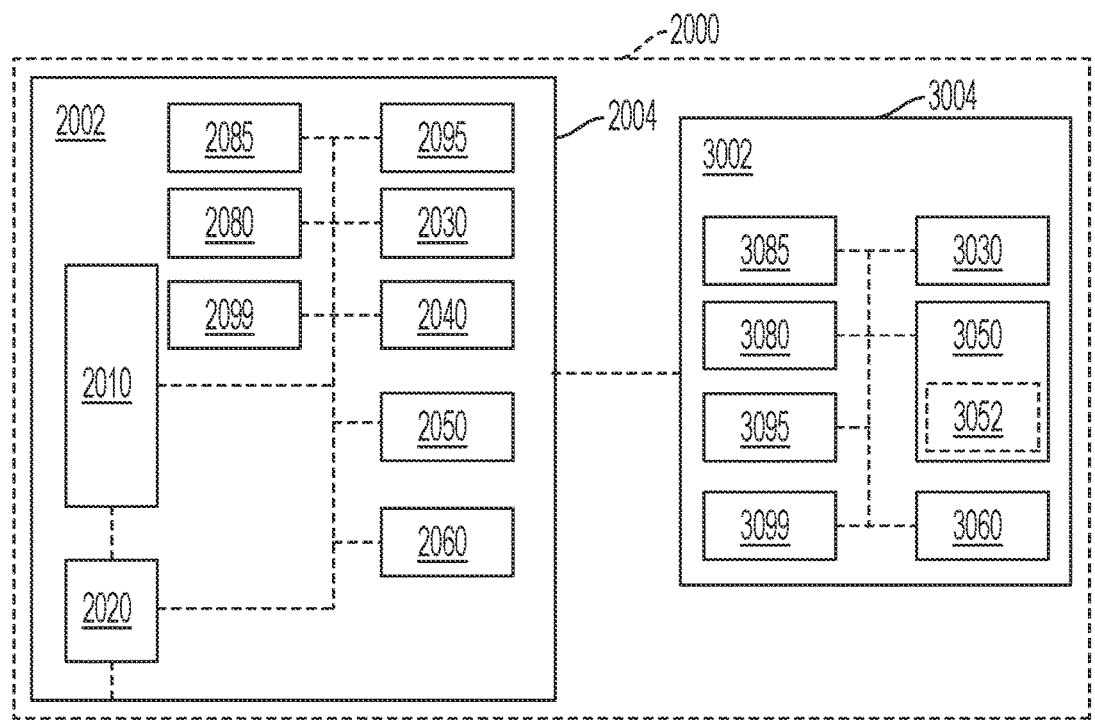
FIG. 13 is a schematic view of another embodiment of a drug administration device.

FIG. 13 illustrates one embodiment of a drug administration system 2000 including a universal drug administration device 2002 and an accessory 3002. The drug administration device 2002 in this illustrated embodiment includes a housing 2004, a drug holder 2010, a dispensing mechanism 2020, at least one sensor 2030, 2040, a memory 2050, a processor 2060, a user interface 2080, an indicator 2085, a power supply 2095, and a communications interface 2099. The accessory 3002 in this illustrated embodiment includes a housing 3004, at least one sensor 3030, a memory 3050 configured to store an algorithm 3052 therein, a user interface 3080, a device indicator 3085, a processor 3060, a power supply 3095, and a communications interface 3099. Additionally, similar to that mentioned above, a person skilled in the art will appreciate that each of the universal drug administration device 2002 and the accessory 3002 can be provided with a variety of the features described above, in a number of different combinations.

First and second sensors 2030, 2040 of the drug administration device 2002 are similar to the sensors 1030, 1040, 1045 of FIG. 11 discussed above. In an exemplary embodiment each sensor 2030, 2040 is configured to gather data regarding a physiological characteristic of the patient. For example, the sensed physiological characteristics can be any two or more of a reaction of the patient to the drug delivered thereto, blood sugar level, blood pressure, perspiration level, heart rate, atmospheric sensing, angular rate, body orientation, MARG (magnetic, angular rate, and gravity), internal device sensing, blood oxygenation level, sun exposure, osmolality, piezoelectric skin measurements such as ultrasonic response changes, electrical parameter of dermis such as impedance, biosensing, sensing an enzyme, sensing an antibody, sensing a histamine, sensing a nucleic acid, any of the characteristics discussed for device 10016 air quality tracking, etc. Alternatively or in addition one or both of the sensors 2030, 2040 can be configured to gather data regarding a current of a motor used in delivering the drug. U.S. Pat. Pub. No. 2002/0014951 entitled "Remote Control For A Hospital Bed" published Feb. 7, 2002 and U.S. Pat. Pub. No. 2007/0251835 entitled "Subnetwork Synchronization And Variable Transmit Synchronization Techniques For A Wireless Medical Device Network" published Nov. 1, 2007 further discuss various sensors and are hereby incorporated by reference in their entireties. The sensors 2030, 2040 can either monitor the same physiological parameter or monitor different physiological parameters. Monitoring the same parameter may allow for confirmation of a condition, while monitoring different parameters may allow for more characteristics associated with the patient to be considered for drug delivery. While two sensors are illustrated in FIG. 13, the device 2002 can include only one sensor, such as sensor 2030, or can include three or more sensors. Any additional sensors can operate similarly to sensors 2030, 2040 and can also monitor various physiological characteristics. One or both of the sensors 2030, 2040 can be a biosensor, e.g., a device that includes a biological component and a transducer and that is configured to sense a biological element such as an enzyme, an antibody, a histamine, a nucleic acid, etc. The sensors 2030, 2040 can operate together as a sensor array or a dual sensor. The sensors 2030, 2040 are configured to sense their respective physiological characteristic(s), and the memory 2060 is configured to store therein data as pluralities of data points defining and/or representing the sensed characteristic(s). The communications interface 2099 is configured to communicate data indicative of the sensed information to the accessory 3002, e.g., to the communications interface 3099 thereof to allow the received information to be stored in the memory 3050 and analyzed by the processor 3060 to control drug delivery from the device 2002 using the algorithm 3052.

The accessory's at least one sensor 3030 is configured to sense one or more characteristics associated with a patient. The one or more characteristics can be physiological characteristics and/or situational characteristics of the patient. Various different physiological characteristics can be monitored, such as heart rate, blood pressure, perspiration level, etc. A number of different situational characteristics can be monitored, such as core temperature, time of day, date, patient activity level, altitude, GPS information, blood oxygenation level, sun exposure, osmolality, air quality, inflammatory response, one or more images and/or videos of the patient and/or an environment in which the patient is located (for example, to analyze food intake, to determine whether solid food or liquid is being consumed, to determine a location or activity of the patient, to determine a condition of the patient such as skin reaction, etc.), user-input data such as general well-being or a cycle time between flare ups of a particular ailment, etc. The at least one sensor 3030 is configured to sense the characteristic(s), with the memory 3050 storing gathered data as pluralities of data points defining and/or representing the sensed characteristic(s).

In at least some embodiments, one of the sensors 2030, 2040 of the drug administration device 2002 can in effect act as a primary sensor for the administration system 2000 that defines an operational range of closed loop control of the drug dosage and timing administration, and the at least one sensor 3030 of the accessory 3002 can act as a secondary sensor that provides patient feedback and is used to adjust the dosage amount, dosage timing, dosage location, etc. within the range defined by the primary sensor 2030. In other embodiments, the at least one sensor 3030 of the accessory 3002 can act as the primary sensor, and one of the sensors 2030, 2040 of the drug administration device 2002 can in effect act as the secondary sensor.

The processor 3060 of the accessory 3002 is configured to control delivery of the drug from the drug administration device 2002 to a patient based on the sensed data received from the device 2002 and, in at least some embodiments, additionally or alternatively based on data gathered by the accessory's at least one sensor 3030. Similar to that discussed above, the processor 3060 is configured to control the drug delivery by changing at least one variable parameter of the algorithm 3052 such as adjusting at least one variable parameter for a dosage of the drug, a timing between doses of the drug, a location of delivery of the drug, a concentration of the dose, actuating a set number or a continuous number of discrete doses, actuating continuous dosage, actuating an initial bolus dose and then subsequent sporadic or repeating smaller doses as needed, terminating dosage, skipping one or more doses, etc. The data received at the accessory 3002 from the device 2002 is in the form of pluralities of data points defining the sensed physiological characteristic(s) data of the patient. The processor 3060 can be configured to change the at least one variable parameter of the algorithm 3052 during the delivery of a dose such that the algorithm 3052 is changed in real time with the delivery of the dose (e.g., in real time with execution of the algorithm) and/or in real time with use of the drug administration device 1016 during performance of a surgical procedure, which may accommodate real time sensed conditions. The processor 3060 can be configured to change the at least one variable parameter of the algorithm 3052 before a start of the delivery of the dose, which may consume less memory and use fewer processing resources during algorithm 3052 execution than real time changing of the algorithm 3052.

The processor 3060 is configured to control drug delivery from the device 2002 through any of a variety of different mechanisms, such as by transmitting a command to the device 2002 using the communications interfaces 2099, 3099 with the device's processor 2060 executing the command to cause drug delivery (e.g., by providing a plurality of data points defining one or more instructions to the device 2002). Instead of the algorithm 3052 being stored at the accessory 3002, the algorithm for controlling drug delivery from the device 2002 can be stored at the device 2002, e.g., in the memory 2050 thereof. Similar to that discussed above, the accessory 3002 can be configured to cause at least one variable parameter of the algorithm stored at the device 2002 to be changed based on the data gathered by the device's at least one sensor 2030, 2040 and/or based on the data gathered by the accessory's at least one senor 3030, e.g., by transmitting a command to the device 2002 using the communications interfaces 2099, 3099 with the device's processor 3060 executing the command to change the at least one variable parameter as instructed. The algorithm being stored at the device 2002 instead of the accessory 3002 may help ensure that drug delivery occurs since delivery is controlled locally and can occur even if communication is broken between the device 2002 and accessory 3002, e.g., because the device 2002 and accessory 3002 are out of wireless communication range of one another, because of a network system problem, because of power loss at the accessory 3002, etc.

Figure 14:
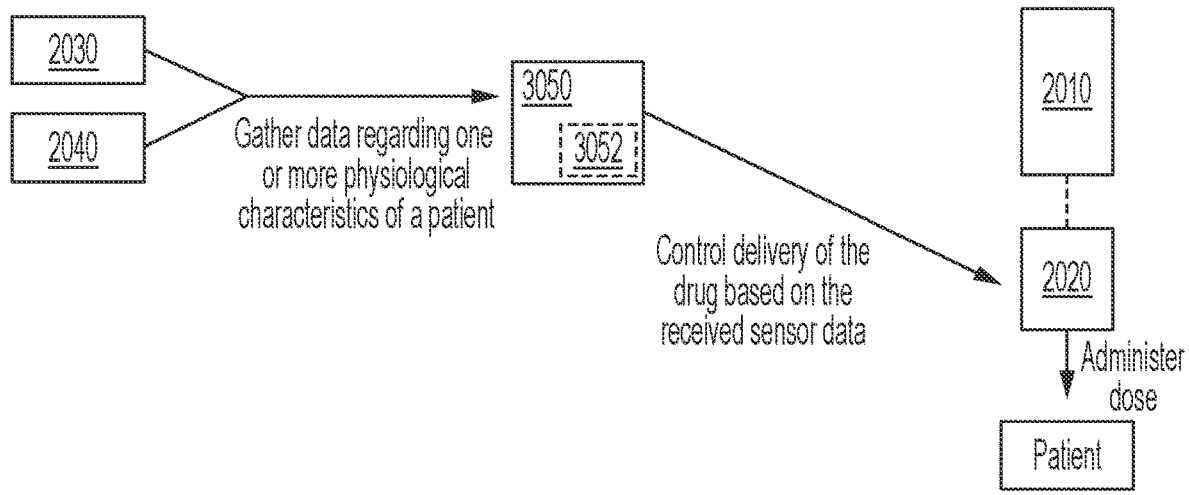
FIG. 14 is a flow diagram of the drug administration device of FIG. 13 in use.

FIG. 14 illustrates an embodiment of use of the drug administration device 2002 and accessory 3002. The use is similar to that discussed above with respect to FIG. 12 except that the processor 3050 of the accessory 3002 is shown as being involved in data analysis and control of dose delivery.

Various delivery types can be used from the drug administration device 2002, such as bolus or basal deliveries. For example, based on the severity of a hyper- or hypoglycemic reaction, a large bolus delivery can be used to prevent a body of a patient from further degrading. For another example, an automated system can adjust basal insulin target dose sizes based on a long term tracking of blood sugar, continuously adjust around a target basal level based on continuous monitoring, and then introduce bolus levels only for severe adjustments.

In at least some embodiments, the drug administration device 2002 is a smart drug administration device that performs some analysis on its own, with the accessory 3002 providing additional smart functionality to help improve dosage effectiveness, safety, and/or accuracy. For example, a smart drug administration device can be a smart insulin pump, such as Medtronic's MiniMed 670G, that allows for blood sugar detection such that the pump tracks a patient's continuous glucose level while adjusting for proximity between pump and sensor. For another example, a smart drug administration device can be a glucagon delivery device that treats hypoglycemia severity (defined by a blood sugar under 70) by injecting glucagon to raise glucose leveled to the desired basal level. For yet another example, a smart drug administration device can be an insulin delivery device that continuously adjusts an amount of insulin it delivers from one minute to the next based upon readings from the continuous glucose monitor.

The accessory 3002 can take a variety of different forms. The accessory 3002 can be used solely for helping to control drug delivery from the drug administration device 2002. Alternatively, the accessory 3002 can have an additional purpose that is different than that of drug delivery from the drug administration device 2002 and thus be multi-functional, for example as with the surgical hub.

Embodiments of accessories include surgical hubs, ear wigs, ear pieces, smart watches, fingernail sensors, digital collection patches (with or without direct skin contact), augmented reality or smart glasses, implantable or ingestible components, headbands, digitally connected devices to communicate weight, worn cameras (such as in smart glasses), carried cameras (such as in smartphones, mobile tablets, etc.), handheld diabetes management devices, smart mobility aid devices, tracking and monitoring mechanisms, etc. U.S. Pat. Pub. No. 2014/0081659 entitled "Systems And Methods For Surgical And Interventional Planning, Support, Post-Operative Follow-Up, And Functional Recovery Tracking" published Mar. 20, 2014 further describes various embodiments of tracking and monitoring mechanisms and is hereby incorporated by reference in its entirety. U.S. Pat. Pub. No. 2012/0095318 entitled "Handheld Diabetes Management Device With Bolus Calculator" published Apr. 19, 2012, which is hereby incorporated by reference in its entirety, further describes embodiments of handheld diabetes management devices. U.S. Pat. Pub. No. 2017/0172462 entitled "Multi-Functional Smart Mobility Aid Devices And Methods Of Use" filed on Jun. 22, 2017, which is hereby incorporated by reference in its entirety, further describes embodiments of smart mobility aid devices.

As mentioned above, image analysis can be used for capturing data in the environment around the patient, whether the patient is or is not in a surgical setting. For example, as will be appreciated by a person skilled in the art, image analysis can be used for meal detection, such as for confirmation that a meal is occurring; analysis of a meal itself such as volume or carbohydrate, protein, and fat content; image analysis of skin tone, injection site, and/or other anatomic structure to determine redness, inflammation, and/or other reaction; calculation of dosage amounts for drugs that are administered based on body area (for example, mg/m$^2$) such that images of the body of a patient can be used to calculate a dose in addition to any patient inputs such as weight, age, etc.; image analysis to provide relevant drug information through an interconnection between an image taken by a patient and any smart digital patient device that would allow the device to provide user information on the medication, dosage, timing, function, etc. U.S. Pat. Pub. No. 2012/0330684 entitled "Medication Verification And Dispensing" published Dec. 27, 2012, which is hereby incorporated by reference in its entirety, further describes image capturing devices. In response to detecting a meal, the accessory can be configured to adjust drug delivery from the drug administration device in communication with the accessory.

Figure 15:
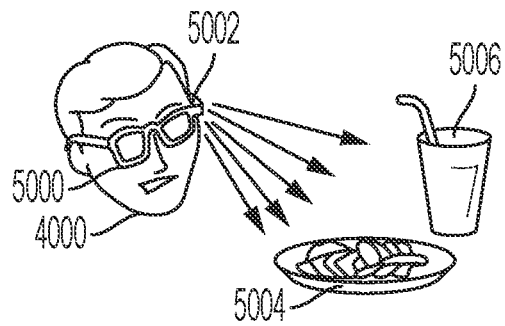
FIG. 15 is a perspective view of one embodiment of an accessory for use with a drug administration device in the form of glasses that can view a patient's food.

FIG. 15 illustrates an embodiment of an accessory 5000 in the form of smart glasses with a camera 5002 built therein. A user 4000 can wear the accessory 5000 like a normal pair of glasses, however the accessory 5000, e.g., a processor thereof, is configured to analyze images captured by the camera 5002 to visually identify a variety of types of information about a meal 5004 and/or a drink 5006 that the user 4000 is consuming, such as food type, food amount, amount of food remaining on plate, etc. U.S. Pat. Pub. No. 2011/0295337 entitled "Systems and Methods For Regulating Metabolic Hormone Producing Tissue" filed on Dec. 1, 2011, U.S. Pat. No. 8,696,616 entitled "Obesity Therapy And Heart Rate Variability" issued Apr. 15, 2014, U.S. Pat. No. 9,427,580 entitled "Devices And Methods For The Treatment Of Metabolic Disorders" issued Aug. 30, 2016, and U.S. Pat. No. 9,168,000 entitled "Meal Detection Devices And Methods" issued Oct. 27, 2015, which are hereby incorporated by reference in their entireties, further describe identifying types of information about a meal and/or a drink Detecting occurrences of eating/drinking with certainty is important for safety, efficacy, and cost, and can be combined with sensed information through situational awareness, as discussed above regarding the drug administration device 1016, to increase the accuracy of meal detection methods described herein. Images captured by the camera 5002 can be used to visually identify types of information and not in the meal 5004 and/or the drink 5006 context shown in FIG. 15, as mentioned above, such as for analysis of skin tone, injection site, and/or other anatomic structure to determine redness, inflammation, and/or other reaction.

As mentioned above, different sensor configurations and interactions can be used to produce primary and secondary measurements of physiological characteristic(s) of the patient, both in the drug administration device and/or the accessory. For example, sensors used can be modular sensor arrays, configurable sensor arrays, dual sensors that provide interactive sensing, dual cooperative remote sensing arrays, etc. In such examples, one or more sensor(s) configured to detect a physiologic response to drug administration in the patient can be positioned remotely to an injection site to prevent drug administration itself from interfering with the result. In addition, a second sensor array can be positioned close to the injection site and/or the drug administration device in order to determine acute local reaction and verify that the drug administration device has operated correctly.

Figure 16:
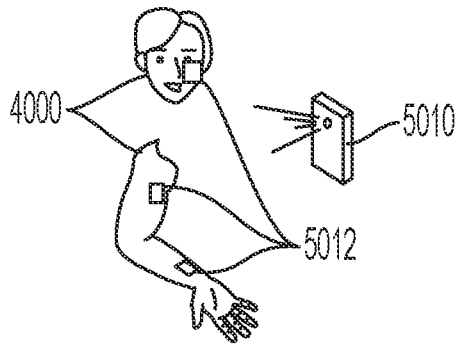
FIG. 16 is a perspective view of another embodiment of an accessory for use with a drug administration device in the form of a smartphone photographing a patient.
Figure 17:
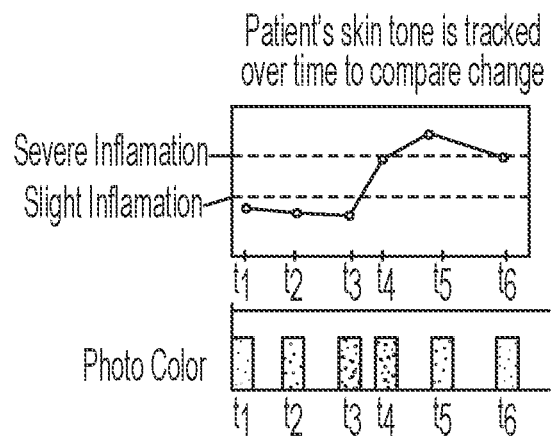
FIG. 17 is a graphical representation of the patient's skin of FIG. 16 photographed over time and measured for a reaction.
Figure 18:
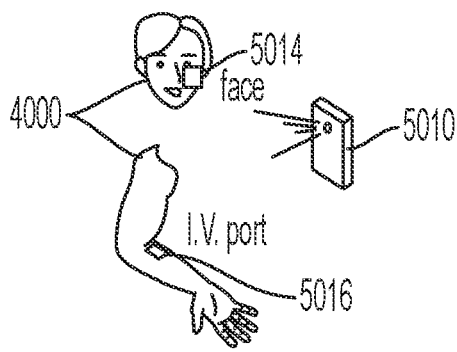
FIG. 18 is a perspective view of the accessory of FIG. 16 photographing the patient.
Figure 19:
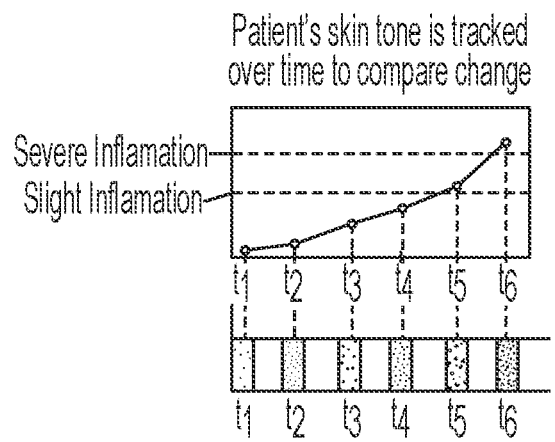
FIG. 19 is a graphical representation of the patient's skin of FIG. 18 photographed over time and measured for a reaction.

FIGS. 16 and 18 illustrate an embodiment of an accessory 5010 including a camera configured to gather images of the skin of a patient 4000 at various points on the patient's body. The accessory 5010 (and/or a computer system, such as a surgical hub, in communication with the accessory 5010) is configured to monitor the patient's skin tone, either at a single point or, as illustrated in FIG. 17 (for analysis of data gathered as shown in FIG. 16) and FIG. 19 (for analysis of data gathered as shown in FIG. 18), over time to track any possible reactions to a drug and/or to watch for any inflammation (either caused by administration of the drug or caused by a secondary source and for which the drug is being administered to treat) and, in response to detecting a drug reaction and/or inflammation, adjust drug delivery from the drug administration device in communication with the accessory 5010 (and/or the computer system). FIGS. 17 and 19 illustrate times $t_1$, $t_2$, $t_3$, $t_4$, $t_5$, and $t_6$ and a corresponding photo color chart of the patient's skin tone at each point in time (shown in grayscale in FIGS. 17 and 19). The broken lines traced on the graphs in FIGS. 17 and 19 represent slight inflammation and severe inflammation such that image analysis (either electronically by the system or manually by a care professional) allows tracking of inflammation and alerts, notification, pre-emptive action, responsive action, etc. in response to skin tone passing over the slight and/or the severe inflammation. FIG. 16 illustrates taking images at random points 5012 on the patient 4000. FIG. 18 illustrates taking images of the patient's face 5014 and at the point of administration of the drug in the form of an IV port 5016. The point of administration and the face 5014 of the patient 4000 can be useful areas to monitor for any adverse or beneficial reactions to an administered drug because the site of administration (the IV port 5016) is the first point of contact between the drug and the patient 4000 and human faces can be expressive of possible adverse reactions such as allergic reactions, etc.

Although FIGS. 16 and 18 show the camera as being part of a smartphone, the accessory configured to gather images can be a device other than a smartphone, such as an endoscope or other scoping device, a mobile tablet, a smartwatch, etc. Additionally, although the same accessory 5010 is shown gathering the images in FIGS. 16 and 18, two different accessories can gather the data of FIGS. 16 and 18.

In at least some implementations, drug delivery from a drug administration device is altered based on an awareness of a status of a patient, such as altering drug delivery based on at least one physiological characteristic of the patient and on at least one related physical characteristic of the patient. These implementations are similar to those discussed above with respect to drug delivery being altered based on one or more characteristics associated with the patient that are determined based on situational awareness of the patient except that the characteristics associated with the patient are determined based on at least one physiological characteristic of the patient and on at least one related physical characteristic of the patient. The implementations that take into account physiological characteristic(s) and physical characteristic(s) allow dosages to be varied based on a status of the patient, represented by the physiological and physical characteristics of the patient, to allow for personalized care, an adaptive drug administration process to improve patient care, and/or automatic dose adjustment to increase successful drug use. Various different physiological characteristics of the patient can be monitored, such as body temperature, heart rate, blood sugar level, blood pressure, perspiration level, etc. Various different physical characteristics of the patient can be monitored, such as temperature, metabolic demand, cognitive function, metabolic demand such as measured using at least one of food intake and BMR (basal metabolic rate), weight, one or more images and/or videos of the patient and/or an environment in which the patient is located (for example, to analyze food intake, to determine whether solid food or liquid is being consumed, to determine a location or activity of the patient, to determine a condition of the patient such as skin reaction, etc.), etc. Various different physical characteristics of the patient's environment can be monitored, such as atmospheric contaminant percentage, environmental temperature, etc.

Using the universal drug administration device 500 of FIG. 5 by way of example, the memory 97 can have stored therein the algorithm executable to administer a dose of drug to a patient, and the processor 96 can be configured to execute the algorithm to control delivery of a dose of the drug dispensed by the dispensing mechanism 20. The processor 96 can also be configured to use physiological data representative of at least one physiological characteristic of the patient and physical data representative of at least one physical characteristic of the patient to change at least one variable parameter of the algorithm such that a dose delivered subsequent to the changing of the at least one variable parameter will be controlled by execution of the changed algorithm. As mentioned above, a person skilled in the art will appreciate that the universal drug administration device 500 can be provided with a variety of the optional features described above, in a number of different combinations, e.g., not include any of the sensors 92, 94, 98 not being used by the processor 96 to change variable parameter(s) of the algorithm (and instead include sensor(s) to gather the needed physical and physiological characteristic data), not include packaging 35, not include user interface 80, etc. The processor 96 can be configured to change the at least one variable parameter of the algorithm during the delivery of a dose such that the algorithm is changed in real time with the delivery of the dose (e.g., in real time with execution of the algorithm) and/or in real time with use of the drug administration device 500 during performance of a surgical procedure, which may accommodate real time sensed conditions, or the processor 96 can be configured to change the at least one variable parameter of the algorithm before a start of the delivery of the dose, which may consume less memory and use fewer processing resources during algorithm execution than real time changing of the algorithm.

Using the universal drug administration device 1016 of FIG. 11 by way of another example, the use is similar to that discussed above regarding FIG. 5. The memory 1050 has stored therein the algorithm 1052, and the processor 1060 is configured to execute the algorithm 1052 to control delivery of a dose of the drug dispensed by the dispensing mechanism 1020. The processor 1060 is also configured to use physical characteristic data and physiological characteristic data gathered by at least two of the sensors 1030, 1040, 1045 and/or at least one external, separate sensor to change at least one variable parameter of the algorithm 1052 such that a dose delivered subsequent to the changing of the at least one variable parameter will be controlled by execution of the changed algorithm 1052. As mentioned above, a person skilled in the art will appreciate that the universal drug administration device 1016 can be provided with a variety of the optional features described above, in a number of different combinations, e.g., not include any of the sensors 1030, 1040, 1045 not being used by the processor 1060 to change variable parameter(s) of the algorithm 1052 (and instead include sensor(s) to gather the needed physical and physiological characteristic data), not include user interface 1080, etc. The processor 1060 can be configured to change the at least one variable parameter of the algorithm during the delivery of a dose such that the algorithm is changed in real time with the delivery of the dose (e.g., in real time with execution of the algorithm) and/or in real time with use of the drug administration device 1016 during performance of a surgical procedure, which may accommodate real time sensed conditions, or the processor 1060 can be configured to change the at least one variable parameter of the algorithm before a start of the delivery of the dose, which may consume less memory and use fewer processing resources during algorithm execution than real time changing of the algorithm.

In at least some embodiments, the at least one physiologic characteristic is directly tied to the treatment being administered by the drug administration device, and the drug administration device and/or a surgical hub in communication with the drug administration device is configured to use local or immediate processing to determine and adjust dosage to compensate for or overcome one or more current physical characteristic(s) being sensed. In such embodiments, as discussed herein, the at least one physiological characteristic is the primary characteristic that defines a range of responses of the drug administration device and the at least one variable parameter, and the one or more physical characteristics are secondary characteristics used to fine-tune or influence the drug administration device's dosage by changing the at least one variable parameter.

The implementations in which drug delivery from a drug administration device is altered based on an awareness of a status of a patient may allow for detection of any number of philological and/or physical characteristics. For example, detection of a physical characteristic of activity level, metabolism, and/or metabolic level can influence adjustment of dosage based on increased physiological demand. Generally, metabolism and metabolic rates are a blend between total energy expenditure and the energy balance between caloric intake and loss. Precise measurements of activity, caloric intake, fecal caloric output, oxygen consumption/ $CO_2$ generation, etc. can thus be used to inform metabolic activity. In such embodiments, metabolic activity can be the measured physiological characteristic, and one or more physical characteristics, such as activity, caloric intake, fecal caloric output, oxygen consumption/$CO_2$ generation, etc. can be measured to guide adjustment of drug administration based on the measured philological characteristic. In other embodiments, a combination of a variety of different measurements, such as activity measures, food intake measures, BMR, a physiologic measure such as body temperature or change in temperature, environmental temperature, and/or heart rate can be used as various approximations for real-time metabolic rates of a patient rather than attempting a more direct measurement. Metabolic rates are further discussed in, for example, Lam Y Y and Ravussin, E., "Analysis of energy metabolism in humans: A review of methodologies," Mol Metab. 2016 November; 5(11): 1057-1071 (available at <https://www.ncbi.nlm.nih.gov/pmc/articles/PMC5081410/>), which is hereby incorporated by reference in its entirety.

Drug delivery adjustment in implementations in which drug delivery from a drug administration device is altered based on an awareness of a status of a patient can be fully automatic, partially automatic and partially manual, or fully manual. Some degree of automatic dosage adjustment can be especially beneficial in situations when patients may have difficulty applying any recommended changes themselves caused by various patient circumstances, environmental cues, and/or physiological cues. For example, patient capacity and/or competency levels can be used as one or more means to determine between a fully automated response by the drug administration device and/or varying degrees of user partial control over dosage adjustment. For example, patients may normally be able to interact with the drug administration device(s) safely, but during various emergency situations, the patient's abilities may be impaired and automatic action may be required. Some degree of automatic dosage adjustment can be especially beneficial during performance of a surgical procedure on a patient when surgical personnel is handling multiple different tasks including monitoring and/or actuating drug delivery and when multiple characteristics of the patient are being monitored. The surgical personnel may therefore have difficulty applying any recommended changes themselves caused by various patient circumstances, environmental cues, and/or physiological cues. For example, one or more drugs may be planned pre-operatively for delivery to the patient at certain point(s) during performance of the surgical procedure, so allowing for automatic drug delivery from the drug administration device(s) may facilitate accurate execution of the pre-operative plan. For example, surgical personnel may normally be able to interact with the drug administration device(s) safely, but during various emergency situations, their abilities may be impaired and automatic action may be required.

Thus, drug administration devices in at least some embodiments herein can be partially automatic, allowing patient and/or doctor (or other medical personnel) control or override of automatic actions in various situations while providing automatic actions that cannot be overridden by a patient and/or doctor (or other medical personnel) in various emergency situations. The notifications in at least some embodiments can have priorities or degrees to them, becoming more insistent as a situation becomes more dangerous for the patient. With certain drug administration devices, care providers, surgical personnel, and/or emergency personnel may be automatically alerted when certain major alarms are sounded. Additionally, risk-based assessments of treatment can become more aggressive over time if a patient fails to take appropriate de-escalation actions and/or the drug administration device detects an apparent lack of patient ability to help themselves.

A variety of other patient circumstances may lend themselves to some degree of partial or full automation for dosage adjustments. For example, a pediatric patient may not yet understand or be able to manipulate the drug administration device in a safe way, the patient may suffer from dementia while having a disease requiring an injectable or oral medication and cannot understand the drug administration device, patients may suffer from various mental or psychiatric disorders that affect their ability to use the drug administration device and/or to perceive gradual symptom escalation, patients may have a hard time administering the drug and need to rely on automatic actions by the drug administration device, etc. In at least some situations, recommended treatments can allow for drug administration device adjustments that simply make more sense to automate to help with compliance, such as with injectables that may be various forms of pumps or other drug administration devices almost always worn by a patient. For example, various diabetes side effects can increase a difficulty or inhibit a patient's ability to administer an adjusted dosage due to age, dexterity, onset of various complicating situations (such as hyper- or hypoglycemia), etc.

Similar to the accessory discussed above, at least some embodiments of drug administration devices can be configured to automatically adjust dosage over time based on a patient's weight, such as for a pediatric patient since weight tends to fluctuate more for pediatric patients as they are in the process of growing. Weight measurements can be taken in a variety of ways, such as from a scale in the home that automatically communicates the measured weight to the drug administration device or by analyzing images as discussed above. Warnings of weight change can also be provided prior to any change to a dosage actually occurring. In some situations, independent verification and/or approval by a patient's care provider may be required before initiating any change. For example, parents and/or doctors can report a pediatric patient's weight when possible, and the dosing algorithm for the patient can then update automatically with the new weight information. Any changes can be made directly on the drug administration device and/or can be made remotely.

In at least some embodiments in which drug delivery from a drug administration device is altered based on an awareness of a status of a patient, such as altering drug delivery based on at least one physiological characteristic of the patient and on at least one related physical characteristic of the patient, situational awareness of the patient can also be considered in altering the drug delivery, similar to that discussed above, for example, with respect to the drug administration device 1016 of FIG. 11. For example, additionally taking into account situational awareness can allow a drug administration device and/or a surgical hub in communication with the drug administration device to refine sensed data, mitigate errors, eliminate or reduce inaccurate outliers, and/or otherwise selectively affect the drug administration device to improve the device's understanding of the physiological reactions of the patient leading up to or after a dosage administration. Thus, one or more sensors can act as adaptive sensing arrays based on a situational awareness of the patient and/or the drug administration device.

Figure 20:
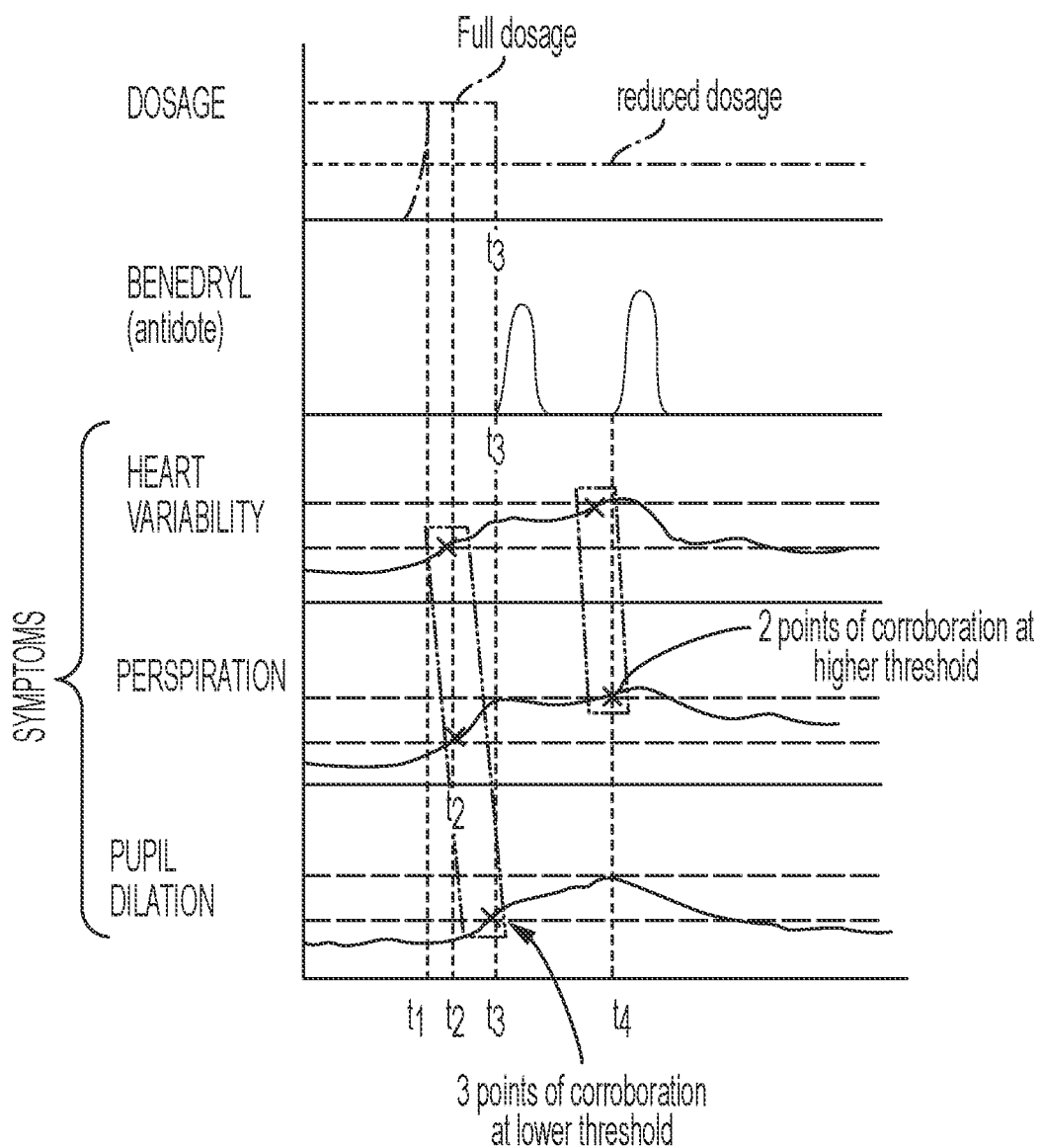
FIG. 20 is a graphical representation of the effects on a patient over time of another embodiment of a drug administration device in use.

FIG. 20 illustrates an embodiment of an adverse reaction to a drug administration device in the form of an infusion device that delivers a dosage of a drug to a patient at time $t_1$. Along with various physiological characteristic(s) of the patient and physical characteristic(s) of the patient that the drug administration device tracks to determine appropriate dosages of the drug, the drug administration device and/or a surgical hub in communication with the drug administration device also monitors for an allergic reaction to the drug by the patient by measuring physical characteristics and physiological characteristics that can indicate an adverse reaction, such as heart rate variability, perspiration, and/or pupil dilation. At time $t_2$, heart rate variability, perspiration, and pupil dilation all increase measurably, crossing over minor warning thresholds as illustrated and suggesting a possible adverse reaction to the drug. Thus, at time $t_3$, the dosage of the drug is reduced and a bolus of a medication, e.g., Benadryl, is administered by the device at a lower dosage to counteract the patient reaction. At time $t_4$, heart rate variability, perspiration, and pupil dilation all continue to increase, and heart rate variability and perspiration both cross over major warning thresholds. The drug administration device thus delivers a second larger bolus of the medication, at which point heart rate variability, perspiration, and pupil dilation all begin to decrease to more normal or baseline values. At this point in time, the patient's reaction is under control, so the original drug can continue to be delivered at the reduced dosage.

Figure 21:
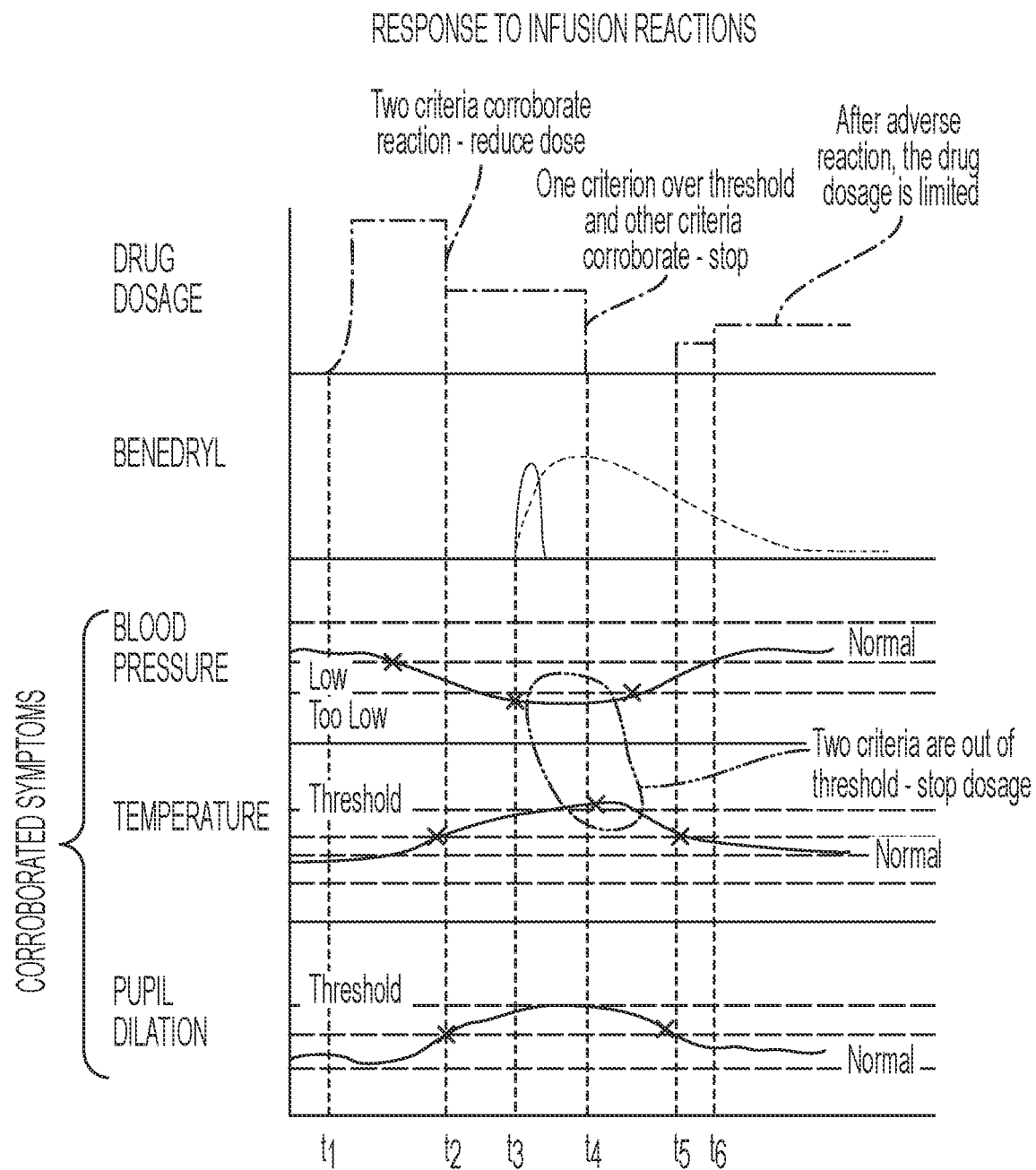
FIG. 21 is a graphical representation of the effects on a patient over time of another embodiment of a drug administration device in use.

If the patient does not react effectively to drug administration, dosages of the original drug can be terminated entirely and restated at lower, stepped values only once the various symptoms of the adverse reaction have abated. For example, FIG. 21 illustrates a graph similar to the graph of FIG. 20 and shows measured blood pressure, temperature, and pupil dilation. At time $t_1$, a dosage of the drug begins to be administered to the patient. At time $t_2$, temperature and pupil dilation cross warning thresholds to indicate a possible adverse reaction, and the dosage is reduced. At time $t_3$, a dose of the medication is administered because blood pressure has gone down but both temperature and pupil dilation have continued to increase. At time $t_4$, pupil dilation is still elevated while temperature has crossed over a major threshold and blood pressure has decreased to such an extent that it has crossed over a lower threshold and is now too low. As such, drug dosage is stopped entirely. At $t_5$, the blood pressure, temperature, and pupil dilation have begun to return to normal levels, so the drug is again administered to the patient. However, the dosage is further reduced. At time $t_6$ when there has not been a significant increase in adverse reaction indications from the blood pressure, temperature, and pupil dilation, the dosage is again increased slightly and maintained at a lower level for the time being.

Figure 22:
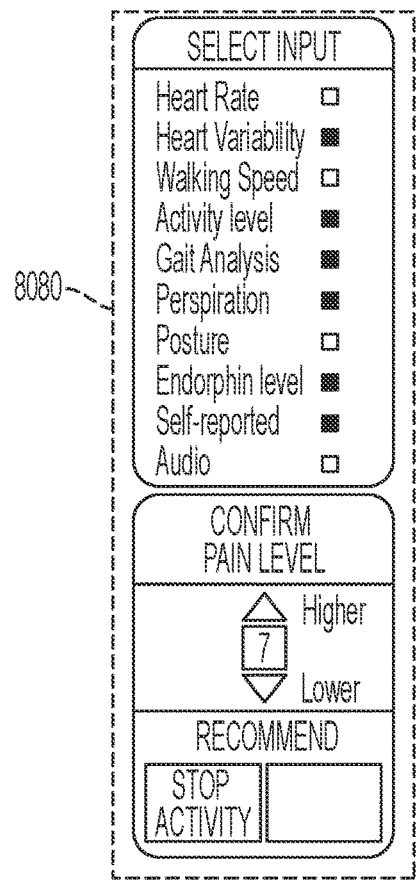
FIG. 22 is a front view of a user interface of another embodiment of a drug administration device.

In at least some embodiments, patients and/or medical personnel can choose or opt in to monitoring from one or more sensors in a drug administration device and/or one or more external, separate sensors. For example, FIG. 22 illustrates one embodiment of a user interface 8080 of a drug administration device that allows a patient, either on the device itself or via other means such as a patient app associated with the device, to opt into monitoring using one or more sensors. In other embodiments, the user interface 8080 can instead or additionally be provided elsewhere, such as on a user interface of a surgical hub in communication with the drug administration device.

Figure 23:
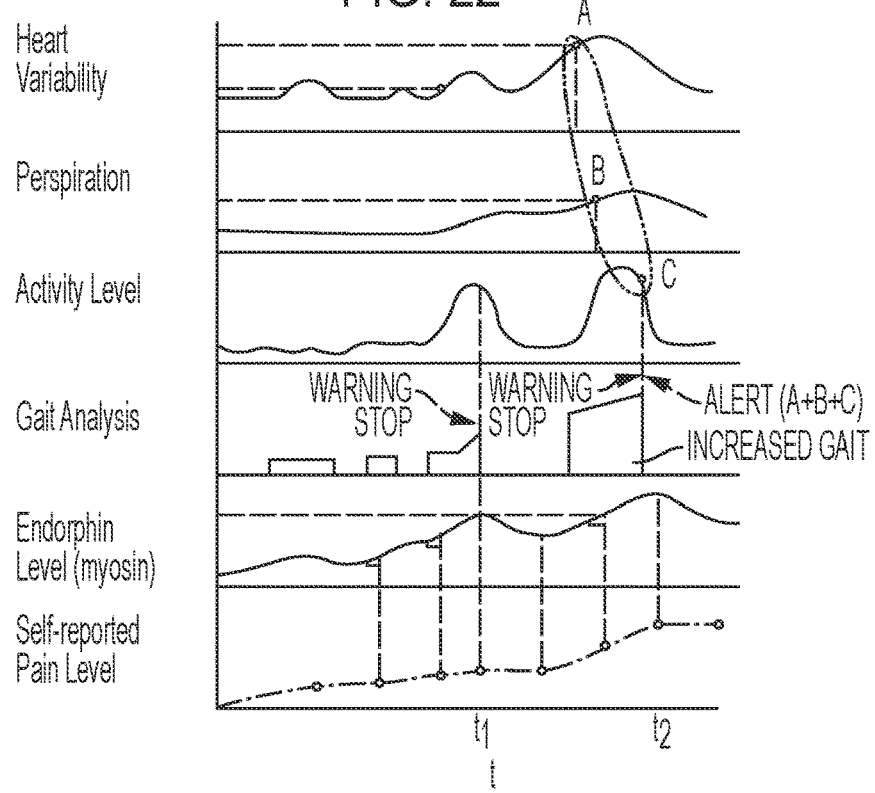
FIG. 23 is a graphical representation of the effects on a patient over time of the drug administration device of FIG. 22 in use.

As the one or more sensors monitor the patient as shown in FIG. 23, the one or more sensors can detect possible or likely early onset of joint pain, such as at $t_1$ and $t_2$. For example, a minor warning might be prompted at time $t_1$ when readings from an activity level sensor and a gate analysis sensor indicate that physical activity may be too much for the patient and continued activity will prompt joint pain. As the patient continues activity, time point A on FIG. 23 indicates crossing over a major threshold for heart rate variability, time point B indicates crossing over a major threshold for perspiration, and time point C indicates crossing over a major threshold for activity level, at which point an alert is sounded when all three conditions A, B, C are met at time $t_2$ to indicate possible onset of severe joint pain. At this point, the drug administration device, a patient app, and/or the surgical hub can prompt the patient and/or other user to enter a pain score, for example by using the user interface 8080, so that the drug administration device and any treating care provider can be better informed of the results of treatment. The situational awareness measurements discussed herein can be incorporated into any of the drug administration devices above to provide increased understanding of treatments and results and increased personalization of care.

As discussed above, some form of food intake and/or meal detection can be important when providing recommendations to a patient and when adjusting dosages. While some exemplary meal detection approaches are discussed above, such as image analysis, various drug administration devices can also use combinations of inputs from various physiological and/or physical sensors to confirm that a meal event has occurred and that it is significant enough to trigger a desired response in the patient. For example, analysis of heart rate variability (HRV), image analysis, gastric pH, a LINX Reflux Management device, etc. can each be used independently or in some combination to provide a more accurate detection of meal consumption. Providing various redundant measures may help minimize errors in meal detection.

Surgical Hub Control of Drug Administration Devices

As mentioned above, a surgical hub can be configured to communicate with one or more modular devices. Modular devices include the modules (as described in connection with FIGS. 3 and 9, for example) that are receivable within a surgical hub and the surgical devices or instruments that can be connected to the various modules. The modular devices can include, for example, intelligent drug administration devices, intelligent surgical instruments, medical imaging devices, suction/irrigation devices, smoke evacuators, energy generators, ventilators, and insufflators. Various operations of the modular devices described herein can be controlled by one or more control algorithms. The control algorithms can be executed on the modular device itself, on the surgical hub to which the particular modular device is paired, or on both the modular device and the surgical hub (e.g., via a distributed computing architecture). In some exemplifications, the modular devices' control algorithms control the modular devices based on data sensed by the modular device itself (i.e., by sensors in, on, or connected to the modular device). This data can be related to the patient being operated on (e.g., tissue properties, insufflation pressure, physiological parameters, etc.) or the modular device itself (e.g., the rate at which a knife is being advanced, motor current, energy levels, volume of drug in a drug holder, drug delivery rate, etc.). For example, a control algorithm for a surgical stapling and cutting instrument can control the rate at which the instrument's motor drives its knife through tissue according to resistance encountered by the knife as it advances. Control algorithms for other modular devices, including surgical instruments, are described further in previously mentioned U.S. Pat. Pub. No. 2019/0201114 entitled "Adaptive Control Program Updates For Surgical Hubs" filed Mar. 29, 2018. For another example, a control algorithm for a drug administration device can control a dosage amount to be delivered in a single dose delivered to a patient. Control algorithms for drug administration devices are described further above.

Although an "intelligent" modular device including control algorithms that respond to sensed data can be an improvement over a "dumb" modular device that operates without accounting for sensed data, if the modular device's control program does not adapt or update over time in response to collected data, then the modular devices may continue to repeat errors or otherwise perform suboptimally. One solution includes transmitting operational data collected by the modular devices in combination with the outcomes of each procedure (or step thereof) to an analytics system. In one exemplification, the procedural outcomes can be inferred by a situational awareness system of a surgical hub to which the modular devices are paired, as described further in U.S. Pat. Pub. No. 2019/0201140 entitled "Surgical Hub Situational Awareness" filed Mar. 29, 2018, which is hereby incorporated by reference in its entirety. The analytics system can analyze the data aggregated from a set of modular devices or a particular type of modular device to determine under what conditions the control programs of the analyzed modular devices are controlling the modular devices suboptimally (e.g., if there are repeated faults or errors in the control program or if an alternative algorithm performs in a superior manner) or under what conditions medical personnel are utilizing the modular devices suboptimally. The analytics system can then generate an update to fix or improve the modular devices' control programs. Different types of modular devices can be controlled by different control programs; therefore, the control program updates can be specific to the type of modular device that the analytics system determines is performing suboptimally. The analytics system can then push the update to the appropriate modular devices connected to the analytics system through the surgical hubs.

Figure 24:
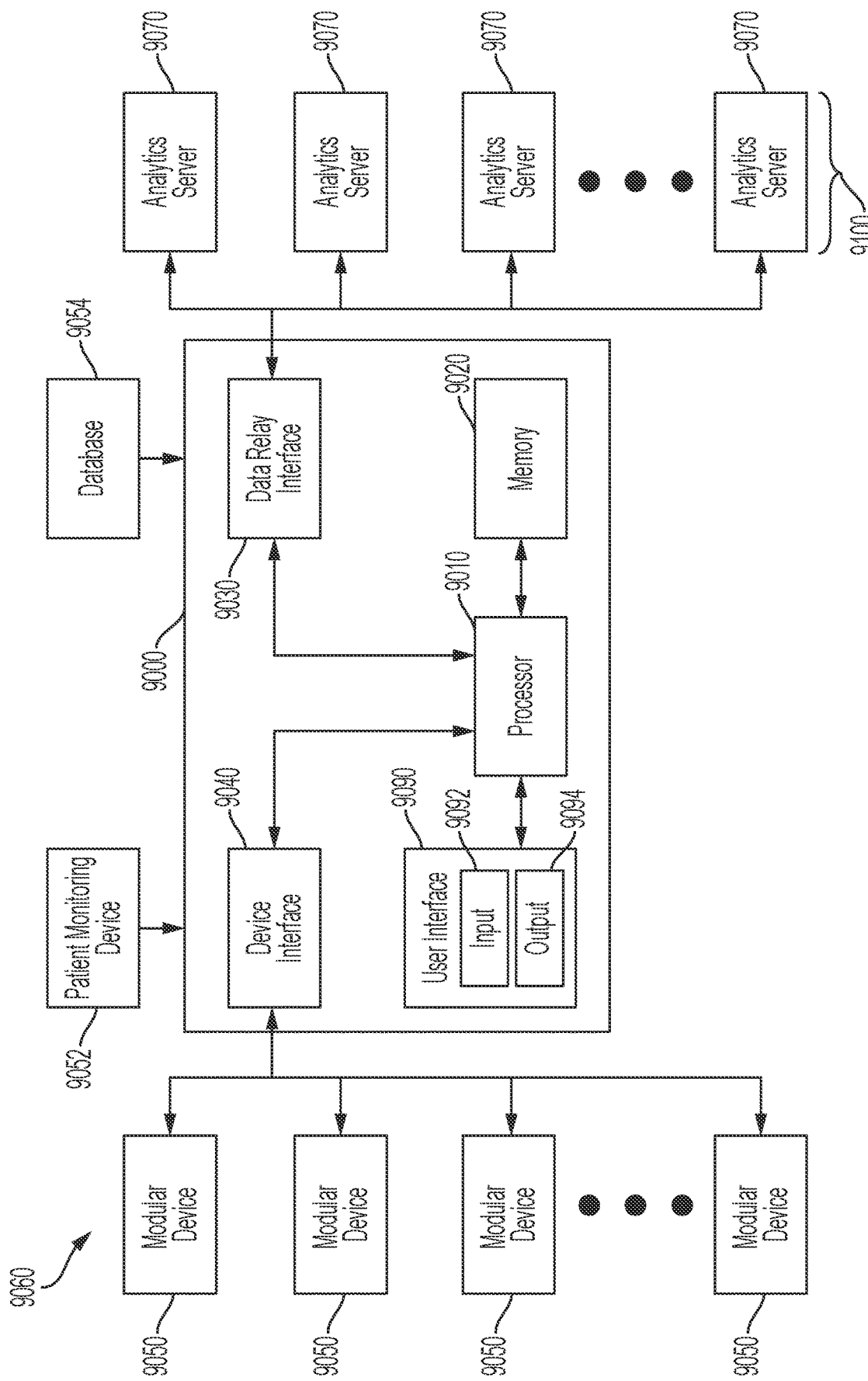
FIG. 24 is a schematic view of one embodiment of a computer-implemented interactive surgical system that is configured to adaptively generate control program updates for modular devices.

FIG. 24 illustrates one embodiment of a computer-implemented adaptive surgical system 9060 that is configured to adaptively generate control program updates for modular devices 9050, such as any of the drug administration devices described above. In this illustrated embodiment, the surgical system 9060 includes a surgical hub 9000, multiple modular devices 9050 communicably coupled to the surgical hub 9000, and an analytics system 9100 communicably coupled to the surgical hub 9000. Although a single surgical hub 9000 is shown in FIG. 24, the surgical system 9060 can include any number of surgical hubs 9000, which can be connected to form a network of surgical hubs 9000 that are communicably coupled to the analytics system 9010. The surgical hub 9000, and any additional surgical hubs, are generally configured and used similar to the surgical hubs discussed above.

In this illustrated embodiment, the surgical hub 9000 includes a memory 9020, a processor 9010 coupled to the memory 9020 and configured to execute instructions stored on the memory 9020, a data relay interface 9030 through which data is configured to be transmitted to the analytics system 9100, a user interface 9090 having an input device 9092 (e.g., a capacitive touchscreen, a keyboard, etc.) configured to receive inputs from a user, and an output device 9094 (e.g., a display screen, a speaker, etc.) configured to provide outputs to a user. Outputs can include data from a query input by the user, suggestions for products or mixes of products to use in a given procedure, warning sounds, and/or instructions for actions to be carried out before, during, or after surgical procedures. The surgical hub 9000 also includes an interface 9040 configured to communicably couple the modular devices 9050 to the surgical hub 9000. The interface 9040 also includes a communications interfaces, such as a transceiver, that is configured to communicably connect to the modular device 9050 via a wireless communication protocol. The modular devices 9050 can include any combination of, for example, drug administration devices surgical stapling and cutting instruments, electrosurgical instruments, ultrasonic instruments, insufflators, respirators, and display screens. The surgical hub 9000 is also communicably coupled to one or more patient monitoring devices 9052, such as EKG monitors or BP monitors. The surgical hub 9000 is also communicably coupled to one or more databases 9054 or external computer systems, such as an electronic medical records (EMR) database of a medical facility at which the surgical hub 9000 is located, which is the same medical facility at which the surgical hub 9000 can be used during performance of a surgical procedure.

When the modular devices 9050 are connected to the surgical hub 9000, the surgical hub 9000 can sense or receive perioperative data from the modular devices 9050 and then associate the received perioperative data with surgical procedural outcome data. The perioperative data indicates how the modular devices 9050 were controlled (independently and/or by the surgical hub 9000 or other surgical hub) during the course of a surgical procedure. The procedural outcome data includes data associated with a result from the surgical procedure (or a step thereof), which can include whether the surgical procedure (or a step thereof) had a positive or negative outcome. For example, the outcome data can include whether a patient suffered from postoperative complications from a particular procedure, whether there was leakage (e.g., bleeding or air leakage) at a particular staple or incision line, whether the patient experienced an adverse drug reaction, etc. The surgical hub 9000 can obtain the surgical procedural outcome data by receiving the data from an external source (e.g., from an EMR database 9054 and/or other source), by directly detecting the outcome (e.g., via one of the connected modular devices 9050), or inferring the occurrence of the outcomes through a situational awareness system. For example, data regarding postoperative complications could be retrieved from the EMR database 9054, and data regarding staple or incision line leakages and/or adverse drug reaction could be directly detected or inferred by a situational awareness system. The surgical procedural outcome data can be inferred by a situational awareness system from data received from a variety of data sources, including the modular devices 9050 themselves, the patient monitoring device 9052, and the databases 9054 to which the surgical hub 9000 is connected.

The surgical hub 9000 can transmit the associated modular device 9050 data and outcome data to the analytics system 9100 for processing thereon. By transmitting both the perioperative data indicating how the modular devices 9050 are controlled and the procedural outcome data, the analytics system 9100 can correlate the different manners of controlling the modular devices 9050 with surgical outcomes for the particular procedure type. As in this illustrated embodiment, the analytics system 9100 can include a network of analytics servers 9070 that are configured to receive data from the surgical hubs 9000. Each of the analytics servers 9070 can include a memory and a processor coupled to the memory and configured to execute instructions stored on the memory to analyze the received data. The analytics servers 9070 can be connected in a distributed computing architecture and/or can utilize a cloud computing architecture. Based on this paired data, the analytics system 9100 can then learn optimal or preferred operating parameters for the various types of modular devices 9050, generate adjustments to the control programs of the modular devices 9050 in the field, and then transmit (or "push") updates to one or more of the modular devices' 9050 control programs.

Additional detail regarding the computer-implemented interactive surgical system 9060, including the surgical hub 9000 and various modular devices 9050 connectable thereto, are further described in previously mentioned U.S. Pat. Pub. No. 2019/0200844 entitled "Method Of Hub Communication, Processing, Storage And Display" filed Dec. 4, 2018 and U.S. Pat. Pub. No. 2019/0201114 entitled "Adaptive Control Program Updates For Surgical Hubs" filed Mar. 29, 2018.

Figure 25:
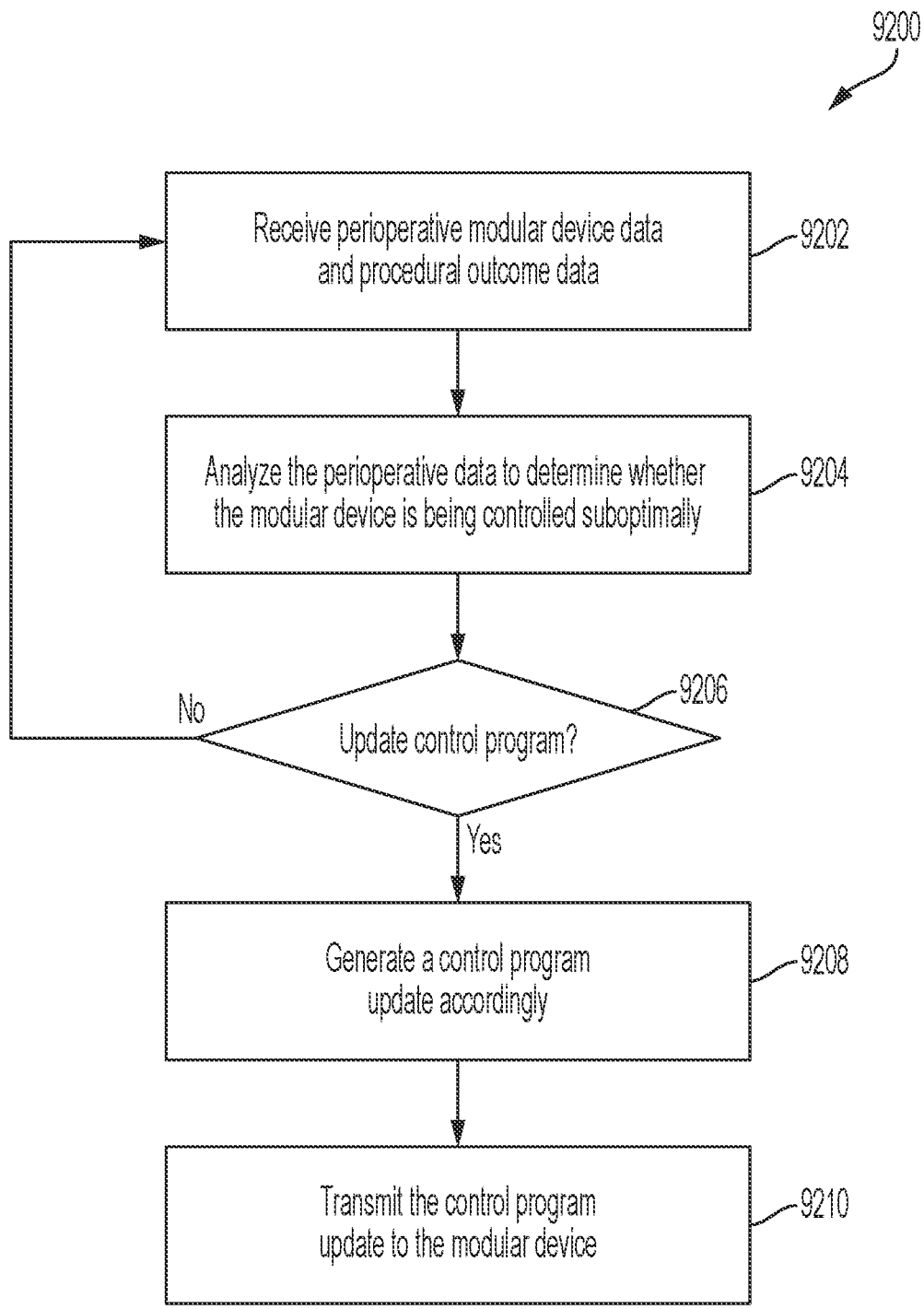
FIG. 25 is a logic flow diagram of one embodiment of a process for updating a control program of a modular device.

FIG. 25 illustrates one embodiment of a process 9200 for updating the control program of a modular device 9050. The process 9200 can be executed by, for example, one or more processors of the analytics servers 9070 of the analytics system 9100. As mentioned above, the analytics system 9100 can be a cloud computing system. For economy, the following description of the process 9200 is described as being executed by the analytics system 9100; however, it should be understood that the analytics system 9100 includes processor(s) and/or control circuit(s) that are executing the process 9200.

The analytics system 9100 receives 9202 modular device 9050 perioperative data and surgical procedural outcome data from one or more of the surgical hubs 9000 that are communicably connected to the analytics system 9100. The perioperative data includes preoperative data, intraoperative data, and/or postoperative data detected by a modular device 9050 in association with a given surgical procedure. For modular devices 9050 or particular functions of modular devices 9050 that are manually controlled, the perioperative data indicates the manner in which a surgical staff member operated the modular devices 9050. For modular devices 9050 or particular functions of modular devices 9050 that are controlled by the modular devices' control programs, the perioperative data indicates the manner in which the control programs operated the modular devices 9050. The manner in which the modular devices 9050 function under particular sets of conditions (either due to manual control or control by the modular devices' 9050 control programs) can be referred to as the "operational behavior" exhibited by the modular device 9050. The modular device 9050 perioperative data includes any combination of data regarding the state of the modular device 9050 (e.g., the force to fire or force to close for a surgical stapling and cutting instrument, the power output for an electrosurgical or ultrasonic instrument, for the dosage amount for a drug administration device, the force to actuate a trigger for a drug administration device, etc.), tissue data measured by the modular device 9050 (e.g., impedance, thickness, stiffness, etc.), and other data that can be detected by a modular device 9050. The perioperative data indicates the manner in which the modular devices 9050 were programmed to operate or were manually controlled during the course of a surgical procedure because it indicates how the modular devices 9050 functioned in response to various detected conditions.

The surgical procedural outcome data includes data pertaining to an overall outcome of a surgical procedure (e.g., whether there was a complication during the surgical procedure) and/or data pertaining to an outcome of a specific step within a surgical procedure (e.g., whether a particular staple line bled or leaked, whether a patient experienced an allergic or other adverse reaction to a drug delivered during the surgical procedure, etc.). The procedural outcome data can, for example, be directly detected by the modular devices 9050 using one or more sensors, directly detected by the surgical hub 9000 using one or more sensors, determined or inferred by a situational awareness system of the surgical hub 9000, and/or retrieved from a database 9054 (e.g., an EMR database and/or other database) by the surgical hub 9000 or the analytics system 9100. Determining or inferring procedural outcome data is further described, for example, in previously mentioned U.S. Pat. Pub. No. 2019/0201140 entitled "Surgical Hub Situational Awareness" filed Mar. 29, 2018. The procedural outcome data can include whether each outcome represented by the data was a positive or negative result. Whether each outcome was positive or negative can be determined by the modular devices 9050 themselves and included in the perioperative data transmitted to the one or more surgical hubs 9000 or determined or inferred by the one or more surgical hubs 9000 from the received perioperative data. For example, the procedural outcome data for a staple line that bled could include that the bleeding represented a negative outcome. Similarly, the procedural outcome data for a staple line that did not bleed could include that the lack of bleeding represented a positive outcome. For another example, the procedural outcome data for an administered drug that causes an allergic reaction in the patient could include that the drug administration represented a negative outcome. Similarly, the procedural outcome data for an administered drug that did not cause an allergic reaction in the patient could include that the drug administration represented a positive outcome. The analytics system 9100 can be configured to determine whether a procedural outcome is a positive or negative outcome based upon the received procedural outcome data. Correlating the modular device 9050 data to positive or negative procedural outcomes allows the analytics system 9100 to determine whether a control program update should be generated 9208.

Upon the analytics system 9100 receiving 9202 the data, the analytics system 9100 analyzes the modular device 9050 and procedural outcome data to determine 9204 whether the modular devices 9050 are being utilized suboptimally in connection with the particular procedure or the particular step of the procedure. A modular device 9050 can be controlled suboptimally if the particular manner in which the modular device 9050 is being controlled is repeatedly causing an error or if an alternative manner of controlling the modular device 9050 is superior under the same conditions. The analytics system 9100 can thus determine whether a modular device 9050 is being controlled suboptimally (either manually or by its control program) by comparing the rate of positive and/or negative outcomes produced by the modular device 9050 relative to set thresholds or the performance of other modular devices 9050 of the same type and/or to modular devices 9050 in the form of drug administration devices that deliver a same drug but may or may not be the same type of drug administration device.

For example, the analytics system 9100 can determine whether a type of modular device 9050 is being operated suboptimally if the rate of negative procedural outcomes produced by the modular device 9050 under a particular set of conditions in association with a particular operational behavior exceeds an average or threshold level. For example, the analytics system 9100 can analyze 9204 whether a control program for a surgical stapling instrument that dictates a particular force to fire (or ranges of forces to fire) is suboptimal for a particular tissue thickness and tissue type. If the analytics system 9100 determines that the instrument generates an abnormally high rate of leaky staple lines when fired at the particular force (e.g., causing the staples to be malformed, not fully penetrate the tissue, or tear the tissue) relative to an average or threshold staple line leakage rate, then the analytics system 9100 can determine that the control program for the surgical stapling instrument is performing suboptimally given the tissue conditions. For another example, the analytics system 9100 can analyze 9204 whether a control program for a drug administration device that dictates a time between dose deliveries is suboptimal for a particular type of surgery. If the analytics system 9100 determines that the drug administration device is delivering an abnormally high number of doses relative to an average or threshold time between dose deliveries for that drug and/or that type of drug administration device, then the analytics system 9100 can determine that the control program for the drug administration device is performing suboptimally given the surgery type. For yet another example, the analytics system 9100 can analyze 9204 whether a control program for a drug administration device that dictates a dosage amount is suboptimal for a particular patient weight. If the analytics system 9100 determines that the drug administration device is delivering an abnormally high number of doses during a surgical procedure relative to an average or threshold number of deliveries for that drug and/or that type of drug administration device during a surgical procedure, then the analytics system 9100 can determine that the control program for the drug administration device is performing suboptimally given the patient's weight, e.g., that the patient may need higher doses and/or more dose deliveries.

For another example, the analytics system 9100 can determine whether a type of modular device 9050 is being operated suboptimally if the rate of positive outcomes produced by an alternative manner of control under a particular set of conditions in association with a particular operational behavior exceeds the rate of positive outcomes generated by the analyzed manner of control under the same conditions. In other words, if one subpopulation of the type of modular device 9050 exhibits a first operational behavior under a certain set of conditions and a second subpopulation of the same type of modular device 9050 exhibits a second operational behavior under the same set of conditions, then the analytics system 9100 can determine whether to update the control programs of the modular devices 9050 according to whether the first or second operational behavior is more highly correlated to a positive procedural outcome. For example, the analytics system 9100 can analyze 9204 whether a control program for a radiofrequency (RF) electrosurgical or ultrasonic instrument that dictates a particular energy level is suboptimal for a particular tissue type and environmental conditions. If the analytics system 9100 determines that a first energy level given a set of tissue conditions and environmental conditions (e.g., the instrument being located in a liquid-filled environment, as in an arthroscopic procedure) produces a lower rate of hemostasis than a second energy level, then the analytics system 9100 can determine that the control program for the electrosurgical or ultrasonic instrument dictating the first energy level is performing suboptimally for the given tissue and environmental conditions. For another example, the analytics system 9100 can analyze 9204 whether a control program for a drug administration device that dictates a particular time between dose deliveries is suboptimal for a particular blood pressure level, heart rate, oxygen level, and/or other patient condition. If the analytics system 9100 determines that a first time between dose deliveries given a set of relevant patient measurements produces more adverse patient reactions (e.g., increasing the patient's heart rate, increasing the patient's blood pressure, causing difficulty in breathing, etc.) than a second, greater time between dose deliveries, then the analytics system 9100 can determine that the control program for the drug administration device dictating the first time between dose deliveries is performing suboptimally for the given patient condition(s).

After analyzing 9204 the data, the analytics system 9100 determines 9206 whether to update the control program. If the analytics system 9100 determines that the modular device 9050 is not being controlled suboptimally, then the process 9200 continues along the NO branch shown in FIG. 25, and the analytics system 9100 continues analyzing 9204 received 9202 data, as described above. If the analytics system 9100 determines that the modular device 9050 is being controlling suboptimally, then the process 9200 continues along the YES branch shown in FIG. 25, and the analytics system 9100 generates 9208 a control program update. The generated 9208 control program update includes, for example a new value for at least one variable parameter of the control program. In another example, the generated 9208 control program update includes a new version of the control program for the particular type of modular device 9050 to overwrite the prior version or a patch that partially overwrites or supplements the prior version.

The type of control program update that is generated 9208 by the analytics system 9100 depends upon the particular suboptimal behavior exhibited by the modular device 9050 that is identified by the analytics system 9100. For example, if the analytics system 9100 determines that a particular force to fire a surgical stapling instrument results in an increased rate of leaking staple lines, then the analytics system 9100 can generate 9208 a control program update that adjusts the force to fire from a first value to a second value that corresponds to a higher rate of non-leaking staple lines or a lower rate of leaking staple lines. For another example, if the analytics system 9100 determines that a particular energy level for an electrosurgical or ultrasonic instrument produces a low rate of hemostasis when the instrument is used in a liquid-filled environment (e.g., due to the energy dissipating effects of the liquid), then the analytics system 9100 can generate 9208 a control program update that adjusts the energy level of the instrument when it is utilized in surgical procedures where the instrument will be immersed in liquid. For yet another example, if the analytics system 9100 determines that a particular time between dose deliveries for a drug administration device results in an increased rate and/or intensity of adverse patient reactions, then the analytics system 9100 can generate 9208 a control program update that adjusts the time between dose deliveries from a first value to a second, lower value to try to reduce the rate and/or intensity of adverse patient reactions. For still another example, if the analytics system 9100 determines that a particular dosage amount for a drug delivered from a drug administration device results in an increased rate and/or intensity of adverse patient reactions, then the analytics system 9100 can generate 9208 a control program update that adjusts the dosage amount from a first value to a second, lower value to try to reduce the rate and/or intensity of adverse patient reactions.

The type of control program update that is generated 9208 by the analytics system 9100 also depends upon whether the suboptimal behavior exhibited by the modular device 9050 is caused by manual control or control by the control program of the modular device 9050. If the suboptimal behavior is caused by manual control, the control program update can be configured to provide warnings, recommendations, and/or feedback to the module device's one or more users, e.g., via email, via text message, via display on a user interface of the module device, etc., based upon the manner in which the one or more users are operating the modular device 9050. Alternatively, the control program update can change the manually controlled operation of the modular device 9050 to an operation that is controlled by the control program of the modular device 9050. The control program update may or may not permit the user to override the control program's control of the particular function. For example, if the analytics system 9100 determines 9204 that surgeons are manually setting an RF electrosurgical instrument to a suboptimal energy level for a particular tissue type or procedure type, then the analytics system 9100 can generate 9208 a control program update that provides an alert (e.g., on the surgical hub 9000 or the RF electrosurgical instrument itself) recommending that the energy level be changed. For another example, the generated 9208 control program update can automatically set the energy level to a default or recommended level given the particular detected circumstances, which could then be changed as desired by the medical facility staff. For yet another example, the generated 9208 control program update can automatically set the energy level to a set level determined by the analytics system 9100 and not permit the medical facility staff to change the energy level. For still another example, if the analytics system 9100 determines 9204 that more actuations are detected than number of dose deliveries from a drug administration device, then the analytics system 9100 can generate 9208 a control program update that provides an alert (e.g., on the surgical hub 9000 and/or the drug administration device itself) recommending that the user apply a greater force to the drug administration device, e.g., to a trigger thereof, to properly cause drug delivery. For yet another example, if the analytics system 9100 determines 9204 that more doses are delivered from a drug administration device compared to a preoperative plan (specific to a patient's surgical procedure or an average or threshold preoperative plan for a particular type of surgery), then the analytics system 9100 can generate 9208 a control program update that provides an alert (e.g., on the surgical hub 9000 and/or the drug administration device itself) recommending that the user deliver fewer doses or consider using a different drug that may not require as many dose deliveries during surgery. If the suboptimal behavior is caused by the control program of the modular device 9050, then the control program update can alter how the control program functions under the particular set of circumstances that the control program is performing suboptimally under.

Once the control program update has been generated 9208 by the analytics system 9100, the analytics system 9100 then transmits 9210 or pushes the control program update to all of the modular devices 9050 of the relevant type that are connected to the analytics system 9100. The modular devices 9050 can be connected to the analytics system 9100 through the surgical hubs 9000, for example. The surgical hubs 9000 can be configured to download the control program updates for the various types of modular devices 9050 from the analytics system 9100 each time an update is generated 9208 thereby. When the modular devices 9050 subsequently connect to or pair with a surgical hub 9000, the modular devices 9050 can then automatically download any control program updates therefrom. The analytics system 9100 can thereafter continue receiving 9202 and analyzing 9204 data from the modular devices 9050, as described above.

Instead of the modular devices 9050 transmitting recorded data to a surgical hub 9000 to which the modular devices 9050 are connected, the modular devices 9050 can be configured to record the perioperative data and the procedural outcome data on a memory of the modular device 9050. The data can be stored for indefinitely or until the data is downloaded from the modular devices 9050. This allows the data to be retrieved at a later time. For example, the modular devices 9050 can be returned to the manufacturer after they are utilized in a surgical procedure. The manufacturer can then download the data from the modular devices 9050 and then analyze the data as described above to determine whether a control program update should be generated for the modular devices 9050. The data could be uploaded to an analytics system 9100 for analysis, as described above. The analytics system 9100 could then generate update control programs according to the recorded data and then either incorporate that update in future manufactured product or push the update to modular devices 9050 currently in the field.

In order to assist in the understanding of the process 9200 illustrated in FIG. 25 and the other concepts discussed above, FIG. 26 illustrates one embodiment of an illustrative analytics system 9100 updating a surgical instrument control program. The analytics system 9100 is configured to filter and analyze modular device 9050 data associated with surgical procedural outcome data to determine whether adjustments need to be made to the control programs of the modular devices 9050. The analytics system 9100 can then push updates to the modular devices 9050 through the surgical hubs 9000, as necessary. In the illustrated embodiment of FIG. 26, the analytics system 9100 includes a cloud computing architecture. The modular device 9050 perioperative data received by the surgical hubs 9000 from their paired modular devices 9050 can include, for example, force to fire (e.g., the force required to advance a cutting member of a surgical stapling instrument through a tissue), force to close (e.g., the force required to clamp the jaws of a surgical stapling instrument on a tissue), the power algorithm (e.g., change in power over time of electrosurgical or ultrasonic instruments in response to the internal states of the instrument and/or tissue conditions), tissue properties (e.g., impedance, thickness, stiffness, etc.), tissue gap (e.g., the thickness of the tissue), closure rate (e.g., the rate at which the jaws of a surgical instrument clamped shut), needle advancement rate (e.g., rate at which a needle of a drug administration device advanced into a patient), needle retraction rate (e.g., rate at which a needle of a drug administration device retracted after delivering a drug therethrough to a patient), dosage amount (e.g., amount of a drug delivered in a single dose to a patient from a drug administration device), etc. The modular device 9050 data that is transmitted to the analytics system 9100 is not limited to a single type of data and can include multiple different data types paired with procedural outcome data. The procedural outcome data for a surgical procedure (or portions thereof) can include, for example, whether there was bleeding at the surgical site, whether there was air or fluid leakage at the surgical site, whether the staples of a particular staple line were formed properly, whether there was an adverse skin reaction at a site of drug administration, whether excess liquid drug collected on a skin surface of a patient instead of being delivered into the patient from a drug administration device, etc. The procedural outcome data can further include or be associated with a positive or negative outcome, as determined by the surgical hub 9000 or the analytics system 9100, for example. The modular device 9050 data and the procedural outcome data corresponding to the modular device 9050 perioperative data can be paired together or otherwise associated with each other when they are uploaded to the analytics system 9100 so that the analytics system 9100 is able to recognize trends in procedural outcomes based on the underlying data of the modular devices 9050 that produced each particular outcome. In other words, the analytics system 9100 can aggregate the modular device 9050 data and the procedural outcome data to search for trends or patterns in the underlying device modular data 9050 that can indicate adjustments that can be made to the modular devices' 9050 control programs.

Figure 26:
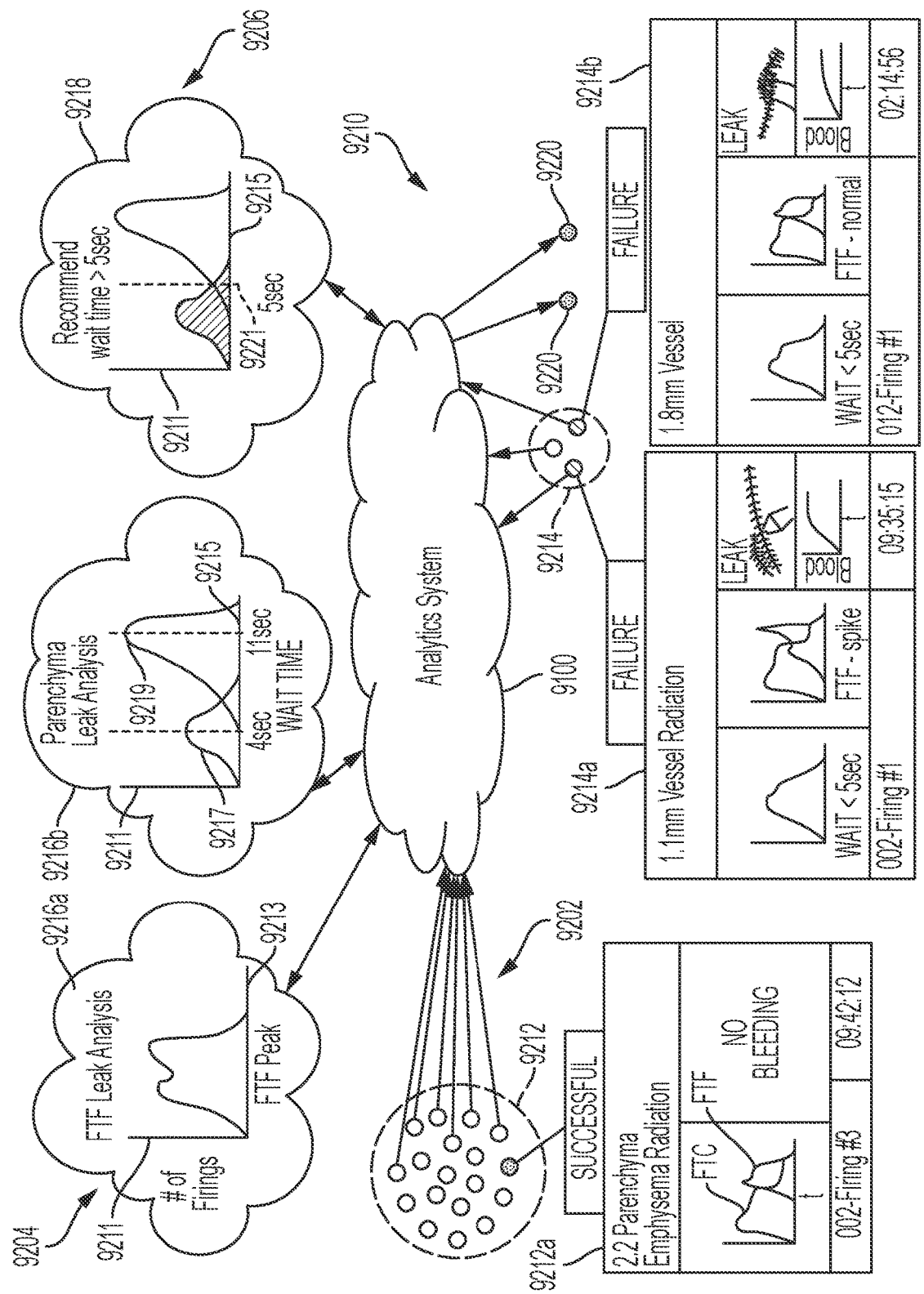
FIG. 26 is a schematic view of one embodiment of an analytics system updating a surgical instrument control program.

In embodiment of FIG. 26, the analytics system 9100 executing the process 9200 described in connection with FIG. 24 is receiving 9202 modular device 9050 data and procedural outcome data. When transmitted to the analytics system 9100, the procedural outcome data can be associated or paired with the modular device 9050 data corresponding to the operation of the modular device 9050 that caused the particular procedural outcome. The modular device 9050 perioperative data and corresponding procedural outcome data can be referred to as a data pair. The data is shown in FIG. 26 as including a first group 9212 of data associated with successful procedural outcomes and a second group 9214 of data associated with negative procedural outcomes. For this particular embodiments, a subset of the data 9212, 9214 received 9202 by the analytics system 9100 is highlighted to further elucidate the concepts discussed herein.

For a first data pair 9212*a*, the modular device 9050 data includes the force to close (FTC) over time, the force to fire (FTF) over time, the tissue type (parenchyma), the tissue conditions (the tissue is from a patient suffering from emphysema and had been subject to radiation), what number firing this was for the instrument (third), an anonymized time stamp (to protect patient confidentiality while still allowing the analytics system to calculate elapsed time between firings and other such metrics), and an anonymized patient identifier ("002" in this example). The procedural outcome data includes data indicating that there was no bleeding, which corresponds to a successful outcome (e.g., a successful firing of the surgical stapling instrument). For a second data pair 9214*a*, the modular device 9050 data includes the wait time prior the instrument being fired (which corresponds to the first firing of the instrument), the FTC over time, the FTF over time (which indicates that there was a force spike near the end of the firing stroke), the tissue type (1.1 mm vessel), the tissue conditions (the tissue had been subject to radiation), what number firing this was for the surgical stapling instrument (first), an anonymized time stamp, and an anonymized patient identifier ("002" in this example). The procedural outcome data includes data indicating that there was a leak, which corresponds to a negative outcome (e.g., a failed firing of the surgical stapling instrument). For a third data pair 9214*b*, the modular device 9050 data includes the wait time prior to the surgical stapling instrument being fired (which corresponds to the first firing of the surgical stapling instrument), the FTC over time, the FTF over time, the tissue type (1.8 mm vessel), the tissue conditions (no notable conditions), what number firing this was for the instrument (first), an anonymized time stamp, and an anonymized patient identifier ("012" in this illustrated example). The procedural outcome data includes data indicating that there was a leak, which corresponds to a negative outcome (e.g., a failed firing of the surgical stapling instrument). This data of FIG. 26 is solely for illustrative purposes to assist in the understanding of the concepts discussed herein and should not be interpreted to limit the data that is received and/or analyzed by the analytics system 9100 to generate control program updates.

When the analytics system 9100 receives 9202 perioperative data from the communicably connected surgical hubs 9000, the analytics system 9100 proceeds to aggregate and/or store the data according to the procedure type (or a portion of the procedure) associated with the data, the type of the modular device 9050 that generated the data, and other such categories. By collating the data accordingly, the analytics system 9100 can analyze the data set to identify correlations between particular ways of controlling each particular type of modular device 9050 and positive or negative procedural outcomes. Based upon whether a particular manner of controlling a modular device 9050 correlates to positive or negative procedural outcomes, the analytics system 9100 can determine 9204 whether the control program for the type of modular device 9050 should be updated.

For the embodiment of FIG. 26, the analytics system 9100 performs a first analysis 9216*a* of the data set by analyzing the peak FTF 9213 (e.g., the maximum FTF for each particular firing of a surgical stapling instrument) relative to the number of firings 9211 for each peak FTF value. In this exemplary case, the analytics system 9100 can determine that there is no particular correlation between the peak FTF 9213 and the occurrence of positive or negative outcomes for the particular data set. In other words, there are not distinct distributions for the peak FTF 9213 for positive and negative outcomes. As there is no particular correlation between peak FTF 9213 and positive or negative outcomes, the analytics system 9100 would thus determine that a control program update to address this variable is not necessary. The analytics system 9100 also performs a second analysis 9216*b* of the data set by analyzing the wait time 9215 prior to the instrument being fired relative to the number of firings 9211. For this particular analysis 9216*b*, the analytics system 9100 can determine that there is a distinct negative outcome distribution 9217 and a positive outcome distribution 9219. In this exemplary case, the negative outcome distribution 9217 has a mean of four seconds and the positive outcome distribution has a mean of eleven seconds. Thus, the analytics system 9100 can determine that there is a correlation between the wait time 9215 and the type of outcome for this surgical procedure step. Namely, the negative outcome distribution 9217 indicates that there is a relatively large rate of negative outcomes for wait times of four seconds or less. Based on this analysis 9216*b* demonstrating that there is a large divergence between the negative outcome distribution 9217 and the positive outcome distribution 9219, the analytics system 9100 can then determine 9204 that a control program update should be generated 9208.

Once the analytics system 9100 analyzes the data set and determines 9204 that an adjustment to the control program of the particular module device 9050 that is the subject of the data set would improve the performance of the modular device 9050, the analytics system 9100 then generates 9208 a control program update accordingly. In this illustrated embodiment, the analytics system 9100 can determine based on the analysis 9216*b* of the data set that a control program update 9218 recommending a wait time of more than five seconds would prevent 90% of the distribution of the negative outcomes with a 95% confidence interval. Alternatively, the analytics system 9100 can determine based on the analysis 9216*b* of the data set that a control program update 9218 recommending a wait time of more than five seconds would result in the rate of positive outcomes being greater than the rate of negative outcomes. The analytics system 9100 could thus determine that the particular type of surgical instrument should wait more than five seconds before being fired under the particular tissue conditions so that negative outcomes are less common than positive outcomes. Based on either or both of these constraints for generating 9208 a control program update that the analytics system 9100 determines are satisfied by the analysis 9216*b*, the analytics system 9100 can generate 9208 a control program update 9218 for the surgical instrument that causes the surgical instrument, under the given circumstances, to either impose a five second or longer wait time before the particular surgical instrument can be fired or causes the surgical instrument to display a warning or recommendation to the user that indicates to the user that the user should wait at least five seconds before firing the instrument. Various other constraints can be utilized by the analytics system 9100 in determining whether to generate 9208 a control program update, such as whether a control program update would reduce the rate of negative outcomes by a certain percentage or whether a control program update maximizes the rate of positive outcomes.

After the control program update 9218 is generated 9208, the analytics system 9100 then transmits 9210 the control program update 9218 for the appropriate type of modular devices 9050 to the surgical hubs 9000. When a modular device 9050 that corresponds to the control program update 9218 is next connected to a surgical hub 9000 that has downloaded the control program update 9218, e.g., that changes at least one variable parameter and/or changes the entire control program, the modular device 9050 then automatically downloads the update 9218. Instead of the modular device 9050 downloaded the control program update 9218, the surgical hub 9000 controls the modular device 9050 according to the control program update 9218, rather than the control program update 9218 being transmitted directly to the modular device 9050 itself.

Figure 27:
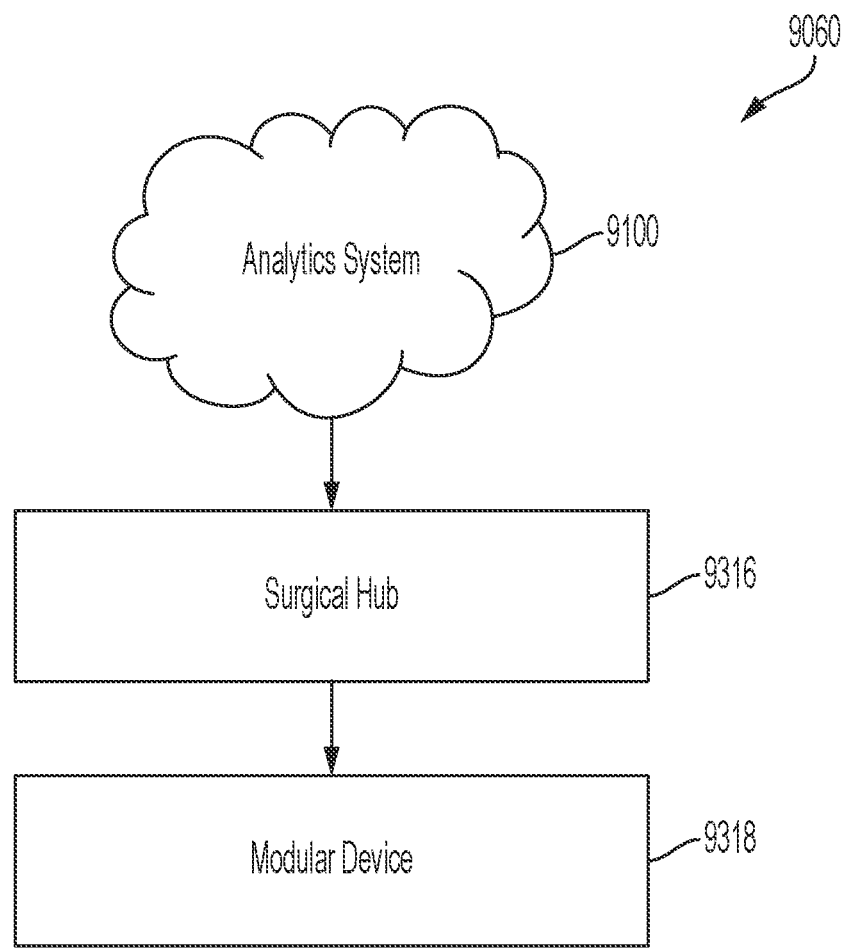
FIG. 27 is a schematic view of one embodiment of an analytics system pushing an update to a modular device through a surgical hub.

The surgical system 9060 is configured to push down verification of software parameters and updates if modular devices 9050 are detected to be out of date in the surgical hub 9000 data stream. FIG. 27 illustrates one embodiment of the analytics system 9100 pushing an update to a modular device 9318 (e.g., the modular device 9050) through a surgical hub 9316 (e.g., the surgical hub 9000). In this illustrated embodiment, the analytics system 9100 is configured to transmit a generated control program update for a particular type of modular device to the surgical hub 9316.

Each time a modular device 9318 connects to the surgical hub 9316, the modular device 9318 determines whether there is an updated version of its control program on or otherwise accessible via the surgical hub 9316. If the surgical hub 9316 does have an updated control program (or the updated control program is otherwise available from the analytics system 9100) for the particular type of modular device 9318, then the modular device 9318 downloads the control program update therefrom.

Any data set being transmitted to the analytics systems 9100 includes a unique ID for the surgical hub 9000 and the current version of its control program or operating system. Any data set being sent to the analytics systems 9100 includes a unique ID for the modular device 9050 and the current version of its control program or operating system. The unique ID of the surgical hub 9000 and/or modular device 9050 being associated with the uploaded data allows the analytics system 9100 to determine whether the data corresponds to the most recent version of the control program. The analytics system 9100 could, for example, elect to discount (or ignore) data generated by a modular device 9050 or surgical hub 9000 being controlled by an out of date control program and/or cause the updated version of the control program to be pushed to the modular device 9050 or surgical hub 9000.

The operating versions of all modular devices 9050 the surgical hub 9000 has updated control software for could be included in a surgical hub 9000 status data block that is transmitted to the analytics system 9100 on a periodic basis. If the analytics system 9100 identifies that the operating versions of the control programs of the surgical hub 9100 and/or any of the connectable modular devices 9050 are out of date, the analytics system 9100 could push the most recent revision of the relevant control program to the surgical hub 9000.

The surgical hub 9000 and/or modular devices 9050 can be configured to automatically download any software updates. Alternatively, the surgical hub 9000 and/or modular devices 9050 can be configured to provide a prompt for a user to ask at the next setup step (e.g., between surgical procedures) if the user wants to update the out of date control program(s). Alternatively, the surgical hub 9000 could be programmable by the user to never allow updates or only allow updates of the modular devices 9050 and not the surgical hub 9000 itself.

Providing Notifications Regarding Data from a Drug Administration Device

Data gathered by a drug administration device, e.g., by one or more sensors thereof, can be communicated to a surgical hub and/or to a cloud, as discussed above. Additionally or alternatively, other data, e.g., data identifying the drug administration devices, values of one or more variable parameters of the drug administration device's control program, the drug administration device's control program, operational data, etc., can be communicated from a drug administration device to a surgical hub and/or to a cloud, as also discussed above. The recipient of the data communicated from the drug administration device can be configured to provide a user a notification regarding the data. The notification can include the data itself, which may allow a medical professional to analyze the data to facilitate treatment of a patient using the drug administration device. The notification can include a warning, which may allow a medical professional to take any one or more corrective actions, such as to cause the surgical hub to communicate an instruction to the drug administration device to change at least one variable parameter of the drug administration device's control program, to contact the patient, to replace the drug administration device with another drug administration device, etc.

Figure 28:
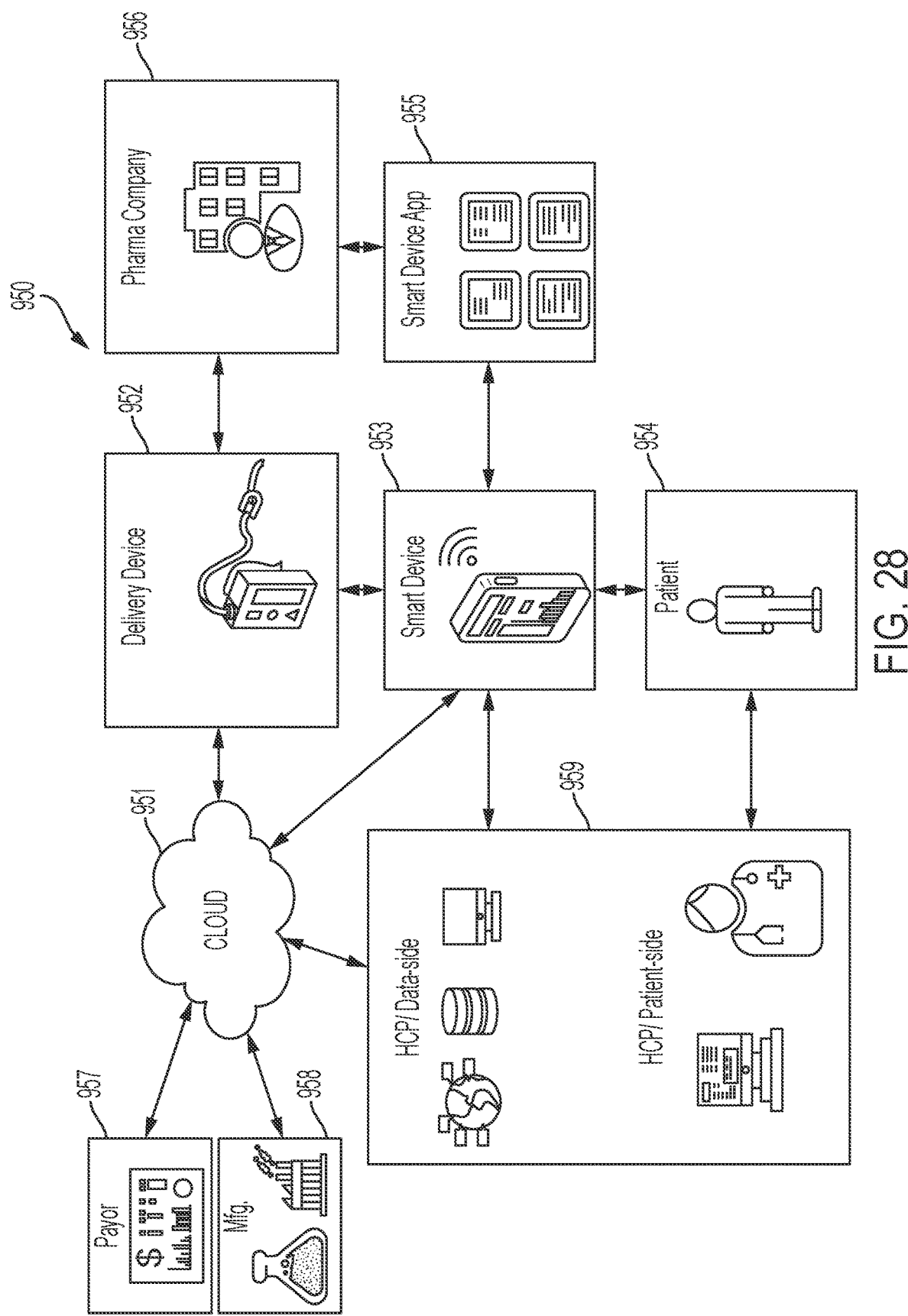
FIG. 28 is a schematic view of one embodiment of a drug administration system including a cloud-based system and a drug administration device.

FIG. 28 illustrates one embodiment of a drug administration system 950 including a cloud-based system 951 configured to communicate with one or more drug administration devices in a secure and anonymized manner using a key-based security system. The drug administration system 950 in this illustrated embodiment includes a drug administration device 952 configured to communicate with the cloud-based system 951, a smart mobile device 953 configured to communicate with the cloud-based system 951 and the drug administration device 952, a patient 954 configured to have a drug delivered thereto from the drug administration device 952 and to interact with the mobile smart device 953, one or more apps 955 installed on the smart device 953 and configured to facilitate a user's interaction with the smart device 953 as related to the drug administration device 952, a pharmaceutical company computer system 956 for a pharmaceutical company associated with the drug and configured to communicate electronically with the one or more apps 955 (e.g., to provide software updates thereto, to push informational notifications thereto to provide to the patient 954, etc.) and with the drug administration device 952 (e.g., to push informational notifications thereto related to the drug to provide to the patient 954 via a user interface of the device 952, etc.), a payor database 957 configured to store payor data related to the patient 954 and to be accessible to the cloud-based system 951, a manufacturing database 958 configured to store drug data related to manufacturing of the drug and to be accessible to the cloud-based system 951, and a patient database 959 configured to store patient data related to the patient 954 and to be accessible to the cloud computing system 951, the patient 954, and the smart device 953. The drug administration device 952 can be any of the drug administration devices discussed above. The patient database 959 includes data-side health care provider (HCP) data regarding the patient 954 that is configured to be accessible to the cloud-based system 951. The patient database 959 also includes patient-side HCP data regarding the patient 954 that is configured to be accessible to the patient 954, such as via the smart device 953 under patient control.

A surgical hub can include the patient database 959. As discussed above, the drug administration device 952 can be configured to communicate with the surgical hub, which can be configured to communicate with the cloud-based system 951.

The drug administration device 952 can be configured to communicate with the cloud-based system 951 and/or the surgical hub using a security system, such as a key-based security system. A key can be established between the drug administration device 952 and the cloud-based system 951 using any of a variety of key establishment protocols. The key can be stored in a memory of the device 952 and stored in a memory of the cloud-based system 951 to allow the drug administration device 952 to encrypt data using the key and to transmit the encrypted data to the cloud-based system 951 securely and in an anonymous manner that does not identify the drug administration device 952 or the patient 954 associated therewith. The drug administration device's memory can also store therein a unique ID number/code for the drug administration device 952. The drug administration device's processor can be configured to use the key in encrypting data indicative of information sensed by any one or more of the drug administration device's one or more sensors (and/or other sensor(s)). Alternatively, the drug administration device 952 can be the sensor itself and so be configured to use the key in encrypting data indicative of information sensed. The data can include metadata for the sensed information, such as time and date the data was collected. The drug administration device's processor can be configured to cause the encrypted data to be transmitted wirelessly to the cloud-based system 951 via the drug administration device's communications interface. The cloud-based system 951 can then receive the data via its communications interface, identify from the received data the correct key stored in its memory to use in decrypting the received data, and then decrypt the received data using the identified, stored key. In this way, the cloud-based system 951 can be configured to remove the anonymized aspect of the data to allow identification of the drug administration device 952 and the patient 954 associated with the data since the key is previously known by the cloud-based system 951 to be associated with that particular drug administration device 952 and patient 954. Conversely, an unauthorized party that intercepts the data transmitted by the drug administration device 952 would not be able to remove the anonymized aspect of the data and, therefore, even in the event that interception occurs, the patient's privacy is maintained. The drug administration device 952 can utilize the generated key to encrypt all data that is transmitted from the device 952 to the cloud-based system 951. The cloud-based system 951 can also utilize the generated key stored thereat to encrypt any data transmitted therefrom to the drug administration device 952, with the drug administration device 952 being able to decrypt that information using its stored key. Data transmitted from the cloud-based system 951 to the drug administration device 952 can include, for example, a request for the device 952 to transmit sensed information to the cloud-based system 951 in embodiments in which the device 952 is not configured to automatically transmit sensed information to the cloud-based system 951. In at least some embodiments, a key can be similarly established and used between the cloud-based system 951 and each of any one or more of the other computer systems 953, 957, 958, 959 in the system 950 with which the cloud-based system 951 is configured to communicate, including a surgical hub.

Figure 29:
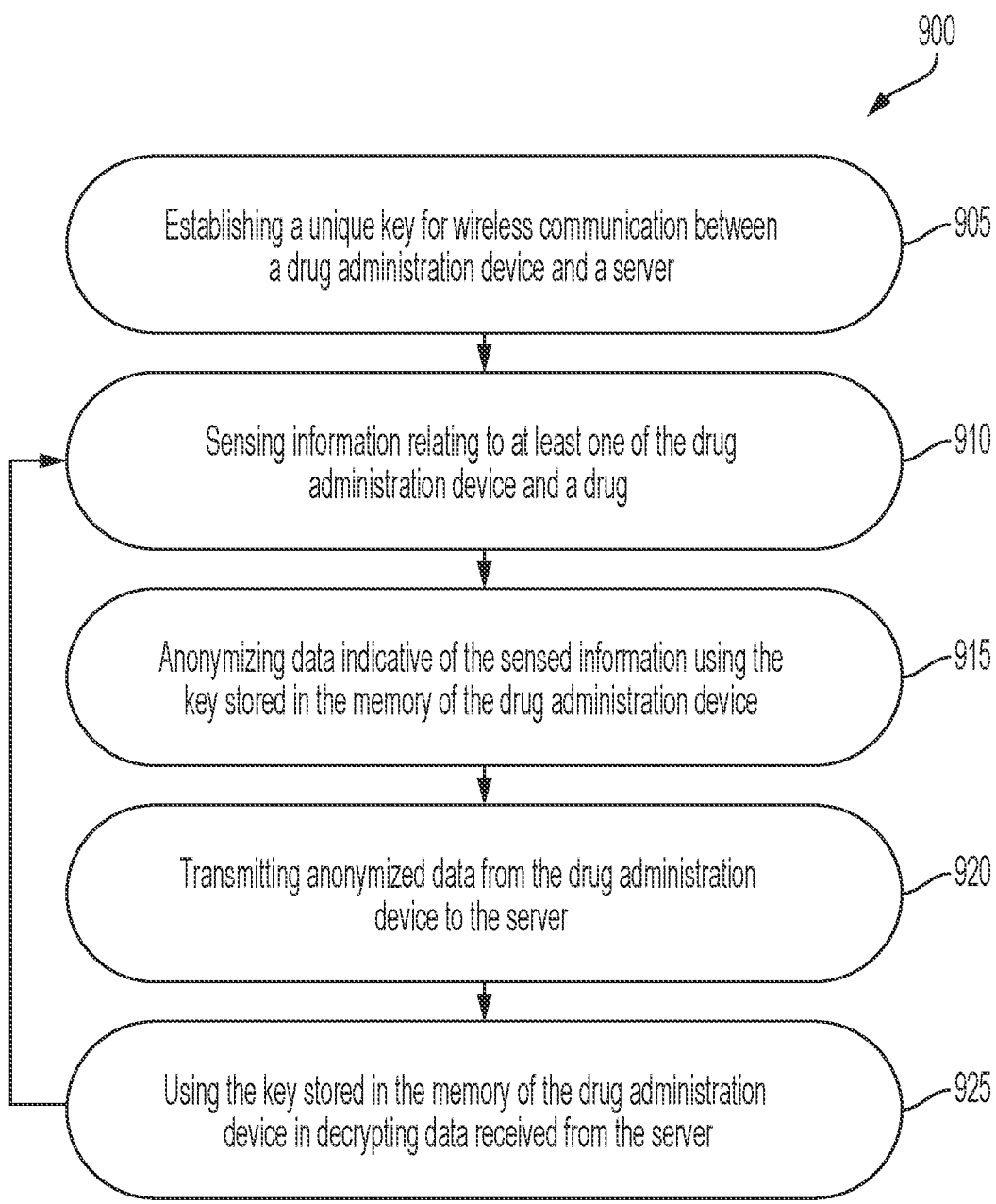
FIG. 29 is a flowchart illustrating one embodiment of a method for administering a drug using a control algorithm.

FIG. 29 illustrates one embodiment of a method 900 using a key-based security system. The method 900 is described with respect to the drug administration devices 500 of FIG. 5 and the system 700 of FIG. 7 for ease of explanation, but other devices and systems, such as the sensor per se when not part of the drug administration device, can be similarly implemented as discussed above. The key-based system is used to encrypt and decrypt data that is transmitted and received between the drug administration device 500 and the system 700 so that data can be passed in a secure, private, anonymized manner.

The key-based security system establishes 905 a unique key for wireless communications between the drug administration device 500 and the system 700, which can be located remotely from the drug administration device 500, e.g., a cloud-based system, etc., or located locally to the drug administration device 500, e.g., a surgical hub in use with the drug administration device 500 during performance of a surgical procedure. In at least some embodiments, a server configured within the system 700 implements the key-based security system. The unique key is stored in a memory of the server, as well as in an additional storage that may be configured with the system 700. The system 700 can transmit the key to the drug administration device 500 for storage in the memory 97 thereof, or the drug administration device 500 can be configured to generate its own key of a key pair to be used in the key-based security system.

The drug administration device 500 senses 910, using one or more of the sensors 92, 94, 98, information relating to at least one of the drug administration device 500 and/or the drug to be dispensed therefrom. The sensed information can include, for example, data associated with the dosage amounts and the delivery schedule of the drug to be administered via the drug administration device 500.

The processor 96 of the drug administration device 500 uses the generated key stored in the memory 97 to encrypt and anonymize 915 data indicative of the sensed information. The processor 96 anonymizes and encrypts the data prior to transmission 920 of the data to the computer system 700 such that when transmitted, the data is transmitted in a secure, encrypted manner. The transmission in operation 920 also includes the device's unique ID number/code to facilitate the computer system's decryption of the data received from the drug administration device 500.

If the drug administration device 500 receives encrypted data from the system 700, the drug administration device 500 uses the key stored in memory 97 to decrypt 925 the data that is received.

In relation to a sensor being configured to sense information relating to a physiological parameter of a patient, whether the drug administration device includes the sensor or the sensor is external to and separate from the drug administration device, the sensor can be configured to obtain information relating to the physiological parameter on a regular basis, e.g., at least once every twenty-four hours, once every twelve hours, once every three hours, once every hour, once every thirty minutes or once every ten minutes, etc. This can be chosen in line with the frequency of data required. This data can then be communicated anonymously to a server, as described herein, at a corresponding frequency or a lower frequency as required. The sensor may therefore enable the collection of data in an anonymous manner such that is can be utilized without risk of identifying the original patient and thus assist with patient acceptance relating to the collection of their data.

As discussed above, a single patient can have a plurality of sensors for measuring different parameters, which can be further physiological parameters. These sensors can all be associated with the same patient within the system allowing the aggregation of data on the server in relation to this patient.

Data associated with a single patient, beyond the physiological information obtained by the sensor, can also be obtained. For example, a drug administration device associated with the patient can also communicate data relating to the patient, as described herein, and be aggregated with the physiological information on the server to give an indication of physiological response to certain drug administration device performance.

A plurality of patients can each have at least one sensor for measuring a physiological parameter. The sensors are each associated with their respective patient within the system allowing the storing of data for each patient. This allows the collection of many data points across a range of patients which may assist in finding trends and correlations. In particular, each of the plurality of patients can have a plurality of sensors contributing to more data points assisting further analysis of observed outcomes. Each of the plurality of patients can have a drug administration device associated with them providing further data to the server.

Communication of sensor data can be repeated at a periodic rate of, for example, once every twenty-four hours. The periodic measurement can be repeated for a duration of at least twenty-four hours such as forty-eight hours, seven days, fourteen day, thirty days, ninety days, one hundred twenty days, one hundred eighty days, three hundred sixty-five days, etc. In this way, it is possible to complete short term tests over hours and days, but also accumulate more data over a longer period of time to enable highly accurate testing. For example, where the monitored physiological parameters include blood glucose level and nutritional intake such as carbohydrate intake and body weight, the steps can be repeated for duration of three hundred sixty-five days to provide a highly accurate long term glucose test that would be otherwise unachievable using traditional methods. This may better inform real world treatment algorithms.

In at least some implementations, data communicated in a secure and anonymized manner from a device, such as any of the drug administration devices of FIGS. 1-6, any of the drug housings 30, 630 of FIGS. 5 and 6, the packaging 35 of FIG. 5, sensors, etc., to a server, such as a surgical hub 1006 of FIG. 9 or the central computer system 700 of FIG. 7, can be used to alter drug delivery. The computer system using data received in a secure, anonymized manner as discussed above to alter drug delivery may help ensure that drug delivery from a drug administration device is altered based on information verified as being associated with the drug administration device since the remote computer system can only decrypt the data if the computer system can identify and has the proper key for decryption. In other words, the data is self-verifying for use in drug delivery alteration since the computer system can only read and use the received data to alter drug delivery if the computer system and the drug administration device have previously established a secure, anonymized communication protocol. Data used to alter drug delivery can, however, be transmitted from the drug administration device to the remote computer system in a way other than the secure, anonymized communication implementations discussed above.

In at least some embodiments, feedback/notifications can be provided to a user based on some aspect of data related to the patient's drug administration device exceeding a threshold or based on a rule. In at least some embodiments, feedback/notifications can be provided in a hierarchical manner based on the criticality of certain individual or combined data parameters. For example, when data associated with the operation of the patient's drug administration device, such as reduced needle penetration depth, is combined with a particular physiological condition sensed via at least one sensor of the drug administration device, such as elevated blood sugar levels, the drug administration device's user interface and/or other user interface, e.g., surgical hub display or other interface, can be configured to notify a user to take action to correct a malfunctioning drug administration device which may be causing elevated blood sugar levels. The feedback/notification can identify the corrective action, such as contacting the patient's medical professional, taking a particular action during performance of a surgical procedure, or requesting an updated control algorithm for the drug administration device.

Notifications and feedback can be configured to be transmitted between devices associated with a computing system. In one embodiment, a drug administration app can exchange data with a drug administration device and/or a housing so that a user can configure notification settings of the drug administration device and/or the housing. In at least some embodiments, the drug administration app can be configured to enable a user to configure audible, visual, or tactile notifications.

Figure 30:
FIG. 30 is a schematic view of one embodiment of a user interface.

FIG. 30 illustrates one embodiment of a user interface 1200 displaying data, feedback, and notifications. In the exemplary embodiment illustrated in FIG. 30, the user interface 1200 is associated with a patient administering insulin via a drug administration device to lower the patient's blood sugar, but other types of drugs and other types of drug administration devices can be used as discussed herein.

The user interface 1200 includes a patient identifier 1205, a date/time identifier 1210, a configuration icon 1215, a current conditions portion 1220, a reminder portion 1225, a summary portion 1230, an indication portion 1235, and a received data portion 1240. In at least some embodiments, the layout and arrangement of the identifiers and portions within the user interface 1200 can be interactively rearranged by the user, as will be appreciated by a person skilled in the art. In this way, the user can create a customizable, dashboard-like, display of data that is organized to suit the user's preferences.

The patient identifier 1205 identifies the patient, "Jane Smith." The user interface 1200 is configured to display the user's name after the user has properly authenticated themselves to the respective device or system they are interacting with to help provide a secure system. A user can authenticate their identity in any number of ways, such as by using single-factor, two-factor, multi-factor, and/or strong authentication methods. A user can authenticate their identity using one or more authentication factors such as a password, pass phrases, a personal identification number (PIN), a challenge response, a security question, an ID card, a security token, a software or hardware token, a fingerprint, a retinal pattern, a signature, the user's face or voice, biometric identifiers, and the like. The user can be the patient or other person, such as a medical professional.

The date/time identifier 1210 displays the current date and time. The current date and time may provide the user with temporal context about reminders, notifications, or other schedule based data, such as a reminder when to administer a next dose of a drug.

The configuration icon 1215 is an interactive graphical affordance or icon that, when selected or otherwise activated, causes the user interface 1200 to display additional functionality associated with the settings and configuration of the user interface. Selection/activation of the configuration identifier 1215 is configured to provide a user with tools to configure, not only the display of the user interface 1200, such as the arrangement or ordering of the identifiers and portions within the user interface, but also configurations of the device displaying the user interface 1200. In at least some embodiments, the configuration identifier 1215 is configured to show information indicative of help information regarding correct usage of the patient's drug administration device or housing for which the user interface 1200 is providing information. For example, the configuration identifier 1215 can include an additional graphical affordance or indicator, such as an icon, a symbol, or a number indicating to a user that an update is available to help the user correctly use the patient's drug administration device or housing for which the user interface 1200 is providing information. The indicated update can be associated with an updated version of the software that is available for download and installation on the patient's drug administration device or housing for which the user interface 1200 is providing information. The scope of permissible configuration changes provided by the configuration identifier 1215 can be adjusted as a preference within the system.

The current conditions portion 1220 of the user interface 1200 includes sensor data, e.g., information sensed by sensors, such as sensors 92, 94, 98 of the drug administration device 500 of FIG. 5, one or more sensors that are external to and separate from a drug administration device in a surgical setting in which the user interface 1200 is provided, sensors of a mobile device on which the user interface 1200 is shown, or other sensors. In this example, the current conditions portion 1220 displays the patient's heart rate (78 beats per minute), body temperature (99.1 degrees Fahrenheit), respiration rate (18 breaths per minute), and activity level (6,235 steps toward a goal of 8,000 steps per day).

The reminder portion 1225 provides reminders regarding one or more upcoming drug doses and/or regarding other aspects of the patient's treatment plan. In this example, the reminder portion 1225 provides a reminder to "Administer next dose: Today @ 9:30 pm." Thus, the user is being reminded that the next dose is to be administered in approximately three hours, as the current time is "6:24 pm." Other examples that can be provided in the reminder portion 1225 include reminders indicating a current need to manually administer a dose of the drug to the patient and reminders to change a battery of the patient's drug administration device, to charge the battery of the patient's drug administration device, to order a medication refill for the drug administration device, etc. In at least some embodiments, an audible, tactile, and/or visual notification can be provided in conjunction with a reminder appearing in the reminder portion 1225 to help encourage a user's notice of the newly provided reminder and/or provided at a time a reminded action is due to help encourage performance of the action at the proper time.

The summary portion 1230 provides a summary view of previously scheduled doses of the drug to the patient. As in this illustrated embodiment, the summary portion 1220 can also provide an indication of the intended treatment effect of the drug on the patient, as shown by "1. Previously Scheduled Doses to Lower Blood Sugar." As shown in FIG. 30, the summary portion 1230 includes a list of three previously scheduled doses, items a-c. As shown by item a, the summary portion 1230 indicates that the previously scheduled dose was administered "Today @ 9:30 am," and was successfully delivered ("Completed") on "1/30/19 @ 9:33 am." In this way, the summary portion 1230 provides the user with an intuitive presentation of the timing of the previously delivered doses compared to a predetermined delivery schedule for those doses. As shown by item a, sub-item i, the summary portion 1230 also provides the user with an indication of the estimated remaining duration of the drug's effect on a patient, "Good through: 1/30/19 @ 11:00 pm." Item c also shows information for a delivered dose ("Yesterday @ 9:30 am—Completed 1/29/19 @ 9:26 am"). The previously scheduled doses shown in the summary portion 1230 can also indicate when a patient missed a previously scheduled dose, shown as item b, "Yesterday @ 9:30 pm—Missed." The summary portion 1230 can be configured to allow scrolling to view additional summary information, e.g., doses scheduled for before "Yesterday @ 9:30 am." Other portions of the user interface 1200 can also be configured to allow scrolling for viewing of additional information.

In at least some embodiments, the summary portion 1230 can include other interactive graphical affordances, such as tabs or icons, which, when selected or activated, are configured to cause the summary portion 1230 to display dose delivery data over time in a graphical manner, such as a graph or chart. In at least some embodiments, the dose delivery data included in the summary portion 1230 can be provided in association with other clinical outcomes, sensed data events, and/or self-reported medical condition data provided by the patient. In at least some embodiments, the dose delivery data included in the summary portion 1230 can be provided in association with data received from a computer system such as the system 700 or from other data sources which may be accessible via the system 700 and network 702.

The indication portion 1235 provides a correlation between a timing of a previously delivered dose of the drug to the patient from the drug administration device or the housing and a timing of a medical event experienced by the patient. In this illustrated embodiment, the indication portion 1235 includes a list of the three most recent previously scheduled doses and one or more sensed characteristics of the patient, which in this illustrated embodiment includes the patient's blood sugar level measured at the time of each of the previously scheduled doses, e.g., measured by one of the drug administration device's sensors. When insulin was properly administered ("Completed" in the summary portion 1230) according to the previously scheduled times as shown by doses 1 and 3, the patient's blood sugar levels were kept within a normal range as shown by the measurement of 85 mg/dL corresponding to dose 1 completed "Today @ 9:30 am" and the measurement of 78 mg/dL corresponding to dose 3 completed "Yesterday @ 9:30 am." However, when the patient missed a dose, dose 2, "Yesterday @ 9:30 pm" ("Missed" in the summary portion 1230), the patient's blood sugar level was 225 mg/dL. The indication portion 1235 can be configured to correlate a timing of a previously delivered dose of a drug with a variety of medical events that may be experienced by the patient at the time of the previously delivered dose. In at least some embodiments, the medical event data may originate from the patient's medical records, and the indication portion 1235 can provide a correlation between the timing of previously delivered doses and medical record data, including for example clinical laboratory results.

The received data portion 1240 displays data that may be received from a local surgical hub and/or a remote location, such as the system 700 of FIG. 7 or a remote data source available through the system 700 via network 702 such as a cloud-based system. As shown in FIG. 30, the received data portion 1240 in this illustrated embodiment includes updated medical record information, "1. Updated Medical Records—Now Available." The updated medical record information can be received from an EMR database 9054 such as the EMR database of FIG. 24, a medical records database configured within the system 700 of FIG. 7, and/or a database associated with a computer system located at medical facility 706 of FIG. 7. In an exemplary embodiment, a user may view the updated medical records by clicking or otherwise selecting a uniform resource locator (URL) that the user interface 1200 has provided. In this illustrated example, clicking the word "here" as shown in "b. Click here to view" is configured to cause the user interface 1200 to provide the updated medical records for display. URLs may be used without limit within the user interface 1200 to provide additional data for display to the user.

As also shown in the received data portion 1240, a user may receive data providing help information about the usage of the drug administration device and/or the housing. For example, the received data portion 1240 can provide an indication of the help information as update information, which in this illustrated embodiment is shown as "2. New Device Software—Available for Download." The help information can include new device configuration settings as well as product documentation, such as a user's manual associated with the patient's drug administration device or housing. A user may cause the help information to be transmitted to and installed on the drug administration device or the housing by clicking or otherwise selecting the configuration identifier 1215.

The received data portion 1240 can include data which may be received from a server based on information sensed or determined by the patient's drug administration device 500 or housing. For example, the received data portion 1240 in this illustrated embodiment includes received data as "3. Compliance Message from Dr. Jones." Based on the patient's drug administration device and/or housing sensor (s) sensing the elevated blood sugar level of 225 mg/dL, which occurred in relation to the drug dosage previously scheduled and not administered "Yesterday @ 9:30 pm," the drug administration device and/or housing can transmit the sensed blood sugar levels (in addition to the drug delivery and compliance data) for display on the user interface 1200 in the received data portion 1240. In this illustrated example, as a result of receiving the sensed blood sugar values (in addition to summary data indicating the missed dosage scheduled for "Yesterday @ 9:30 pm"), the system may notify the patient's medical professional to send a compliance message to the patient to remind the patient, e.g., via notification in the reminder portion 1225, of the appropriate guidance and drug administration schedule necessary to reduce the patient's elevated blood sugar levels. In this way, data that is sensed or otherwise determined by the patient's drug administration device or housing can be transmitted to a remote computer system and/or a local surgical hub, where upon receiving the sensed information, the remote computer system and/or local surgical hub can be configured to generate and transmit data associated with the sensed information back to the drug administration device or housing to be provided to a user via the user interface 1200.

Additional descriptions of data and displays of data provided within a user interface, such as user interface 80 of a drug administration device 500 or housing 630 or user interface 2080 of drug administration device 2002, are provided in U.S. Pat. Pub. No. 2002/0091454 entitled "Remotely Programmable Infusion System" published Jul. 11, 2002 and U.S. Pat. Pub. No. 2008/0139907 entitled "Intelligent Personal Health Management Appliance For The Measurement And Monitoring Of Health Factors And Controlled Delivery Of Drugs" published Jun. 12, 2008, which are hereby incorporated by reference in their entireties.

Devices and systems disclosed herein can be designed to be disposed of after a single use, or they can be designed to be used multiple times. In either case, however, the devices can be reconditioned for reuse after at least one use. Reconditioning can include any combination of the steps of disassembly of the devices, followed by cleaning or replacement of particular pieces, and subsequent reassembly. In particular, the devices can be disassembled, and any number of the particular pieces or parts of the device can be selectively replaced or removed in any combination. Upon cleaning and/or replacement of particular parts, the devices can be reassembled for subsequent use either at a reconditioning facility, or by a surgical team immediately prior to a surgical procedure. Those skilled in the art will appreciate that reconditioning of a device can utilize a variety of techniques for disassembly, cleaning/replacement, and reassembly. Use of such techniques, and the resulting reconditioned device, are all within the scope of the present application.

It can be preferred that devices disclosed herein be sterilized before use. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 issued Feb. 14, 2012 and entitled "System And Method Of Sterilizing An Implantable Medical Device." It is preferred that device, if implanted, is hermetically sealed. This can be done by any number of ways known to those skilled in the art.

The present disclosure has been described above by way of example only within the context of the overall disclosure provided herein. It will be appreciated that modifications within the spirit and scope of the claims may be made without departing from the overall scope of the present disclosure.

What is claimed is:

1. A surgical system, comprising:
   a drug administration device configured to deliver a drug to a patient during performance of a surgical procedure on the patient, wherein the drug administration device includes a first sensor configured to gather data, during the performance of the surgical procedure, regarding a first characteristic, and wherein the drug administration device includes a first communications interface;
   a memory configured to store therein an algorithm including at least one variable parameter;
   a processor configured to control delivery of a dose of the drug from the drug administration device to the patient, during the performance of the surgical procedure, by executing the algorithm;
   wherein the first communications interface is configured to communicate, during the performance of the surgical procedure, the gathered data and data indicating that the algorithm was executed to a server external to and separate from the drug administration device.

2. The system of claim 1, further comprising a user interface configured to provide, during the performance of the surgical procedure, information to a user indicative of the data gathered by the first sensor.

3. The system of claim 2, wherein the drug administration device includes the user interface.

4. The system of claim 2, wherein the server includes a surgical hub, and the surgical hub includes the user interface.

5. The system of claim 1, wherein the drug administration device includes the memory and the processor.

6. The system of claim 5, wherein the processor is also configured to:
   change, during the performance of the surgical procedure, the at least one variable parameter of the algorithm stored in the memory based on the data gathered by the first sensor, and
   after changing the at least one variable parameter, control delivery of another dose of the drug from the drug administration device to the patient, during the performance of the surgical procedure, by executing the algorithm.

7. The system of claim 5, wherein the at least one variable parameter includes at least one of:
   a rate of delivery of the drug from the drug administration device to the patient, and
   a time interval between dose deliveries.

8. The system of claim 1, wherein a value of the at least one variable parameter is based on the data gathered by the first sensor.

9. The system of claim 1, further comprising a second sensor external to and separate from the drug administration device, the second sensor being configured to gather second data, during the performance of the surgical procedure, regarding a second characteristic;
   wherein the first communications interface is configured to receive the second data from the server.

10. The system of claim 9, wherein a value of the at least one variable parameter is based on the second data; and
    the processor is also configured to:
    change, during the performance of the surgical procedure, the at least one variable parameter of the algorithm stored in the memory based on the second data, and
    after changing the at least one variable parameter, control delivery of another dose of the drug from the drug administration device to the patient, during the performance of the surgical procedure, by executing the algorithm.

11. The system of claim 9, wherein the first sensor is configured to gather data at a rate stored in the memory; and
    the processor is also configured to modify the rate based on the second data.

12. The system of claim 1, wherein the drug administration device is one of a syringe and an injection device.

13. A surgical method, comprising:
    gathering data using a first sensor during performance of a surgical procedure on a patient;
    controlling, using a processor, delivery of a dose of a drug from a drug administration device to the patient, during the performance of the surgical procedure, by executing an algorithm stored in a memory, the algorithm including at least one variable parameter; and
    communicating, using a first communications interface and during the performance of the surgical procedure, the gathered data and data indicating that the algorithm was executed to a server external to and separate from the drug administration device.

14. The method of claim 13, further comprising providing, using a user interface and during the performance of the surgical procedure, information to a user indicative of the data gathered by the first sensor.

15. The method of claim 14, wherein at least one of the server and the drug administration device includes the user interface.

16. The method of claim 13, further comprising, using the processor:
    changing, during the performance of the surgical procedure, the at least one variable parameter of the algorithm stored in the memory based on the data gathered by the first sensor, and
    after changing the at least one variable parameter, controlling delivery of another dose of the drug from the drug administration device to the patient, during the performance of the surgical procedure, by executing the algorithm.

17. The method of claim 13, further comprising gathering, using a second sensor external to and separate from the drug administration device, second data, during the performance of the surgical procedure, regarding a second characteristic; and
    receiving, at the first communications interface the second data from the server.

18. The method of claim 17, further comprising, using the processor:
    changing, during the performance of the surgical procedure, the at least one variable parameter of the algorithm stored in the memory based on the second data, and
    after changing the at least one variable parameter, controlling delivery of another dose of the drug from the drug administration device to the patient, during the performance of the surgical procedure, by executing the algorithm.

19. The method of claim 17, wherein the first sensor is configured to gather data at a rate stored in the memory; and
    the method further comprising, using the processor, modifying the rate based on the second data.

20. The method of claim 17, wherein the drug administration device is one of a syringe and an injection device.

* * * * *